United States Patent
Albright et al.

[11] Patent Number: 5,532,235
[45] Date of Patent: Jul. 2, 1996

[54] TRICYCLIC BENZAZEPINE VASOPRESSIN ANTAGONISTS

[75] Inventors: Jay D. Albright; Efren G. Delos Santos, both of Nanuet; Xuemei Du, Valley Cottage; Marvin E. Reich, Rockland; Aranapakam M. Venkatesan, Elmhurst, all of N.Y.

[73] Assignee: American Cyanamid Company, Madison, N.J.

[21] Appl. No.: 373,139

[22] Filed: Jan. 17, 1995

[51] Int. Cl.$^6$ ............... C07D 491/147; C07D 495/14; A61K 31/55
[52] U.S. Cl. ............... 514/215; 540/557; 540/578
[58] Field of Search ............... 540/578; 514/215

[56] References Cited

U.S. PATENT DOCUMENTS

| | | | |
|---|---|---|---|
| 4,766,108 | 8/1988 | Ali | 514/16 |
| 5,055,448 | 10/1991 | Manning et al. | 514/16 |
| 5,070,187 | 12/1991 | Gavras et al. | 530/315 |
| 5,258,510 | 11/1993 | Ogawa et al. | 540/476 |

FOREIGN PATENT DOCUMENTS

| | | |
|---|---|---|
| 0382185 | 2/1990 | European Pat. Off. |
| 0470514 | 8/1991 | European Pat. Off. |
| 0514667 | 4/1992 | European Pat. Off. |
| 0533242 | 9/1992 | European Pat. Off. |
| 0533240 | 9/1992 | European Pat. Off. |
| 0533243 | 9/1992 | European Pat. Off. |
| 0533244 | 9/1992 | European Pat. Off. |
| 0620216 | 4/1994 | European Pat. Off. |
| 9105549 | 5/1991 | Japan. |
| 9404525 | 3/1994 | Japan. |
| 9414796 | 7/1994 | Japan. |
| 9420473 | 9/1994 | Japan. |
| 9412476 | 9/1994 | Japan. |

OTHER PUBLICATIONS

J. Med. Chem., 1992, 35, 3905–3918, Williams et al.
J. Med. Chem., 1992, 35, 3895–3904–Manning et al.
J. Med. Chem., 1992, 35, 382–388, Manning et al.
From Vasopressin Antagonist to Agonist, DN + P 4 (4), May 1991, Ruffolo et al., pp. 217–221.
Br. J. Pharmacol. (1992), 105, 787–791, Yamamura et al.
Science, vol. 252, pp. 572–574, Yamamura et al. (1991).
J. Med. Chem., 1992, 35, 3919–3927, Evans et al.
J. Med. Chem., 1993, 36, 3993–4005, Evans et al.

*Primary Examiner*—Philip I. Datlow
*Attorney, Agent, or Firm*—Steven R. Eck

[57] ABSTRACT

Tricyclic compound of the general Formula I:

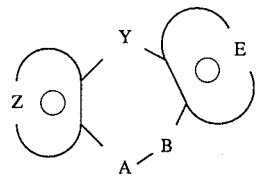

as defined herein which exhibit antagonist activity at $V_1$ and/or $V_2$ receptors and exhibit in vivo vasopressin antagonist activity, methods for using such compounds in treating diseases characterized by excess renal reabsorption of water, and process for preparing such compounds.

20 Claims, No Drawings

TRICYCLIC BENZAZEPINE VASOPRESSIN ANTAGONISTS

FIELD OF THE INVENTION

This invention relates to new tricyclic non-peptide vasopressin antagonists which are useful in treating conditions where decreased vasopressin levels are desired, such as in congestive heart failure, in disease conditions with excess renal water reabsorption and in conditions with increased vascular resistance and coronary vasoconstriction.

BACKGROUND OF THE INVENTION

Vasopressin is released from the posterior pituitary either in response to increased plasma osmolarity detected by brain osmoreceptors or decreased blood volume and blood pressure sensed by low-pressure volume receptors and arterial baroreceptors. The hormone exerts its action through two well defined receptor subtypes: vascular $V_1$ and renal epithelial $V_2$ receptors. Vasopressin-induced antidiuresis, mediated by renal epithelial $V_2$ receptors, helps to maintain normal plasma osmolarity, blood volume and blood pressure.

Vasopressin is involved in some cases of congestive heart failure where peripheral resistance is increased. $V_1$ antagonists may decrease systemic vascular resistance, increase cardiac output and prevent vasopressin induced coronary vasoconstriction. Thus, in conditions with vasopressin induce increases in total peripheral resistance and altered local blood flow, $V_1$-antagonists may be therapeutic agents. $V_1$ antagonists may decrease blood pressure, induced hypotensive effects and thus be therapeutically useful in treatment of some types of hypertension.

The blockage of $V_2$ receptors is useful in treating diseases characterized by excess renal reabsorption of free water. Antidiuresis is regulated by the hypothalamic release of vasopressin (antidiuretic hormone) which binds to specific receptors on renal collecting tubule cells. This binding stimulates adenylyl cyclase and promotes the cAMP-mediated incorporation of water pores into the luminal surface of these cells. $V_2$ antagonists may correct the fluid retention in congestive heart failure, liver cirrhosis, nephritic syndrome, central nervous system injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of antidiuretic hormone, On the basis of biochemical and pharmacological effects of the hormone, antagonists of vasopressin are expected to be therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, thrombosis-bleeding and abnormal states of water retention.

The following prior art references describe peptide vasopressin antagonists: M. Manning et al., *J. Med. Chem.*, 35, 382(1992); M. Manning et al., *J. Med. Chem.*, 35, 3895(1992); H. Gavras and B. Lammek, U.S. Pat. No. 5,070,187 (1991); M. Manning and W. H. Sawyer, U.S. Pat. No. 5,055,448(1991) F. E. Ali, U.S. Pat. No. 4,766,108(1988); R. R. Ruffolo et al., *Drug News and Perspective*, 4(4), 217, (May) (1991). P. D. Williams et al., have reported on potent hexapeptide oxytocin antagonists [*J. Med. Chem.*, 35, 3905(1992)] which also exhibit weak vasopressin antagonist activity in binding to $V_1$ and $V_2$ receptors. Peptide vasopressin antagonists suffer from a lack of oral activity and many of these peptides are not selective antagonists since they also exhibit partial agonist activity.

Non-peptide vasopressin antagonists have recently been disclosed, Y. Yamamura et al., *Science*, 252, 579(1991); Y. Yamamura et al., *Br. J. Pharmacol*, 105, 787(1992); Ogawa et al., (Otsuka Pharm Co., LTD.) EP 0514667-A1; EPO 382185-A2; WO9105549 and U.S. Pat. No. 5,258,510; WO 9404525 Yamanouchi Pharm. Co.,Ltd., WO 9420473; WO 9412476; WO 9414796; Fujisawa Co. Ltd., EP 620216-A1 Ogawa et al, (Otsuka Pharm. Co.) EP 470514A disclose carbostyril derivatives and pharmaceutical compositions containing the same. Non-peptide oxytocin and vasopressin antagonist have been disclosed by Merck and Co.; M. G. Bock and P. D. Williams, EP 0533242A; M. G. Bock et al., EP 0533244A; J. M. Erb, D. F. Verber, P. D. Williams, EP 0533240A; K. Gilbert et al., EP 0533243A.

Premature birth can cause infant health problems and mortality and a key mediator in the mechanism of labor is the peptide hormone oxytocin. On the basis of the pharmacological action of oxytocin, antagonists of this hormone are useful in the prevention of preterm labor, B. E. Evans et al., *J. Med. Chem.* 35, 3919(1992), *J. Med. Chem.*, 36, 3993(1993) and references therein. The compounds of this invention are antagonists of the peptide hormone oxytocin and are useful in the control of premature birth.

The present invention relates to novel tricyclic derivatives which exhibit antagonist activity at $V_1$ and/or $V_2$ receptors and exhibit in vivo pressin antagonist activity. The compounds also exhibit antagonists activity of oxytocin receptors.

SUMMARY OF THE INVENTION

This invention relates to new compounds selected from those of the general Formula I:

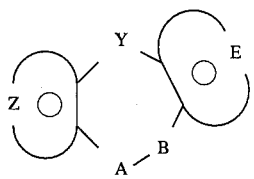

wherein Y is a bond or a moiety selected from —($CH_2$)—, —CHOH, —CHO-lower alkyl($C_1$–$C_6$), —CH—S-lower alkyl($C_1$–$C_6$), —$CHNH_2$, —CHN-lower alkyl($C_1$–$C_6$), —C[N-lower alkyl($C_1$–$C_6$)]$_2$,

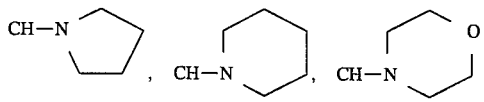

—CHOCO-lower alkyl($C_1$–$C_6$), —CHNH($CH_2$)$_m$$NH_2$; —CHNH($CH_2$)$_m$—NH-lower alkyl($C_1$–$C_6$), —CHNH($CH_2$)$_m$-N[lower alkyl($C_1$–$C_6$)]$_2$; —CHNH($CH_2$)$_m$-S-lower alkyl($C_1$–$C_6$), —CHNH($CH_2$)$_m$-O-lower alkyl($C_1$–$C_6$),

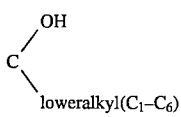

S, O, —NH, —N-lower alkyl($C_1$–$C_6$), —NCO-lower alkyl($C_1$–$C_6$), m is an integer of 2 to 6;

A-B is a moiety selected from

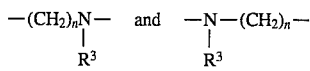

wherein n is an integer 1 or 2 provided that when Y is a bond, n is 2; and the moiety:

represents: (1) an unsaturated 6-membered heterocyclic aromatic ring containing one nitrogen atom, optionally substituted by one or two substitutents selected from ($C_1$–$C_3$)lower alkyl, halogen, amino, ($C_1$–$C_3$)lower alkoxy or ($C_1$–$C_3$)lower alkylamino; (2) a 5-membered aromatic (unsaturated) heterocyclic ring having one heteroatom selected from O, or S; and the moiety:

represents: (1) an unsaturated 6-membered heterocyclic aromatic ring containing one or two nitrogen atoms, optionally substituted by one or two substituents selected from ($C_1$–$C_3$)lower alkyl, halogen, amino, ($C_1$$C_3$)lower alkoxy or ($C_1$–$C_3$)lower alkylamino; (2) a 5-membered aromatic (unsaturated) heterocyclic ring having one heteroatom selected from O, N or S; (3) a 5-membered aromatic (unsaturated) heterocyclic ring having two adjacent nitrogen atoms; (4) a 5-membered aromatic (unsaturated) heterocyclic ring having one nitrogen atom together with either one oxygen or one sulfur atom; wherein the 5 or 6-membered heterocyclic rings are optionally substituted by ($C_1$–$C_3$)lower alkyl, halogen, or ($C_1$–$C_3$)lower alkoxy;

$R^3$ is —COAr, wherein Ar is a moiety selected from the group consisting of:

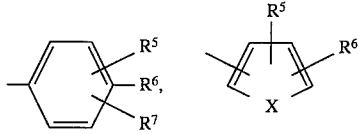

and

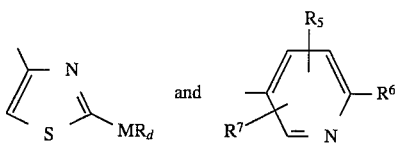

wherein X is selected from O, S, —NH, —$NCH_3$ and —$NCOCH_3$;

$R^4$ is selected from hydrogen, lower alkyl($C_1$–$C_3$), —CO-lower alkyl($C_1$–$C_3$), $R^1$ and $R^2$ are selected from hydrogen, ($C_1$–$C_3$)lower alkyl, ($C_1$–$C_3$)lower alkoxy and halogen; $R^5$ is selected from hydrogen, ($C_1$–$C_3$)lower alkyl, ($C_1$–$C_3$)lower alkoxy and halogen; $R^6$ is selected from (a) moieties of the formulae:

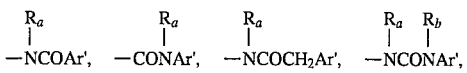

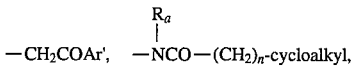

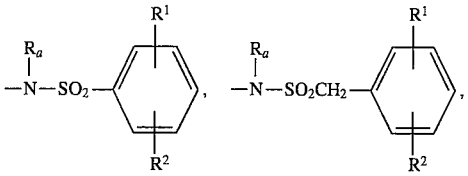

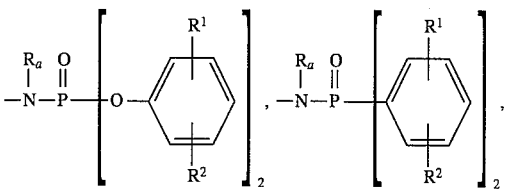

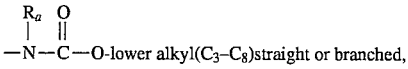

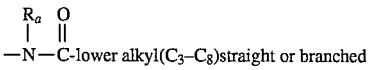

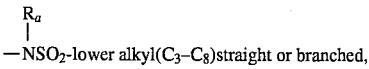

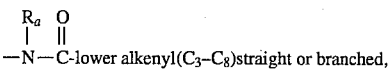

wherein cycloalkyl is defined as ($C_3$–$C_6$) cycloalkyl, cyclohexenyl or cyclopentenyl; and $R_a$ is independently selected from hydrogen, —$CH_3$ or —$C_2H_5$,

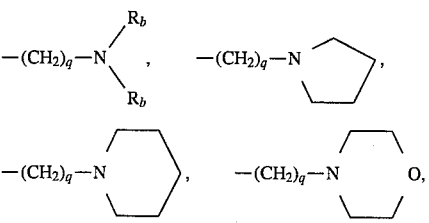

—$(CH_2)_q$-O-lower alkyl($C_1$–$C_3$), —$CH_2CH_2OH$, q is one, two, or three, $R_b$ is independently selected from hydrogen, —$CH_3$ or —$C_2H_5$, (b) a moiety of the formula:

wherein J is $R_a$, lower alkyl($C_3$–$C_8$) branched or unbranched, lower alkenyl($C_3$–$C_8$) branched or unbranched, O-lower alkyl($C_3$–$C_8$) branched or unbranched, —O-lower alkenyl($C_3$–$C_8$) branched or unbranched, tetrahydrofuran, tetrahydrothiophene, and the moieties:

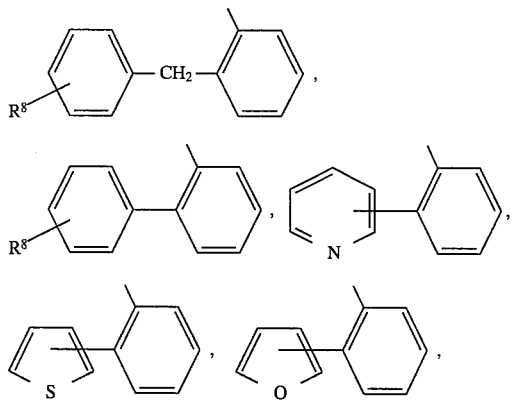

or —CH$_2$—K' wherein K' is (C$_1$–C$_3$)-lower alkoxy, halogen, tetrahydrofuran, tetrahydro-thiophene or the heterocyclic ring moiety:

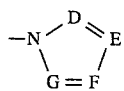

wherein D, E, F and G are selected from carbon or nitrogen and wherein the carbon atoms may be optionally substituted with halogen, (C$_1$–C$_3$)lower alkyl, hydroxy, —CO-lower alkyl(C$_1$–C$_3$), CHO, (C$_1$–C$_3$)lower alkoxy, —CO$_2$-lower alkyl(C$_1$–C$_3$), and R$_a$ and R$_b$ are as hereinbefore defined;

(c) a moiety of the formula:

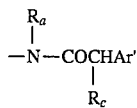

wherein R$_c$ is selected from halogen, (C$_1$–C$_3$) lower alkyl, —O-lower alkyl(C$_1$–C$_3$), OH,

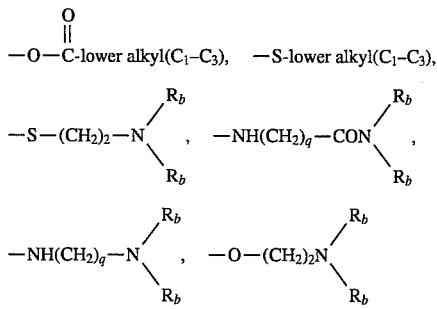

wherein R$_a$ and R$_b$ are as hereinbefore defined;

(d) a moiety of the formula:
wherein R$_d$ is lower alkyl(C$_3$–C$_8$), lower alkenyl(C$_3$–C$_8$), —(CH$_2$)p-cycloalkyl(C$_3$–C$_6$), when M is O, S, NH, NCH$_3$ and the moiety —M—R$_d$ wherein R$_d$ is selected from the moieties:

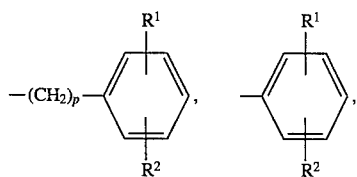

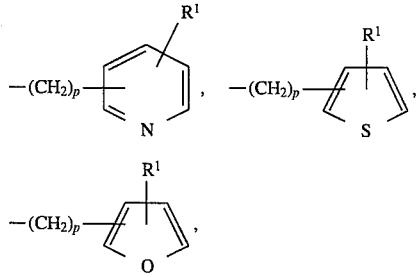

wherein p is zero to four and M is a bond or M is selected from O, S, NH, NCH$_3$; wherein R$^1$, R$^2$ and R$_a$ are as hereinbefore defined;
wherein Ar' is selected from moieties of the formula:

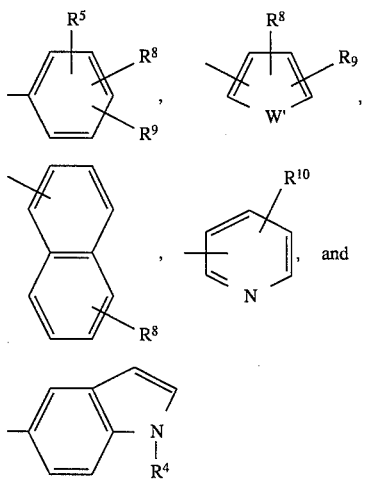

wherein W' is selected from O, S, NH, N-lower alkyl(C$_1$–C$_3$) NHCO-lower alkyl(C$_1$–C$_3$), and NSO$_2$lower alkyl(C$_1$–C$_3$); R$^7$ is selected from hydrogen, lower alkyl(C$_1$–C$_3$), halogen, O-lower alkyl(C$_1$–C$_3$) and CF$_3$; R$^8$ and R$^9$ are independently selected from hydrogen, lower alkyl(C$_1$–C$_3$), —S-lower alkyl(C$_1$–C$_3$), halogen, —NH-lower alkyl(C$_1$–C$_3$), —N-[lower alkyl(C$_1$–C$_3$)]$_2$, —OCF$_3$, —OH, —CN, —S—CF$_3$, —NO$_2$, —NH$_2$, O-lower alkyl(C$_1$–C$_3$), NHCO lower alkyl(C$_1$–C$_3$), —O—CO-lower alkyl (C$_1$–C$_3$) and CF$_3$ and;

R$^{10}$ is selected from hydrogen, halogen, lower alkyl(C$_1$–C$_3$), —NH-lower alkyl (C$_1$–C$_3$), —N-[lower alkyl(C$_1$–C$_3$)]$_2$, —O-lower alkyl(C$_1$–C$_3$), —N(R$_b$)(CH$_2$)$_q$-N(R$_b$)$_2$; and the pharmaceutically acceptable salts thereof.

DETAILED DESCRIPTION OF THE INVENTION

Within the group of the compounds defined by Formula I, certain subgroups of compounds are broadly preferred. Broadly preferred are those compounds wherein R$^3$ is the moiety:

and Ar is selected from the moiety:

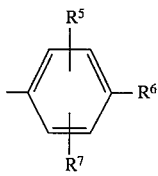

wherein $R_a$, $R_b$, $R^1$, $R^2$, $R^5$, $R^6$ and $R^7$ are as hereinbefore defined.

Especially preferred are compounds wherein $R^3$ is the moiety:

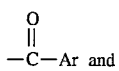

and

Ar is selected from the moiety:

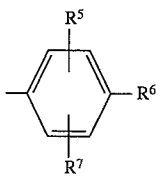

$R^6$ is

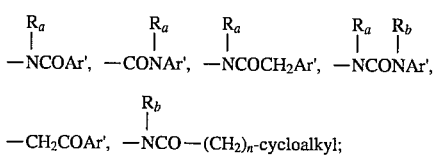

wherein cycloalkyl is defined as $C_3$ to $C_6$ cycloalkyl, cyclohexenyl or cyclopentenyl;

$R_a$, $R_b$, $R^1$, $R^2$, $R^5$, $R^6$, $R^7$ as hereinbefore defined; and Ar' is selected from the moieties:

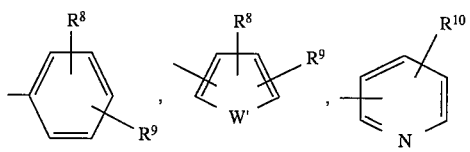

wherein $R^8$, $R^9$, $R^{10}$ and W' are as hereinbefore defined.

Also especially preferred are compounds wherein Y is $CH_2$, —CHOH, —$CHNH_2$, —CHNH-lower alkyl($C_1$–$C_3$), —CHN[lower alkyl($C_1$–$C_3$)]$_2$ and —CHO-lower alkyl($C_1$–$C_3$); and $R_a$, $R_b$, $R^1$, $R^2$, $R^4$, $R^5$, $R^6$, $R^7$, $R^8$ and $R^9$ are as hereinbefore defined.

The most preferred of the compounds of Formula I are those wherein Y is $CH_2$, —CHOH, —$CHNH_2$, —CHNH-lower alkyl ($C_1$–$C_3$), —CHN[lower alkyl ($C_1$–$C_3$)]$_2$ and —CHO-lower alkyl ($C_1$–$C_3$);

$R^3$ is the moiety

Ar is selected from the moieties:

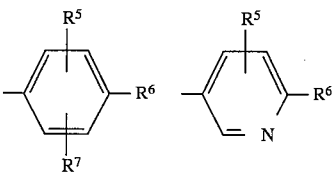

$R^6$ is

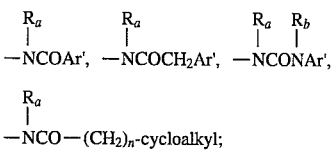

$(CH_2)_n$-cycloalkyl wherein cycloalkyl is defined as ($C_3$–$C_6$) cycloalkyl, cyclohexenyl or cyclopentenyl; $R_a$, $R_b$, $R^1$, $R^2$, $R^5$, $R^7$ are as hereinbefore defined; and Ar' is a moiety:

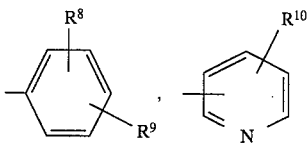

wherein $R^8$, $R^9$, and $R^{10}$ are as previously defined.

The most highly broadly preferred of the compounds of Formula I are those wherein Y is a bond or $CH_2$, —CHOH, —$CHNH_2$, —CHNH-lower alkyl($C_1$–$C_3$), —CHN[lower alkyl($C_1$–$C_3$)]$_2$ and —CHO lower alkyl($C_1$–$C_3$), wherein the moiety:

is an unsubstituted or substituted thiophene, furan, pyrrole, or pyridine ring; and wherein the moiety:

is (1) an unsaturated 6-membered heterocyclic aromatic ring containing one or two nitrogen atoms; (2) a 5-membered aromatic (unsaturated) heterocyclic ring having one heteroatom selected from O, N, or S; (3) a 5-membered aromatic (unsaturated) heterocyclic ring having two adjacent nitrogen atoms.

$R_a$, $R_b$, $R^1$, $R^2$, $R^4$, $R^5$, $R^7$, $R^8$, $R^9$, and $R^{10}$ are as previously defined;

$R^3$ is the moiety:

wherein Ar is:

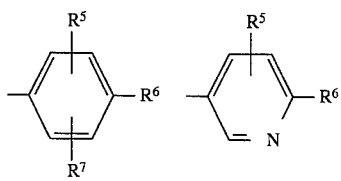

and $R^6$ is selected from the group

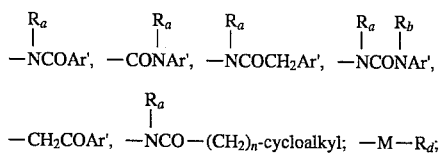

where Ar' is selected from the group

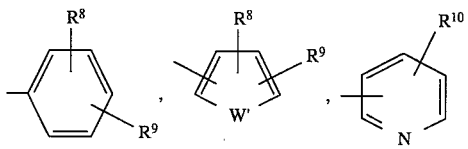

and W' and cycloalkyl are as previously described.

More particularly preferred are compounds of the formula:

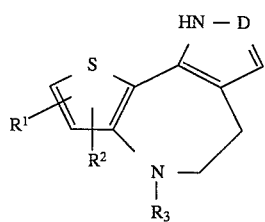

wherein D is —CH or N;
$R^3$ is the moiety:

wherein Ar is selected from the moieties:

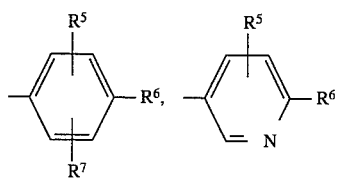

$R^6$ is

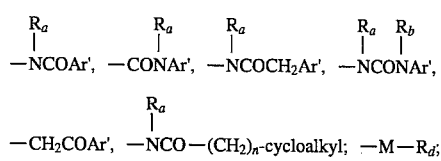

and Ar' is selected from the moieties:

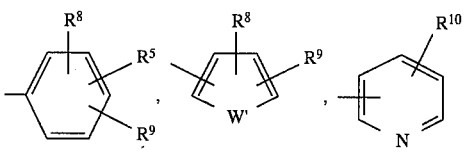

wherein $R_a$, $R_b$, $R^1$, $R^2$, $R^5$, $R^7$, $R^8$, $R^9$, $R^{10}$, cycloalkyl and W' are as hereinbefore described.

Also particularly preferred are compounds of the formula:

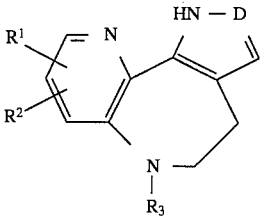

wherein D is —CH or N;
$R^3$ is the moiety:

wherein Ar is selected from the moieties:

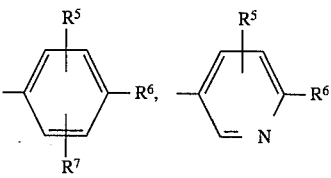

$R^6$ is

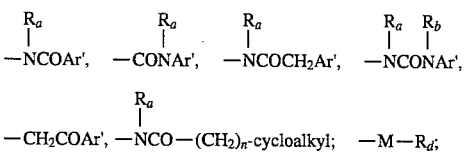

Ar' is selected from the moieties:

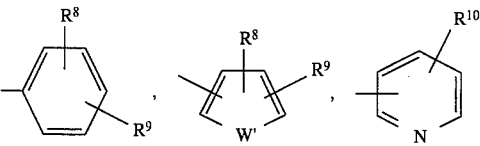

wherein $R_a$, $R_b$, $R^1$, $R^2$, $R^5$, $R^6$, $R^8$, $R^9$, $R^{10}$, cycloalkyl M, $R_d$, and W' are as hereinbefore described.

More particularly preferred are compounds of the formulae:

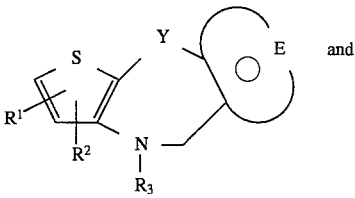

and

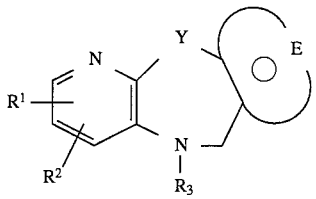

wherein Y is selected from —CH₂, —CHOH, —CHNH₂, —CHNH-lower alkyl(C₁–C₃), —CHN[lower alkyl(C₁–C₃)]₂ and —CHO lower alkyl(C₁–C₃); and the moiety:

represents: (1) an unsaturated 6-membered heterocyclic aromatic ring containing one nitrogen atom, optionally substituted by one or two substituents selected from (C₁–C₃)lower alkyl, halogen, amino, (C₁–C₃)lower alkoxy or (C₁–C₃)lower alkylamino; (2) a 5-membered aromatic (unsaturated) heterocyclic ring having one heteroatom selected from O, N or S; (3) a 5-membered aromatic (unsaturated) heterocyclic ring having two adjacent nitrogen atoms; wherein the 5 or 6-membered heterocyclic rings are optionally substituted by (C₁–C₃)lower alkyl, halogen, or (C₁–C₃)lower alkoxy;

R³ is the moiety:

wherein Ar is the moiety:

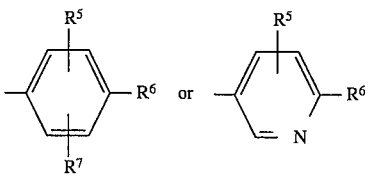

R⁶ is

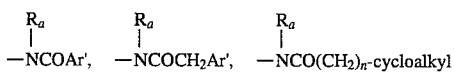

wherein $R_a$ is independently selected from hydrogen or —CH₃; Ar' is selected from the moieties:

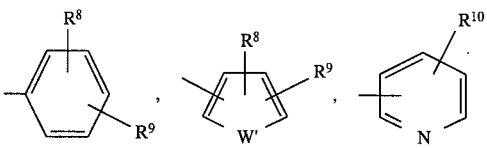

wherein R¹, R², R⁵, R⁷, R⁸, R⁹, R¹⁰, and W' are as hereinbefore described.

Also particularly preferred are compounds of the formulae:

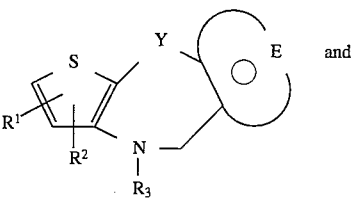

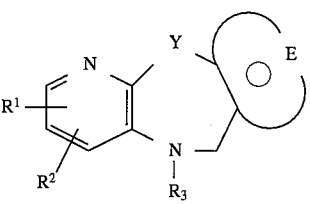

wherein Y is selected from —CH₂, —CHOH, —CHNH₂, —CHNH-lower alkyl(C₁–C₃), —CHN[lower alkyl(C₁–C₃)]₂ and —CHO lower alkyl(C₁–C₃); and the moiety:

represents: (1) an unsaturated 6-membered heterocyclic aromatic ring containing one nitrogen atom, optionally substituted by one or two substituents selected from (C₁–C₃)lower alkyl, halogen, amino, (C₁–C₃)lower alkoxy or (C₁–C₃)lower alkylamino; (2) a 5-membered aromatic (unsaturated) heterocyclic ring having one heteroatom selected from N or S;

R³ is the moiety:

wherein Ar is selected from the moieties:

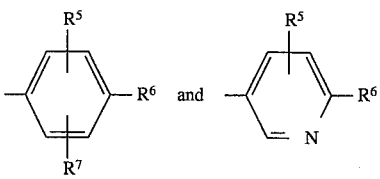

R⁶ is

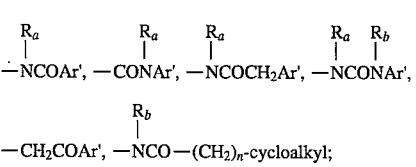

$R_a$ is independently selected from hydrogen, —CH$_3$ or —C$_2$H$_5$ and Ar' is selected from the moieties:

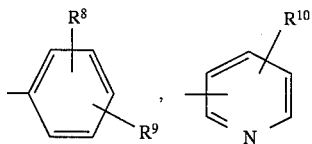

wherein $R^1$, $R^2$, $R^5$, $R^7$, $R^8$, $R^9$, and $R^{10}$ are as hereinbefore defined.

Compounds of this invention may be prepared as shown in Scheme I by reaction of azepine derivatives of Formula 3 with a substituted or unsubstituted 4-nitrobenzoyl chloride 4a or a substituted or unsubstituted 6-aminopyridine-3-carbonyl chloride 4b to give the intermediate 5a and 5b. Reduction of the nitro group in intermediate 5 gives the 4-aminobenzoyl derivative 6a and the 6-aminonicotinoyl derivative 6b. The reduction of the nitro group in intermediate 5 may be carried out under catalytic reduction conditions (hydrogen-Pd/C; Pd/C-hydrazine-ethanol) or under chemical reduction conditions (SnCl$_2$-ethanol; Zn-acetic acid TlCl$_3$) and related reduction conditions known in the art for converting a nitro group to an amino group. The conditions for conversion of the nitro group to the amino group are chosen on the basis of compatability with the preservation of other func-tional groups in the molecule.

Reaction of compounds of Formula 6 with aroyl chloride or related activated aryl carboxylic acids in solvents such as chloroform, dichloromethane, dioxane, tetrahydrofuran, toluene and the like in the presence of a tertiary base such as triethylamine and diisopropylethylamine or pyridine and the like, affords the compounds 8 which are vasopressin antagonists.

Scheme 1

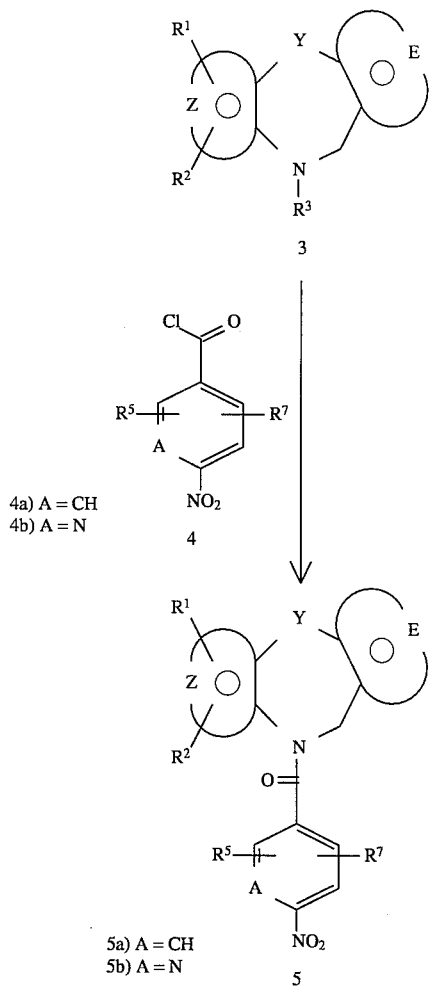

-continued
Scheme 1

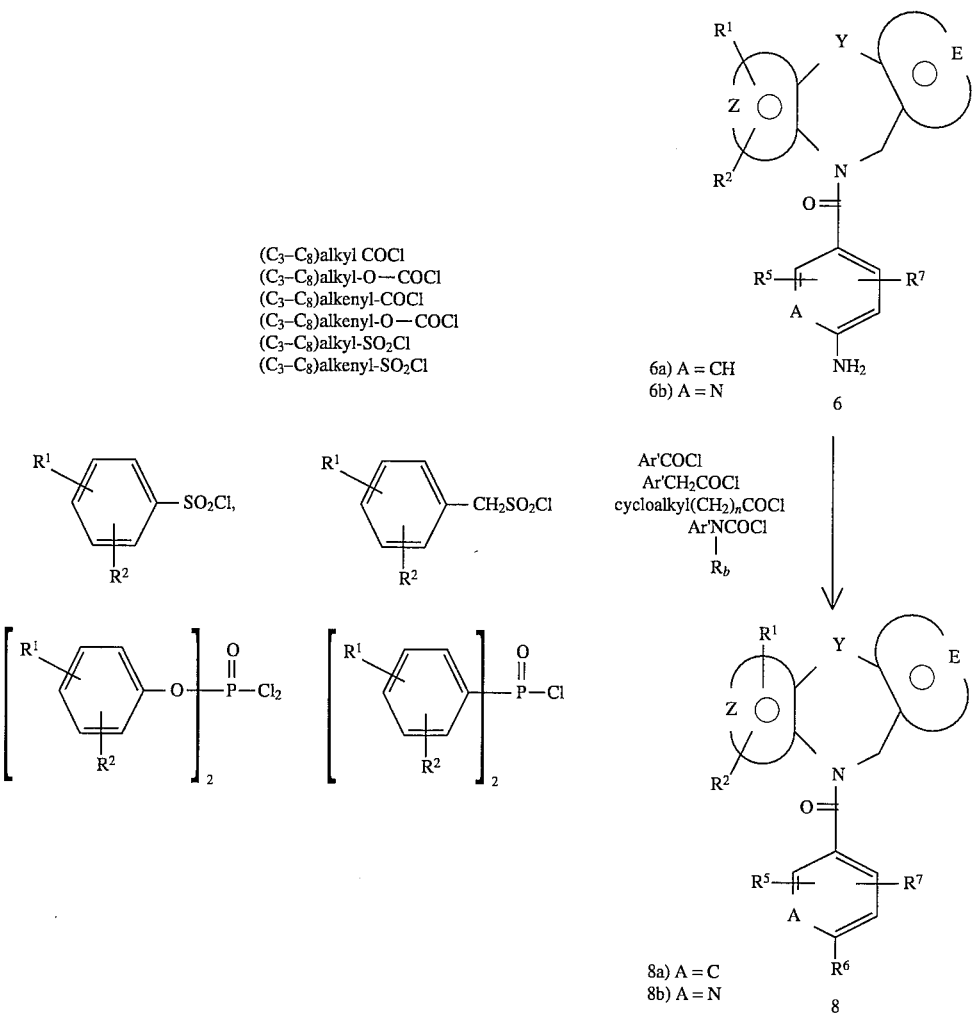

(C$_3$–C$_8$)alkyl COCl
(C$_3$–C$_8$)alkyl-O—COCl
(C$_3$–C$_8$)alkenyl-COCl
(C$_3$–C$_8$)alkenyl-O—COCl
(C$_3$–C$_8$)alkyl-SO$_2$Cl
(C$_3$–C$_8$)alkenyl-SO$_2$Cl Reaction of tricyclic derivatives of Formula 6 with either a carbamoyl derivative 9 or a isocyanate derivative 10 gives compounds (Scheme 2) of Formula 11 which are vasopressin antagonists of Formula I wherein R$^6$ is —NHCONAr'
  |
  R$_b$

Scheme 2

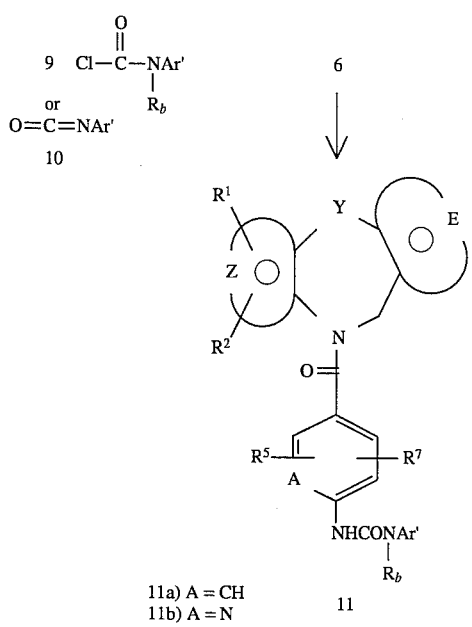

11a) A = CH
11b) A = N

Reaction of tricyclic derivatives of Formula 6 with arylacetic acids, activated as the acid chlorides 12, anhydrides, mixed anhydrides or activated with known activating reagents, gives compounds 13 (Scheme 3).

Scheme 3

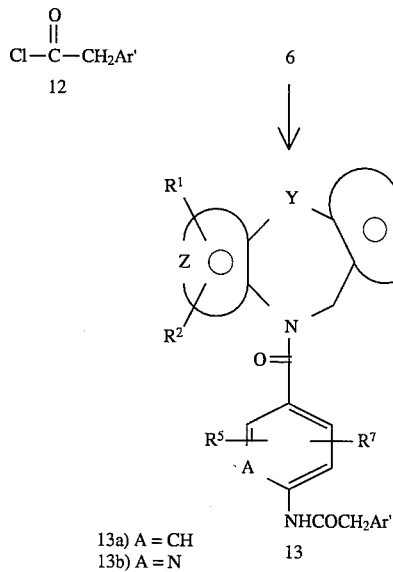

13a) A = CH
13b) A = N

The compounds of Formula I wherein Y, $R^1$, $R^2$, $R^3$ and $R^4$ are as defined and the moiety:

is as previously defined and the Ar' moiety is:

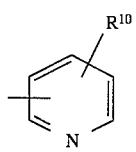

and $R^{10}$ is —NH lower alkyl($C_1$–$C_3$) and —N-[lower alkyl($C_1$–$C_3$)]$_2$ may be prepared, as shown in Scheme 4, by reacting the tricyclic derivatives 6a and 6b with a pyridinecarbonyl chloride 14 to give the derivatives 15. The derivatives 15 are reacted with the appropriate mono alkylamines or dialkylamines to give vasopressin antagonists of formulae 16.

Scheme 4

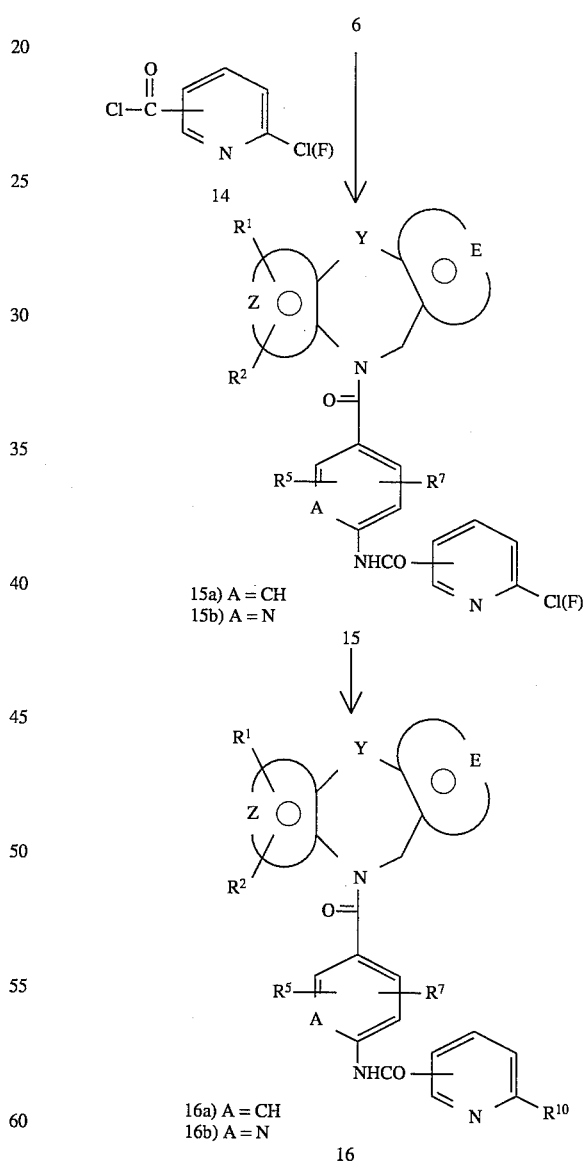

15a) A = CH
15b) A = N

16a) A = CH
16b) A = N

The compounds of Formula I wherein E, Y, $R^1$, $R^2$, $R^3$, $R^5$, and $R^7$ are as defined and the $R^3$ (—COAr) aryl group is

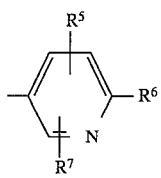

wherein $R^6$ is —M—$R_d$ wherein M is O, S, NH, N—CH$_3$ and $R_d$ is as previously defined may be prepared as shown in Scheme 5 by first converting the azepine derivatives 3 into the intermediate 17 and then reacting these nicotinolyl intermediates with derivatives of the formulae: HM-$R_d$ in the presence of a non-nucleophilic base such as N,N-diisopropylethylamine to give products 18. The best results are obtained in the displacement of the halogen in the pyridine intermediates 17, when the halogen atom is a fluoro group. With nucleophilic amines (M=NH, NCH$_3$) the reaction can be carried out with the 6-chloro, bromo or fluoro derivatives 17 in (1) the absence of a non-nucloephilic base; (2) in a non-nucleophilic solvent; or (3) with excess amine and no solvent. With derivatives HOR$_d$ the 6-fluoro derivative 17 is required for satisfactory conversion of 17 to 18.

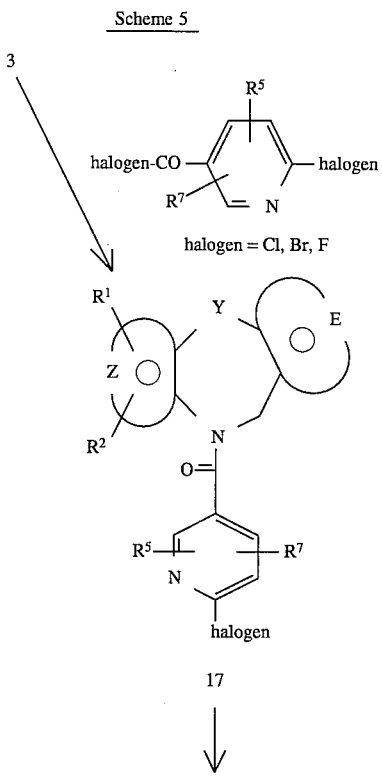

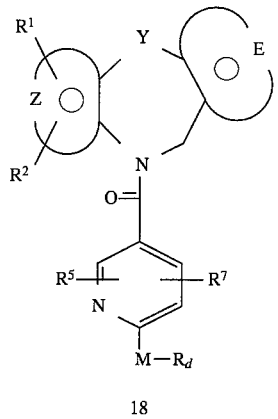

Alternatively, the products 18 may be prepared by first forming derivatives of the Formula 19 and then coupling these derivatives with the azepine compounds 3 (Scheme 6). The carboxylic acid intermediates are activated for coupling to the azepine compounds 3 by reaction with peptide coupling reagents, or preferably by conversion to the acid chlorides, anhydrides or mixed anhydrides.

Scheme 6

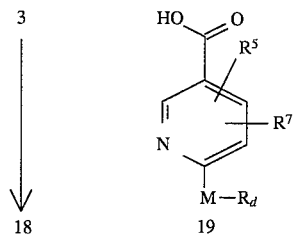

As an alternative method for synthesis of compounds of this invention as depicted in Formula I wherein $R_a$, $R_b$, $R^1$, $R^2$, $R^5$, $R^7$, A, and Y are as previously defined and $R^3$ is $$-\overset{O}{\underset{\|}{C}}-Ar$$

is the coupling of aryl carboxylic acids 20 with the azepine derivative 3. (Scheme 7)

The aryl carboxylic acids are activated for coupling by conversion to an acid chloride, bromide or anhydride or by first reacting with an activating reagent such as N,N-dicyclocarbodiimide, diethyl cyanophosphonate and related "peptide type" activating reagents. The method of activating the acids 20 for coupling to the azepine derivative 3 is chosen on the basis of compatibility with other substituent groups in the molecule. The method of choice is the conversion of the aryl carboxylic acid 20 to the corresponding aroyl chloride. The aryl acid chlorides 21 may be prepared by standard procedures known in the art, such as reaction with thionyl chloride, oxalyl chloride and the like. The coupling reaction is carried out in solvents such as halogenated hydrocarbons, toluene, xylene, tetrahydrofuran, dioxane in the presence of pyridine or tertiary bases such as triethylamine and the like (Scheme 7). Alternatively, the aroyl chlorides, prepared from the aryl carboxylic acids 20 may be reacted with derivatives 3 in pyridine with or without 4-(dimethylamino)pyridine to give derivatives 22.

In general, when the aryl carboxylic acids are activated with N,N-carbonyldiimidazole and other "peptide type" activating reagents, higher temperatures are required than when the aroyl chlorides are used. The reaction may be carried out in a higher boiling solvent xylene or without a solvent (100° C. to 150° C.).

The activation of aryl carboxylic by conversion to the acid chlorides with thionyl chloride or oxalyl chloride is preferred since the more reactive aroyl chlorides give better yields of product. The synthesis of selected examples is illustrated in Scheme 7.

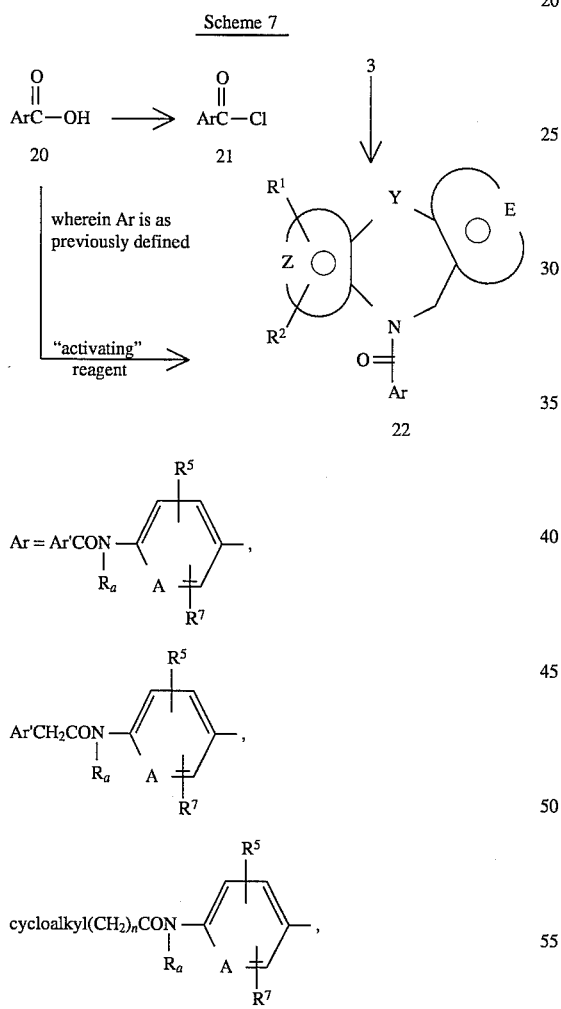

-continued
Scheme 7

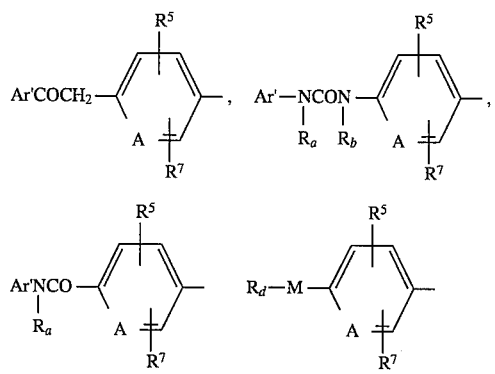

The synthesis of compounds of Formula I wherein $R^3$ is

the Ar group is

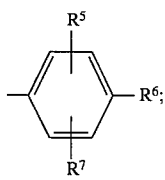

$R^6$ is

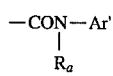

and where Ar' is as previously defined is carried out according to Scheme 8. The azepine compounds are reacted with mono-methyl terephythalyl chloride 23 (prepared from mono-methyl terephthalate and thionyl chloride) in the presence of a tertiary base such as triethylamine in solvents such as dichloromethane, tetrahydrofuran, dioxane, toluene and the like to give derivatives 24. These ester intermediates 24 are hydrolyzed with two to ten equivalents of an alkaline hydroxide such as potassium or sodium hydroxide in aqueous methanol or ethanol to give the corresponding acids after acidification and workup. The free acids are converted to the acid chlorides with thionyl chloride and these acid chloride intermediates 25, reacted with aminoaryl derivatives of formula:

    26 wherein Ar' and $R_a$ are as previously defined to give compounds 27.

Scheme 8

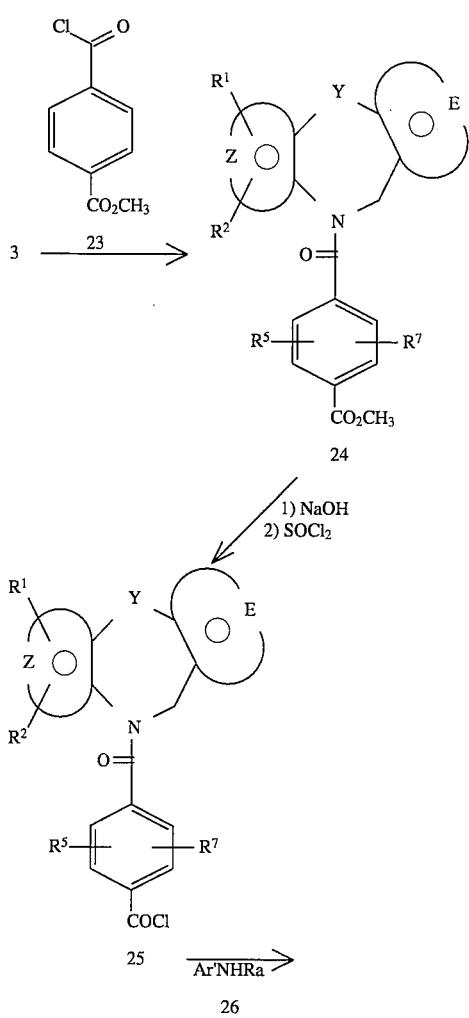

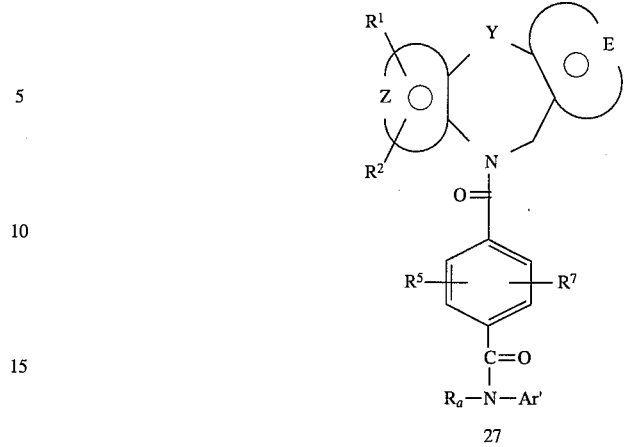

Certain of the tricyclic azepines as exemplified by compounds 33–35 are prepared through an initial ring closure of inter-mediate acyclic derivatives 30 followed by formation of the third ring through the use of literature procedures (Scheme 9). Ring closure of acyclic derivatives of structural type 30 wherein the nitrogen atom is pro-tected with a p-toluensulfonyl group may be ring closed to give the β-keto esters 31 which exist in the enol form as shown (structure 31). Decarboxylation gives intermediates 32 which by literature procedures are converted to the tosyl protected tricyclic azepines 33–35. The tosyl protecting group in the derivatives, as exemplified by tricyclic azepines 33–35, can be removed as described in the literature (P. P. Carpenter and M. Lennon, *J. Chem. Soc. Chem. Comm;* 665, 1979) for sulfonamide cleavage of benzazepine derivatives.

Scheme 9

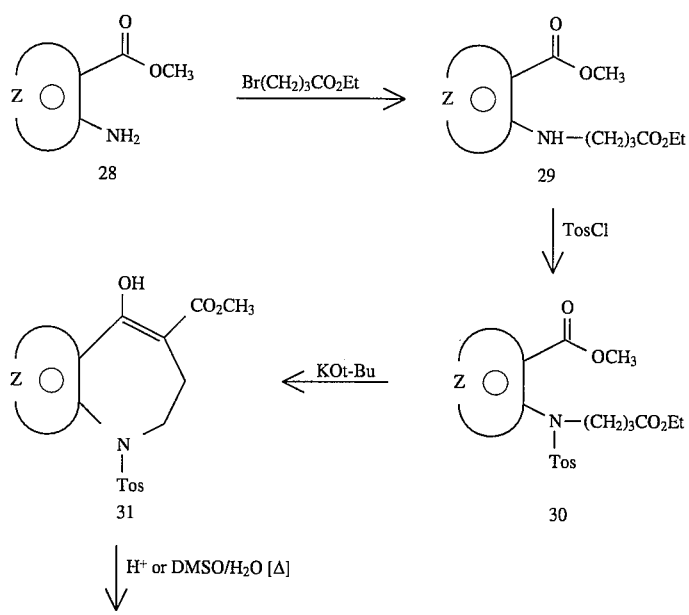

-continued
Scheme 9

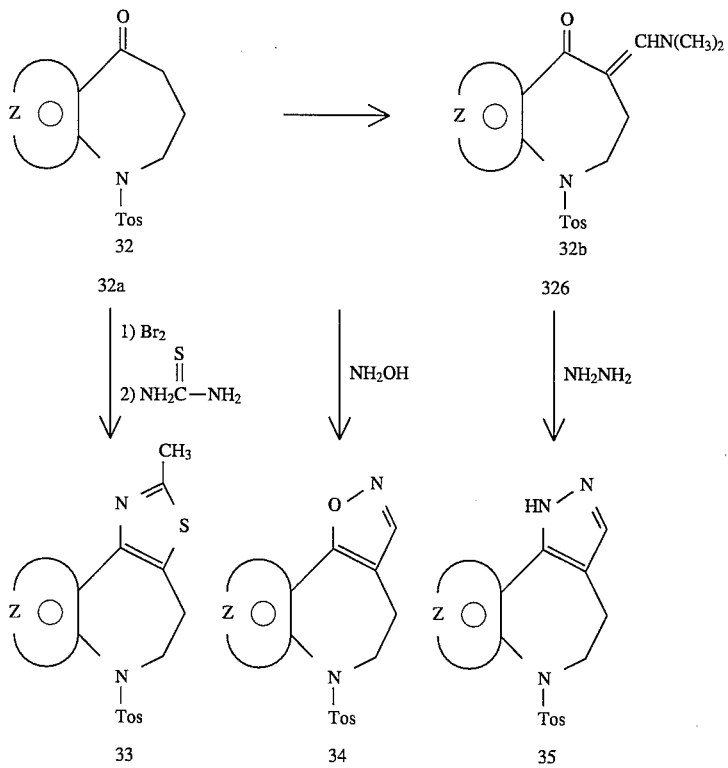

Certain intermediate azepines with a fused heterocyclic ring, as exemplified by structure 44, which are useful in preparing the intermediate tricyclic azepines necessary for the synthesis of the vasopressin-oxytocin antagonists of this invention may be prepared as illustrated in Scheme 10. Standard chemical reactions and conditions are used to convert the azepinones of structural type 44 into the tricyclic azepines of formulae 47–50 (via intermediates 45 and 46).

As shown in Scheme 10, expansion of a six-membered ring into a seven-membered lactam is carried out by reaction of the ketone derivative 36 with hydroxyl amine to give the oxime derivative which in most cases exists as a mixture of syn and anti forms (structures 37 and 38). The mixture of oximes on reaction with 4-methylbenzenesulfonyl chloride gives either a mixture of oxime O-tosylates or in some cases a single O-tosylate 39. Heating the oxime O-tosylates with potassium acetate in a alcohol-water mixture (such as ethanol-water or n-butanol-water) gives the 7-membered lactam derivatives 41. Reduction of the lactam with borane, or lithium aluminium hydride (LAH) affords the fused heterocyclic azepines 42. The azepines 42 may be converted to intermediates 43 and 44, which are useful in the preparation of the novel compound of this invention. As hereinbefore stated, the heterocyclic azepines of structural types illustrated by formulae 45–55 may be prepared by the methods exempli-fied in Scheme 10 or literature methods for ring closures to azepines.

Scheme 10
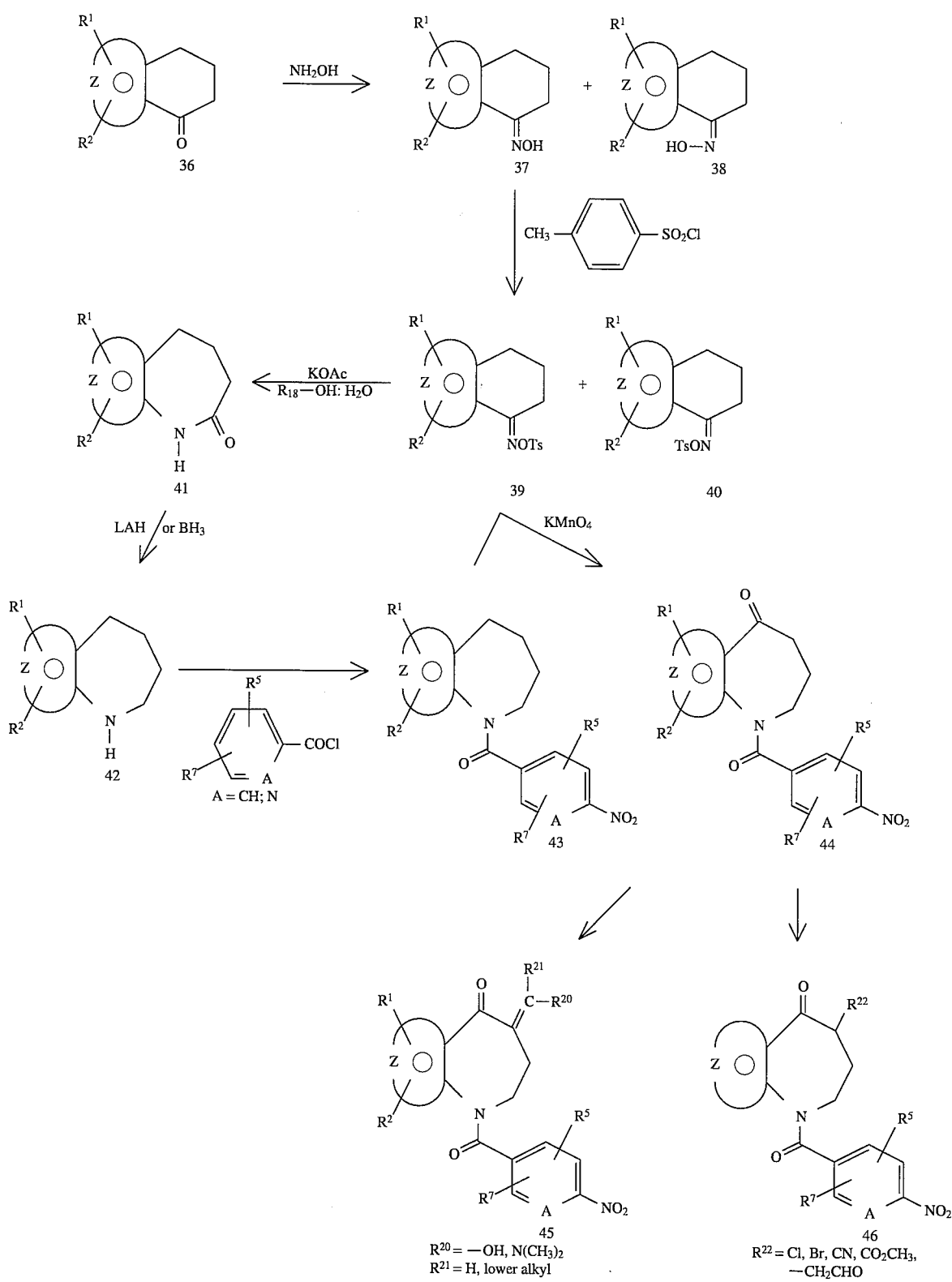

-continued
Scheme 10

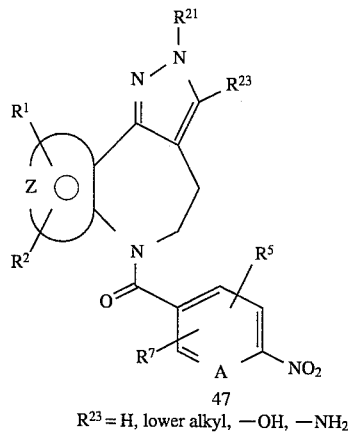
47
$R^{23}$ = H, lower alkyl, —OH, —NH$_2$

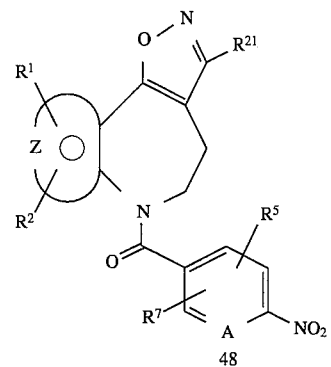
48

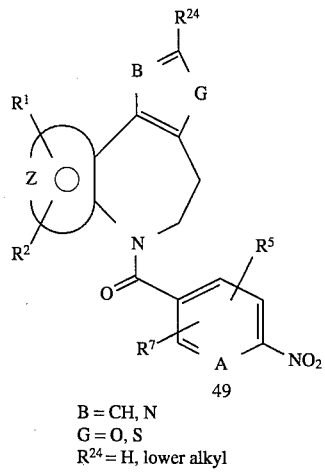
49
B = CH, N
G = O, S
$R^{24}$ = H, lower alkyl

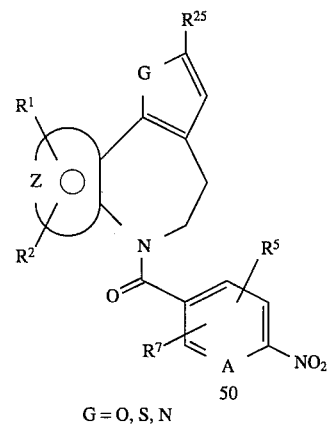
50
G = O, S, N
$R^{25}$ = lower alkyl, CO$_2$CH$_3$

Certain of the compounds of this invention wherein $R_a$ is as previously defined are prepared by introduction of the $R_a$ group either in a final step or in the penultimate step as shown in Scheme 11. In the derivatives 51 introduction of the $R_a$ substituent ($R_a$ not H) may be carried out in the final step by first forming the anion of the amide function of derivative 51 followed by the appropriate alkylation of the nitrogen atom to give products 52. In derivatives where protection-deprotection is needed the derivatives 51 are converted to the protected intermediates 52a and 52b which on deprotection afford compounds 52. The $R^{27}$ group may be a tertiary butoxy carbonyl group, an acetyl group or other known amine protecting moieties. The $R^{28}$ group may be a tertiary butylcarbonyl group, an acetyl group or other known hydroxy protecting moieties.

Scheme 11

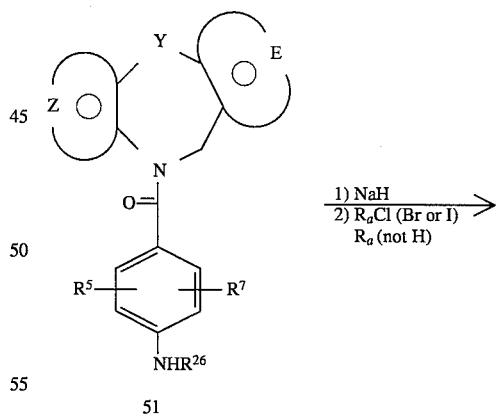
51

1) NaH
2) $R_a$Cl (Br or I)
$R_a$ (not H)

31
-continued
Scheme 11

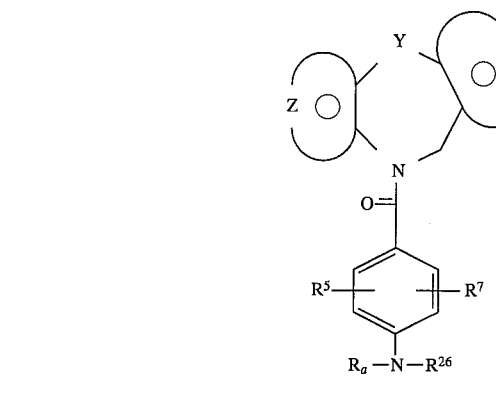

52

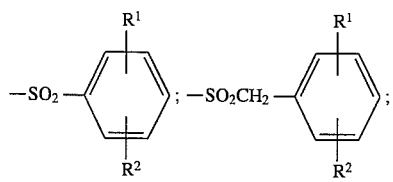

$R^{26}$ = —COAr'; —COCH$_2$Ar'; —CON(R$_c$)—Ar'; —CO(CH$_2$)$_n$cyclolalkyl; —COCHAr';

—SO$_2$—Ar(R$^1$,R$^2$); —SO$_2$CH$_2$—Ar(R$^1$,R$^2$);

—P(=O)[—O—Ar(R$^1$,R$^2$)]$_2$ ; —P(=O)[Ar(R$^1$,R$^2$)]$_2$ ;

—CO$_2$lower alkyl(C$_3$–C$_8$); —COlower alkyl(C$_3$–C$_8$);

—SO$_2$lower alkyl(C$_3$–C$_8$); —CO$_2$-lower alkenyl(C$_3$–C$_8$);

—COlower alkenyl(C$_3$–C$_8$); —SO$_2$lower alkenyl(C$_3$–C$_8$)

32
-continued
Scheme 11

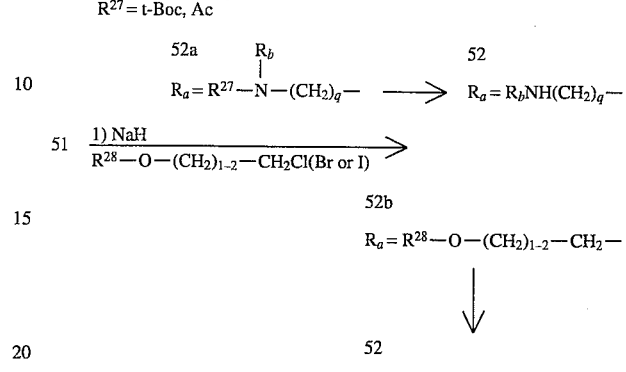

Compounds of this invention represented by the formula 59 may be prepared from the compounds represented by those of formula 58 as shown in Scheme 12. The 6-chloro, bromo or fluoro intermediate 17 is reacted with an amino derivative of the formula $R_aNH_2$ wherein $R_a$ is as hereinbefore defined to give compounds of the formula 58. Reaction of the 6-aminonicotinoyl derivative 58 with an $R^{26}$-chloride wherein $R^{26}$ is defined as shown in Scheme 12 affords compounds of this invention as exemplified by formula 59.

Scheme 12

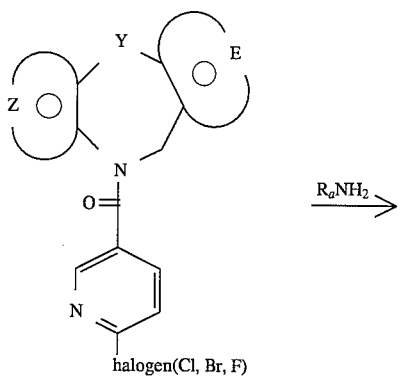

-continued
Scheme 12

$R^{26}$ = —COAr'; —COCH$_2$Ar'; —CONAr'$\overset{R_b}{|}$;

—CO(CH$_2$)$_n$cycloalkyl; —COCHAr'$\overset{|}{R_c}$

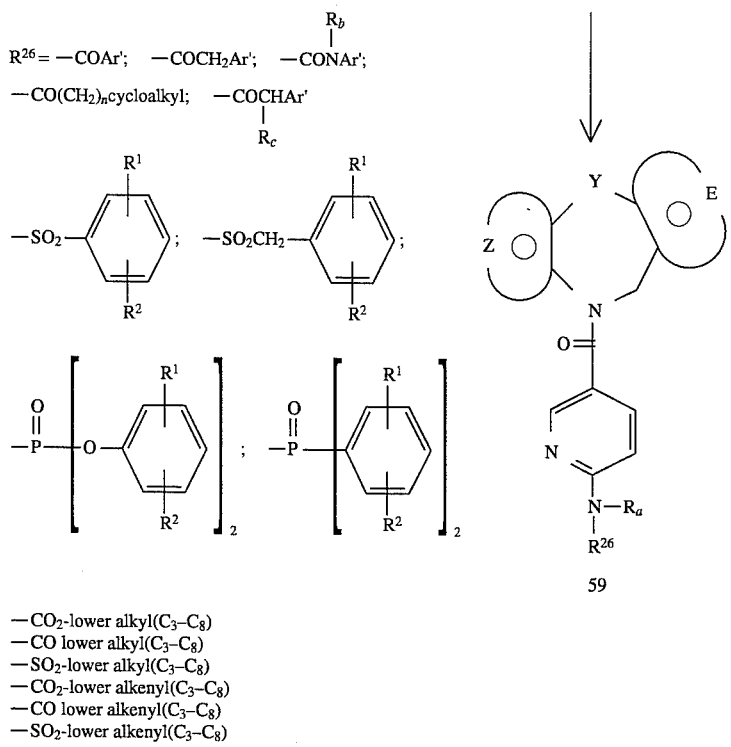

—CO$_2$-lower alkyl(C$_3$–C$_8$)
—CO lower alkyl(C$_3$–C$_8$)
—SO$_2$-lower alkyl(C$_3$–C$_8$)
—CO$_2$-lower alkenyl(C$_3$–C$_8$)
—CO lower alkenyl(C$_3$–C$_8$)
—SO$_2$-lower alkenyl(C$_3$–C$_8$)

REFERENCE EXAMPLE 1

6,7-Dihydrobenzo[b]thiophen-4(5H)-one, Oxime

To a solution of 4-keto-4,5,6,7-tetrahydrothionaphthene in 260 ml of ethanol is added 27.4 g of hydroxylamine hydrochloride. To the mixture is added 16.5 g of sodium acetate and 66 ml of water and then the mixture is refluxed for 3.5 hours; chilled in an ice bath and filtered. The solid is washed with water and ethanol to give 13 g of solid which is dried at 65° C. under vacuum to give 11.7 g of crystals, m.p. 124°–126° C. (mainly one isomer syn or anti). The filtrate is concentrated under vacuum and extracted with 250 ml of dichloromethane. The extract is washed with 100 ml each of water, brine and then dried (Na$_2$SO$_4$). The solvent is removed and the solid dried at 65° C. under vacuum to give 32 g of crystals, m.p. 106°–109° C. (mainly one isomer syn or anti).

REFERENCE EXAMPLE 2

6,7-Dihydrobenzo[b]thiophen-4(5H)-one, Oxime-O-tosylate

To a stirred solution of 12.2 g of 6,7-dihydrobenzo[b]thiophen-4(5H)-one, oxime (mixture of isomers) in 26 ml of dry pyridine is cooled to 0° C. is added 15.3 g of p-toluenesulfonyl chloride (all at once). After 5 minutes, a solid separates and the mixture is stirred at 0° C. for 1 hour. To the cold mixture is added 195 ml or 2N HCl and the mixture filtered to give a solid which is washed with water and dried (under vacuum) to give 21.5 g of product as crystals, m.p. 117°–120° C.

REFERENCE EXAMPLE 3

5,6,7,8-Tetrahydro-4H-thieno[3,2-b]blazepin-5-one

A mixture of 21.45 g of 6,7-dihydrobenzo[b]thiophen-4(5H)-one, oxime-O-tosylate, 136.1 g of potassium acetate, 528 ml of ethanol and 904 ml of water is refluxed for 22 hours. The mixture is concentrated under vacuum (to remove ethanol), chilled and filtered to give a solid. The solid is washed with water, dried (in air) and recrystallized by dissolving in hot ethyl acetate and diluting the solution with hexane. Chilling and filtering gives 7.1 g of crystals, m.p. 128°–132° C.

REFERENCE EXAMPLE 4

5,6,7,8-Tetrahydro-4H-thieno[3,2-b]azepine (1) To a mixture of 4.54 g of lithium aluminum hydride in 400 ml of dry tetrahydrofuran under argon is added dropwise a solution of 10.0 g of 5,6,7,8-tetrahydro-4H-thieno[3,2-b]azepin-5-one in 200 ml of tetrahydrofuran. After the addition, the mixture is heated at 45°–50° C. (exothermic reaction), and cooled to room temperature. The mixture is chilled in an ice bath (0° C.) and 4.5 ml of water added dropwise over 1 hour, followed by the dropwise addition of 4.5 ml of 2N sodium hydroxide and the dropwise addition of 14 ml of water. The mixture is filtered through diatomaceous earth and the filter cake washed with tetrahydrofuran. The filtrate is concentrated to give a solid. The solid is crystallized from hexane to give 5.5 g of off-white crystals, m.p. 66°–68° C.

(2) To a mixture of 21.2 g of 5,6,7,8-tetrahydro-4H-thieno [3,2-b]azepin-5-one in 100 ml of tetrahydrofuran under argon, chilled to 0° C. is added 25.2 ml of a 10.0 molar solution of borane-dimethylsulfide in tetrahydrofuran. The solution is stirred at room temperature for 16 hours and is refluxed for 5 hours. The mixture is cooled to room temperature and 85 ml of methanol added dropwise (exotherm). The solvent is removed and 100 ml of methanol is added (2 times) and after each addition the solvent is removed. To the residual solid (dried under vacuum) is added 126 ml of 2N NaOH and the mixture refluxed 3 hours. The mixture is chilled (2 hours) and extracted with dichloromethane. The extract is dried ($Na_2SO_4$) and the solvent removed to give 15.4 g of brown solid, m.p. 55°–57° C. A sample (3 g) is sublimed to give 2.6 g of crystals, m.p. 64°–65° C.

REFERENCE EXAMPLE 5

4-(4-Nitrobenzoyl)-5,6,7,8-tetrahydro-4H-thieno[3, 2-b]azepine

To a solution of 10.71 g of 5,6,7,8-tetrahydro-4H-thieno [3,2-b]azepine and 19.4 ml of triethylamine in 150 ml of dichloromethane under argon is added in small portions 4 -nitrobenzoyl chloride (exothermic). The mixture is stirred for 3 hours at 25° C. and then washed with water, sodium bicarbonate solution, brine and dried ($Na_2SO_4$). The solvent is removed, the residue dried under vacuum and recrystallized by dissolving in hot ethyl acetate and diluting with hexane. Chilling overnight and filtering gives 16 g of light brown crystals, m.p. 141°14 142° C.

REFERENCE EXAMPLE 6

4-(4-Nitrobenzoyl)-4,5,6,7-tetrahydro-8H-thieno[3, 2-b]azepin-8-one

To a solution of 9.0 g of 4-(4-nitrobenzoyl)-5,6,7,8-tetrahydro-4H-thieno[3,2-b]azepine in 713 ml of acetone is added 6.74 g of $MgSO_4$ and 351 ml of water followed by 8.2 g of $KMnO_4$ and heating at 70° C. for 18 hours. Another 6.24 g of $MgSO_4$ and 8.2 g of $KMnO_4$ is added and heating continued at 70° C. for 8 hours. An additional 6.24 g of $MgSO_4$ and 8.2 g of $KMnO_4$ is added and heating continued at 70° C. for 18 hours. The reaction mixture is filtered through diatomaceous earth and the cake washed with acetone and 500 ml of methylene chloride. The combined filtrates are evaporated in vacuo to a residue which is washed with water and air dried to give 5.7 g of a solid. The solid is crystallized from ethyl acetate to give 5.1 g of off white solid, m.p. 184°–186° C.

REFERENCE EXAMPLE 7

4-(4-Aminobenzoyl)-4,5,6,7-tetrahydro-8H-thieno[3, 2-b]azepin-8-one

To a mixture of 2.0 g of 4-(4-nitrobenzoyl)-4,5,6,7-tetrahydro-8H-thieno[3,2-b]azepin-8-one in 40 ml of glacial acetic acid is added 20 ml of 6N-hydrochloric acid. The mixture is cooled and 3.53 g of iron powder added in portions. The mixture is allowed to warm to room temperature and is heated at 70°–80° C. for 1 hour and then cooled to 0° C. To mixture is basified with 10N NaOH(pH 14) and extracted with 200 ml of ethyl acetate. The aqueous layer is again extracted with 200 ml of ethyl acetate and the extracts combined. The combined extract is washed with 100 ml each of $H_2O$ and brine and dried ($Na_2SO_4$). The extract is filtered through a thin pad of hydrous magnesium silicate and the filtrate concentrated to give a solid which is crystallized from ethyl acetate-hexane to give 1.24 g of crystals, m.p. 216°–218° C.

REFERENCE EXAMPLE 8

2-Chloro-4-(4-nitrobenzoyl)-5,6,7,8-tetrahydro-4H-thieno[3,2-b]azepine

A solution of 6.04 g of 4-(4-nitrobenzoyl)-5,6,7,8-tetrahydro-4H-thieno[3,2-b]azepine in 40 ml of tetrahydrofuran is cooled to 0° C. and 5.34 g of N-chlorosuccinimide added in portions. After the addition, the mixture is heated at 70° C. overnight. The mixture is concentrated, diluted with 300 ml of dichloromethane and the mixture washed with 100 ml each of saturated $K_2CO_3$ solution, $H_2O$, 1N HCl and brine. The organic layer is dried ($Na_2SO_4$) and filtered through a thin pad of hydrous magnesium silicate. The filtrate is concentrated and the residue chromatographed by HPLC on silica gel (2-columns) with a Waters-Prep-500 instrument and the solvent system ethyl acetate-dichloromethane (1:1) containing 2% diethylether. The middle cuts are combined and concentrated to give 0.135 g of 2,3-dichloro-4-(4-nitrobenzoyl)-5,6,7,8 -tetrahydro-4H-thieno[3,2-b]azepine, m.p. 140°–142° C. The latter cuts are combined, concentrated and the residue crystallized from ethyl acetate-hexane to give 2.8 g of crystals, 119°–120° C.

REFERENCE EXAMPLE 9

2-Chloro-4-(4-nitrobenzoyl)-4,5,6,7-tetrahydro-8H-thieno[3,2-b]azepin-8-one

To a stirred solution of 0.336 g of 2-chloro-4-(4-nitrobenzoyl)-4,5,6,7-tetrahydro-4 H-thieno[3,2-b]azepine in 36 ml of acetone-water (2:1) is added 0.21 g of anhydrous magnesium sulfate and 0.275 g of potassium permanganate. The mixture is heated at 70° C. overnight. An additional 0.275 g of potassium permanganate and 0.21 g of magnesium sulfate is added and the mixture heated at 70° C. for 6 hours. An additional 0.275 g of potassium permanganate and 0.21 g of magnesium sulfate is added and the mixture stirred and heated at 70° C. for 24 hours. The hot mixture is filtered and the filtrate evaporated. The residue is heated in a few ml of ethyl acetate, cooled and filtered to give 0.20 g of product as a solid. The reaction is repeated on 10 times the scale to give 1.3 g of off-white crystals, m.p. 165°–168° C.

REFERENCE EXAMPLE 10

Methyl 4-[2-(2-chlorophenyl)-2-cyano-2-(4-morpholinyl)ethyl]benzoate

A 0.876 g sample of 60% sodium hydride in oil is washed with hexane followed by the addition of 60 ml of dry N,N-dimethylformamide. The reaction mixture is stirred for 1 hour under argon at room temperature after the addition of 4.73 g of α-(2-chlorophenyl)-4-morpholineacetonitrile. To the reaction mixture is added 4.58 g of methyl 4-(bromomethyl)benzoate and stirring continued for 3 hours. Several drops of acetic acid is added to ice water and the reaction quenched. The pH is 3–4 and saturated NaHCO$_3$ added to adjust the pH to 6–7. Upon cooling a solid forms which is filtered, washed with water and dried to give 5.92 g of yellow solid. Crystallization from methylene chloride-hexane gives 2.10 g of the desired product as a crystalline solid, m.p. 116°–118° C.

REFERENCE EXAMPLE 11

Methyl 4-[2-(2-chlorophenyl)-2-oxoethyl]benzoate

A mixture of 1.0 g of methyl[4-(2-chlorophenyl)-2-cyano-2-(4-morpholinyl)ethyl]benzoate and 14 ml of acetic acid and 6 ml of water is heated at reflux for 20 minutes then poured over crushed ice. After stirring for 15 minutes, the resulting solid is collected, washed with water and air dried to give 0.63 g of tan solid, m.p. 40°–42° C.

REFERENCE EXAMPLE 12

4-[2-(2-Chlorophenyl)-2-oxoethyl]benzoic acid

A mixture of 18.78 g of methyl 4-[2-(2-chlorophenyl)-2-oxoethyl]benzoate in 288.8 ml of CH$_3$OH, 72.2 ml of water and 5.2 g of NaOH is refluxed for 3 hours then acidified with 2N citric acid. The reaction mixture is evaporated in vacuo to remove the CH$_3$OH. The aqueous phase is extracted with CH$_2$Cl$_2$ and acidified with 1N HCl. The resulting solid is collected and dried under vacuum to give 17.27 g of the desired product, m.p. 168°–172° C.

REFERENCE EXAMPLE 13

Methyl 4,5,6,7-tetrahydro-4-oxo-3-benzofurancarboxylate

To a solution of 2.11 g of 4-oxo-4,5,6,7tetrahydrobenzo[b]furan-3-carboxylic acid in 100 ml of methanol is added 202 mg of p-toluenesulfonic acid hydrate and the mixture heated at reflux for 24 hours. The reaction mixture is cooled to room temperature and the methanol concentrated in vacuo to a residue. The residue is dissolved in 100 ml of ethyl acetate and washed with 30 ml of saturated sodium bicarbonate and 30 ml of brine. The organic layer is dried with Na$_2$SO$_4$, filtered and the filtrate concentrated in vacuo to a residue which is crystallized from ethyl acetate-hexane to give 1.75 g of the desired product as a white crystalline solid, m.p. 100°–102° C.

REFERENCE EXAMPLE 14

Methyl 5,6,7,8-tetrahydro-5-oxo-4H-furo[3,2-b]azepine-3-carboxylate

To a mixture of 1.0 g of methyl 4,5,6,7-tetrahydro-4-oxo-3-benzofurancarboxylate and 502 mg of sodium azide in 5 ml of chloroform is added dropwise at 32°–36° C. under argon 1.4 ml of sulfuric acid. The reaction mixture is stirred at room temperature for 24 hours. The reaction mixture is diluted with 14 ml of water and rendered alkaline with NH$_4$OH and extracted with chloroform. The separated organic layer is washed with water, brine and dried with Na$_2$SO$_4$ and concentrated in vacuo to give 1.0 g of the desired product as a white solid.

REFERENCE EXAMPLE 15

(E) 4,5,6,7-Tetrahydro-4-[[[(4-methylphenyl)sulfonyl]oxy]imino]-3-benzofurancarboxylic acid To a partial solution of 2.8 g of (E)-4,5,6,7-tetrahydro-4-(hydroxyimino)-3-benzofurancarboxylic acid in 7 ml of pyridine is added portionwise at 0° C., 3.01 g of p-toluene sulfonyl chloride under argon. The mixture is stirred for 1 hour then diluted with 40 ml of cold 1N HCl, filtered, washed with water and dried with Na$_2$SO$_4$. The filtrate is concentrated in vacuo to give 4.78 g of the desired product as an off-white solid, m.p. 155°–165° C.

REFERENCE EXAMPLE 16

5,6,7,8-Tetrahydro-5-oxo-4H-furo[3,2-b]azepine-3-carboxylic acid

A mixture of 1.0 g of (E)-4,5,6,7-tetrahydro-4-[[[(4-methylphenyl)sulfonyl]oxy]imino]-3 -benzofurancarboxylic acid, 5.9 g of potassium acetate, 23 ml of ethanol and 39 ml of water is heated at reflux for 48 hours. The reaction mixture is concentrated in vacuo, 80 ml of methylene chloride added and the separated organic layer washed with water, brine and dried with Na$_2$SO$_4$. The organic layer is concentrated in vacuo to a solid which is purified by chromatography on a preparative silica gel plate by elution with 0.5% acetic acid in ethyl acetate. The eluted band is washed with 1% acetic acid in ethyl acetate. The organic layer is dried with Na$_2$SO$_4$ and concentrated in vacuo to give 200 mg of off-white solid which is crystallized from ethyl acetate-hexane to give 165 mg of the desired product as a white solid.

REFERENCE EXAMPLE 17

(E) and (Z)-4,5,6,7-Tetrahydro-4-(hydroxyimino)-3-benzofurancarboxylic acid

To a solution of 30.0 g of 4,5,6,7-tetrahydro-4-oxo-3-benzofurancarboxylic acid in 225 ml of ethanol is added 22.97 g of hydroxylamine hydrochloride, followed by 18.10 g of sodium acetate and 55 ml of water. The reaction mixture is heated at reflux for 2.5 hours and concentrated in vacuo to a residue which is diluted with 600 ml of ethyl acetate, washed with 2×200 ml of water, brine and dried over Na$_2$SO$_4$. The organic layer is concentrated in vacuo to a residue which is dried under vacuum to give 31.0 g of the desired product as a solid.

REFERENCE EXAMPLE 18

(E) and (Z)-6,7-Dihydro-4-(5H)benzofuranone, O-[(4-methylphenyl)sulfonyl]oxime

To a partial solution of 28.0 g of (E) and (Z)-4,5,6,7-tetrahydro-4-(hydroxyimino)benzofuran in 54 ml of pyridine is added portionwise at 0° C., 38.8 g of p-toluene sulfonyl chloride under argon. The mixture is stirred for 1 hour then diluted with 600 ml of ethyl acetate and 400 ml of cold 2N HCl. The organic layer is washed with 200 ml of water and 200 ml of brine, and dried with Na$_2$SO$_4$. The filtrate is concentrated in vacuo to give 50 g of the desired product as a solid. Crystallization from ethyl alcohol by allowing to stand at room temperature gives 19.9 g of off-white needles, m.p. 123°–125° C. The filtrate is allowed to stand and the crystals collected and dried to give 10.0 g of the desired product as an off-white solid, 83°–85° C.

REFERENCE EXAMPLE 19

4-(2-Chloro-4-nitrobenzoyl)-5,6,7,8-tetrahydro-4H-thieno[3,2-b]azepine

To a solution of 15.0 g of 5,6,7,8-tetrahydro-4H-thieno [3,2-b]azepine in 150 ml of dichloromethane cooled to 0° C. is added 27.2 ml of triethylamine. After stirring 5 minutes, a solution of 28.0 g of 2-chloro-4-nitrobenzoyl chloride in 140 ml of dichloromethane is added slowly. The solution is stirred at room temperature overnight, diluted with 450 ml of dichloromethane and the solution washed with 200 ml each of water, 2N citric acid, 1M sodium bicarbonate and brine. The organic layer is dried over $Na_2SO_4$, filtered through a thin pad of hydrated magnesium silicate and the filtrate concentrated under vacuum. The residue is crystallized from ethyl acetate to give 24.3 g of off-white crystals, m.p. 131°–134° C.

REFERENCE EXAMPLE 20

4-(2-Chloro-4-nitrobenzoyl)-4,5,6,7-tetrahydro-8H-thieno[3,2-b]azepine-8-one

To a solution of 2.02 g of 4-(2-chloro-4-nitrobenzoyl)-4, 5,6,7,8-tetrahydro-4H-thieno[3,2-b]azepine in 144 ml of acetone is added 1.56 g of magnesium sulfate, 72 ml of water and 1.89 g of potassium permanganate. The mixture is stirred and heated at 70°–75° C. for 4 hours. An additional amount of magnesium sulfate (1.56 g) and potassium permanganate (1.89 g) is added and the mixture stirred and heated at 75° C. for 16 hours. Magnesium sulfate (1.56 g) and potassium permanganate (1.89 g) are added and the mixture stirred and heated at 75° C. for 5 hours. The mixture is filtered through diatomaceous earth and the filter cake washed with acetone and dichloromethane The filtrate is concentrated and the residue (1.4 g) is heated with ethyl acetate, the mixture (with insoluble solid) cooled and filtered to give 1.0 g of product as a solid. The solid is washed with water and dried to give crystals, m.p. 180°–185° C.

REFERENCE EXAMPLE 21

5-Fluoro-2-methylbenzoyl chloride

A mixture of 8.0 g of 5-fluoro-2-methylbenzoic acid and 52 ml of thionyl chloride is heated on a steam bath for 1 hour. The volatiles are removed under vacuum and two times 50 ml of toluene is added and the solvent removed under vacuum to give 8.5 g of product as a gum.

REFERENCE EXAMPLE 22

2-Chloro-5-(methylthio)benzoyl chloride

A mixture of 2.03 g of 2-chloro-5-(methylthio)benzoic acid and 10 ml of thionyl chloride is heated on a steam bath for 1 hour. The volatiles are removed under vacuum and 20 ml of toluene added and removed under vacuum (2 times) to give 2.2 g of brown needles.

REFERENCE EXAMPLE 23

2-Chloro-4-nitrobenzoyl chloride

As described for Reference Example 21, 25 g of 2-chloro-4-nitrobenzoic acid is reacted with thionyl chloride (124 ml) to give the product (27.0 g) as a brown oil.

REFERENCE EXAMPLE 24

2-Chloro-5-nitrobenzoyl chloride

As described for Reference Example 21, 5.0 g of 2-chloro-5-nitrobenzoic acid is reacted with 50 ml of thionyl chloride to give 5.6 g of the product as an off-white solid.

REFERENCE EXAMPLE 25

2,3-Dimethylbenzoyl chloride

As described for Reference Example 21, 3.0 g of 2,3-dimethylbenzoic acid is reacted with 40 ml of thionyl chloride to give 3.2 g of the product as a colorless oil.

REFERENCE EXAMPLE 26

2-Chlorobenzoyl chloride

As described for Reference Example 21, 3.13 g of 2-chlorobenzoic acid is reacted with 40 ml of thionyl chloride to give 3.32 of product as an off-white semi solid.

REFERENCE EXAMPLE 27

4-[(2-Methylbenzoyl)amino]benzoic acid

A mixture of 43.42 g (0.26 mol) of ethyl 4-aminobenzoate and 40.8 g (0.26 mol) of 2-methylbenzoyl chloride in 150 ml of dichloromethane is cooled in an ice bath and 26.56 g (0.26 mol) of triethylamine is added dropwise. After the addition, the solution is stirred at room temperature overnight. The mixture is poured into water and the organic layer separated. The organic layer is washed with water, 1N HCl, 1M $NaHCO_3$ and dried ($Na_2SO_4$). The solvent is removed and the solid slurried with ethyl acetate and filtered to give 57 g of ethyl 4-[(2-methylbenzoyl)amino]benzoate as crystals, m.p. 110°–115° C.

A mixture of 50.7 g (0.20 mol) of the preceding compound, 280 ml of ethanol and 55 ml of 10N NaOH is refluxed for 5 minutes. The mixture is cooled to room temperature, diluted with 200 ml of water and acidified with concentrated hydrochloric acid (pH 1–2). The mixture is filtered and the solid washed with water and dried to give 51 g of product as white crystals, m.p. 270°–275° C.

REFERENCE EXAMPLE 28

4-[(2-Methylbenzoyl)amino]benzoyl chloride

A mixture of 10.3 g of 4-[(2-methylbenzoyl)amino]benzoic acid and 32 ml of thionyl chloride is refluxed for 1.5 hours. The solution is concentrated under vacuum. Toluene is added and the solvent removed under vacuum. Toluene is added and the mixture chilled and filtered to give a yellow solid, m.p. 135°–141° C.

REFERENCE EXAMPLE 29

4-[(2,6-Dimethoxybenzoyl)amino]benzoic acid

A mixture of 2 g (10 mmol) of 2,6-dimethoxybenzoyl chloride, 1.65 g (10 mmol) of ethyl 4-aminobenzoate, 1.11 g of triethylamine and 61 mg of 4-dimethylaminopyridine in 10 ml of dichloromethane is refluxed for 20 hours. The mixture is diluted with water and the organic layer separated. The organic layer is washed with water, 1N HCl, 1N $Na_2CO_3$, brine and dried ($Na_2SO_4$). The solvent is removed to give a solid which is crystallized from ethyl acetate to give 1.22 g of ethyl 4-[(2,6-dimethoxybenzoyl)amino]benzoate as crystals, m.p. 183°–185° C.

A mixture of 3.88 g (11.79 mmol) of the preceding compound, 17.3 ml of 2N NaOH and 20 ml of methanol is stirred at room temperature overnight. Methanol (30 ml) and water (10 ml) are added and the solution refluxed for ½ hour. The solvents are removed under vacuum and the residual solid triturated with ether and the ether decanted. The solid is dissolved in 30 ml of water and acidified with 2N HCl (pH 3). The mixture is filtered, the solid washed with water and dried at 60° C. under vacuum to give 3.0 g of solid, m.p. 236°–240° C.

REFERENCE EXAMPLE 30

Ethyl 4-[(4-pyridinylcarbonyl)amino]benzoic acid

To a cooled mixture of 1.78 g (0.01 mol) of isoniconinoyl chloride hydrochloride in 5 ml of dichloromethane is added 2.52 g (0.025 mol) of triethylamine. To the solution is added a solution of 1.65 g of ethyl 4-aminobenzoate in 5 ml of dichloromethane. After stirring at room temperature overnight, 50 mg of 4-dimethylaminopyridine is added and the mixture is refluxed for 24 hours. The mixture is poured into water and filtered to give 3.4 g of brown solid. A 0.50 g sample is triturated with ethyl acetate to give 0.37 g of ethyl 4-[(4-pyridinylcarbonyl)amino]benzoate as yellow crystals, m.p. 143°–145° C.

REFERENCE EXAMPLE 31

2-Methylfurane-3-carbonyl chloride

A mixture of 4.0 g of methyl-2-methylfurane-3-carboxylate, 30 ml of 2N NaOH and 15 ml methanol is refluxed for 1.5 hours. The solvent is removed under vacuum to give a solid. The solid is extracted with dichloromethane (discarded). The solid is dissolved in water and the solution acidified with 2N citric acid to give a solid. The solid is washed with water and dried to give crystals 1.05 g of crystals of 2-methylfuran-3-carboxylic acid. The preceding compound (0.95 g) and 3 ml of thionyl chloride is refluxed for 1 hour. The solvent is removed, toluene added (20 ml, three times) and the solvent removed to give the product as an oil.

REFERENCE EXAMPLE 32

4-[N-Methyl-N-(2-methylbenzoyl)amino]benzoic acid

A sample of 1.51 g of sodium hydride (60% in oil) is washed with hexane under argon to remove the oil. To the washed sodium hydride is added 5 ml of N,N-dimethylformamide. To this mixture is added dropwise a solution of 8.69 g of ethyl 4-[(2-methylbenzoyl)amino]benzoate in 20 ml of dimethylformamide. The mixture is stirred at room temperature for 0.5 hour and then 5.23 g of methyl iodide is added. The mixture is stirred at room temperature for 16 hours. The mixture is diluted with water and extracted with dichloromethane. The extract is dried ($Na_2SO_4$), concentrated to reduce the volume and the solution filtered through a thin pad of hydrous magnesium silicate. The filtrate is concentrated in vacuo to give 11 g of an oil (1:1 mixture of product and N,N-dimethylformamide). The preceding product, ethyl 4-[N-methyl-N-(2-methylbenzoyl)amino]benzoate, (11 g) is dissolved in 30 ml of methanol and 25 ml of 2N NaOH added. The mixture is refluxed for 2 hours and the solvent removed. The residue is extracted with ether (discard) and the remaining residue dissolved in 50 ml of water. The basic solution is acidified with 2N citric acid and the solid filtered off and washed with water. The product is air dried to give 6.72 g of crystals, m.p. 187°–190° C.

REFERENCE EXAMPLE 33

4-[N-Methyl-N-[(2-methylbenzoyl)amino]benzoyl chloride

A solution of 6.72 g of 4-[N-methyl-N-(2-methylbenzoyl)amino]benzoic acid in 20 ml of thionyl chloride is refluxed for one hour. The volatiles are removed in vacuo. Toluene is added to the residue and then the toluene removed in vacuo (repeated several times) to give the 7.3 g of product as a brown oil.

As described for Reference Example 32, but substituting the appropriate ethyl 4-[(N-aroyl)amino]benzoate, the following compounds are prepared.

REFERENCE EXAMPLE 34

4-[N-Methyl-N-(2-chlorobenzoyl)amino]benzoic acid

REFERENCE EXAMPLE 35

N-[N-Methyl-N-(2,5-dichlorobenzoyl)amino]benzoic acid

REFERENCE EXAMPLE 36

N-[N-Methyl-N-(2,4-dichlorobenzoyl)amino]benzoic acid

REFERENCE EXAMPLE 37

4-[N-Methyl-N-(2-chloro-4-methylbenzoyl)amino]benzoic acid

REFERENCE EXAMPLE 38

4-[N-methyl-N-(2-methyl-4-chlorobenzoyl)amino]benzoic acid

REFERENCE EXAMPLE 39

4-[N-Methyl-N-(2,4-dimethylbenzoyl)amino]benzoic acid

REFERENCE EXAMPLE 40

4-[N-Methyl-N-(2,3-dimethylbenzoyl)amino]benzoic acid

REFERENCE EXAMPLE 41

4-[N-Methyl-N-(2-methoxybenzoyl)amino]benzoic acid

REFERENCE EXAMPLE 42

4-[N-Methyl-N-(2-trifluoromethoxybenzoyl)amino]benzoic acid

REFERENCE EXAMPLE 43

4-[N-Methyl-N-(2,4-dimethoxybenzoyl)amino]benzoic acid

REFERENCE EXAMPLE 44

4-[N-Methyl-N-(2-methoxy-4-chlorobenzoyl)amino]benzoic acid

REFERENCE EXAMPLE 45

4-[N-Methyl-N-(2-methylthiobenzoyl)amino]benzoic acid

REFERENCE EXAMPLE 46

4-[N-Methyl-N-(2-methylthiophen-3-ylcarbonyl)amino]benzoic acid

REFERENCE EXAMPLE 47

4-[N-Methyl-N-(3-methylthiophene-2-ylcarbonyl)amino]benzoic acid

REFERENCE EXAMPLE 48

4-[N-Methyl-N-(2-methylfuran-3-ylcarbonyl)amino]benzoic acid

REFERENCE EXAMPLE 49

4-[N-Methyl-N-(3-methylfuran-2-ylcarbonyl)amino]benzoic acid

REFERENCE EXAMPLE 50

4-[N-Methyl-N-(phenylacetyl)amino]benzoic acid

REFERENCE EXAMPLE 51

4-[N-Methyl-N-(2-chlorophenylacetyl)amino]benzoic acid

REFERENCE EXAMPLE 52

4-[N-Methyl-N-(2-methoxyphenylacetyl)amino]benzoic acid

REFERENCE EXAMPLE 53

4-[N-Methyl-N-(2-methylphenylacetyl)amino]benzoic acid

REFERENCE EXAMPLE 54

4-[N-Methyl-N-(cyclohexylcarbonyl)amino]benzoic acid

REFERENCE EXAMPLE 55

4-[N-Methyl-N-(3-cyclohexenecarbonyl)amino]benzoic acid

REFERENCE EXAMPLE 56

4-[N-Methyl-N-(cyclohexylacetyl)amino]benzoic acid

REFERENCE EXAMPLE 57

7,8-Dihydro-5(6H)quinolinone

A mixture of 57.93 g of 3-amino-2-cyclohexene-1-one, 76.8 g of 3-(dimethylamino)acrotein, 62.5 ml of glacial acetic acid and 270 ml of toluene is refluxed under argon for 16 hours and concentrated under vacuum to dryness. Toluene (200 ml) is added and the solvent removed under vacuum. To the residue is added one liter of dichloromethane and then 200 ml of saturated NaHCO$_3$ slowly added and solid NaHCO$_3$ added to bring the pH to 8. The mixture is filtered and the CH$_2$Cl$_2$ layer separated. The CH$_2$Cl$_2$ layer is passed through a thin pad of hydrous magnesium silicate and the filtrate concentrated to dryness. The residual black oil is extracted with hot hexane and the hexane decanted. This process is repeated until no more product extracted into the hexane. The hexane extracts are combined and the solvent removed to give 17.3 g of product as an oil.

REFERENCE EXAMPLE 64

7,8-Dihydro-5(6H)quinolinone, oxime

To a solution of 3.78 g of 7,8-dihydro-5(6H)quinolone in 20 ml of ethanol is added 2.68 g of hydroxylamine, hydrochloride, 3.23 g of sodium acetate and 5 ml of water. The mixture is refluxed under argon for 4.5 hours, cooled and filtered. The solid is washed with 30 ml of ethanol-water (1:1) and dried under vacuum to give 3.58 g of solid, m.p. 232°–236° C. Recrystallization from ethanol gives crystals, m.p. 234°–236° C.

REFERENCE EXAMPLE 65

7,8-Dihydro-5(6H)quinolinone, O-[(4-methylphenyl)sulfonyl]oxime

To a mixture of 2.30 g of 7,8-dihydro-5(6H)quinolinone, oxime, 3.59 g of 4-methylphenylsulfonyl chloride in 32 ml of acetone is added a solution of 0.84 g of potassium hydroxide in 10 ml of water. The mixture is refluxed for 0.5 hour under argon and the volatiles removed under vacuum. Water is added to the residue and the mixture is filtered and the solid washed with water and 1N $NaHCO_3$. The solid is dissolved in dichloromethane, dried and the solvent removed to give 3.83 g of solid. Recrystallization from diethyl ether gives crystals, m.p. 102°–104° C.

REFERENCE EXAMPLE 66

5,7,8,9-Tetrahydro-6H-pyrido[3,2-b]azepin-6-one

A mixture of 8.26 g of 7,8-dihydro-5(6H)-quinolinone, O-[(4-methylphenyl)sulfonyl]oxime, 54.63 g of potassium acetate, 193 ml of ethanol and 354 ml of water is refluxed for 20 hours. The mixture is concentrated under vacuum to remove volatiles and the aqueous residue (contains solid) is added chloroform. The mixture is filtered through diatomaceous earth, the filter pad washed with chloroform and the filtrate concentrated to dryness. The residual solid is recrystallized from acetone to give 2.81 g of crystals, m.p. 156°–159° C.

REFERENCE EXAMPLE 67

6,7,8,9-Tetrahydro-5H-pyrido[3,2-b]azepine

A mixture of 1.56 g of 5,7,8,9-tetrahydro-6H-pyrido[3,2-b]azepine-6-one, 3.31 g of lithium aluminum hydride in 40 ml of tetrahydrofuran is refluxed for 4 hours. The mixture is cooled (0° C.) and 25 ml of methanol is added dropwise. The mixture is filtered through diatomaceous earth, the filter cake washed with tetrahydrofuran and the filtrate concentrated to dryness under vacuum. Water (50 ml) is added to the residue and the mixture extracted with diethyl ether. The extract is dried ($Na_2SO_4$) and filtered through a thin pad of hydrous magnesium silicate (pad washed with) diethyl ether. The filtrate is concentrated under vacuum to give 1.01 g of crystals, m.p. 70°–71° C.

REFERENCE EXAMPLE 68

6,7,8,9-Tetrahydro-5-(2-chloro-4-nitrobenzoyl)-5H-pyrido[3,2-b]azepine

To a mixture of 2.90 g of 6,7,8,9-tetrahydro-5H-pyrido[3,2-b]azepine, 2.37 g of triethylamine in 40 ml of dichloromethane is added 5.16 g of 2-chloro-4-nitrobenzoyl chloride in 50 ml of dichloromethane. The mixture is stirred at room temperature under argon for 3 hours and then poured into water. The organic layer is separated and washed with 1N $NaHCO_3$, $H_2O$, brine and dried ($Na_2SO_4$). The solution is filtered through a thin pad of hydrous magnesium silicate, the pad washed with $CH_2Cl_2$ and ethyl acetate and the filtrate concentrated to dryness. The residual solid (7.13 g) is triturated with ethyl acetate to give 4.41 g of off-white crystals, m.p. 143°–145° C.

REFERENCE EXAMPLE 69

6,7,8,9-Tetrahydro-5-(4-amino-2-chlorobenzoyl)-5H-pyrido[3,2-b]azepine

A mixture of 3.31 g of 6,7,8,9-tetrahydro-5-(2-chloro-4-nitrobenzoyl)-5H-pyrido[3,2-b]azepine and 6.78 g of stannus chloride dihydrate ($SnCl_2.2H_2O$) in 200 ml of methanol is refluxed for 2 hours under argon. The solvent is removed under vacuum and 5 ml of saturated $NaHCO_3$ solution and solid $NaHCO_3$ added to bring the pH to 7. The mixture is extracted with ethyl acetate, the extract filtered through diatomaceous earth and the filtrate washed with saturated $NaHCO_3$, $H_2O$, brine and dried ($Na_2SO_4$). The filtrate is passed through a thin pad of hydrous magnesium silicate and the filtrate concentrated to dryness to give 2.58 g of an amorphous solid. Anal. Calc'd for $C_{16}H_{16}ClN_3O$; C,59.9; H,5.7; N,13.1; $C_{1,11.1}$ Found: C,60.5; H,5.0; N,12.9; Cl,11.6.

REFERENCE EXAMPLE 70

Methyl 6-aminopyridine-3-carboxylate

Dry methanol (400 ml) is cooled in an ice bath and HCl gas is bubbled into the mixture for 25 minutes. To the MeOH—HCl is added 30 g of 6-aminopyridine-3-carboxylic acid and then the mixture is stirred and heated at 90° C. for 2 hours (all the solid dissolved). The solvent is removed under vacuum and the residual solid dissolved in 100 ml of water. The acidic solution is neutralized with saturated sodium bicarbonate (solid separated) and the mixture chilled and filtered to give 30 g of white crystals, m.p. 150°–154° C.

REFERENCE EXAMPLE 71

6-[(5-fluoro-2-methylbenzoyl)amino]pyridine-3-carboxylic acid

To a mixture of 4.5 g of methyl 6-aminopyridine-3-carboxylate and 5.53 ml of triethylamine in 40 ml of dichloromethane (cooled in an ice bath) is added 6.38 g of 5-fluoro-2-methylbenzoyl chloride in 10 ml of dichloromethane. The mixture is stirred at room temperature under argon for 18 hours and an additional 3.4 g of 5-fluoro-2-methylbenzoyl chloride added. After stirring at room temperature for 3 hours, the mixture is filtered to give 3.0 g of methyl 6-[[bis(5-fluoro-2-methylbenzoyl)]amino]pyridine-3-carboxylate. The filtrate is concentrated to dryness and the residue triturated with hexane and ethyl acette to give an additional 9.0 g of bis acylated compound.

A mixture of 12.0 g of methyl 6-[[bis(5-fluoro-2-methylbenzoyl)]amino]pyridine-3-carboxylate, 60 ml of methanoltetrahydrofuran (1:1) and 23 ml of 5N NaOH is stirred at room temperature for 16 hours. The mixture is concentrated under vacuum, diluted with 25 ml of water, cooled and acidified with 1N HCl. The mixture is filtered and the solid washed with water to give 6.3 g of the product as a white solid.

As described for Reference Example 71, but substituting the appropriate aroyl chloride, heteroaroyl chloride, cycloalkanoyl chlorides, phenylacetylchlorides and related appropriate acid chlorides, the following 6-[(aroylamino]pyridine-3-carboxylic acids, 6-[(heteroaroyl)amino]pyridine-3-carboxylic acids and related 6-[(acylated)amino]pyridine-3-carboxylic acids are prepared.

REFERENCE EXAMPLE 72

6-[(3-Methyl-2-thienylcarbonyl)amino]pyridine-3-carboxylic acid

REFERENCE EXAMPLE 73

6-[(2-Methyl-3-thienylcarbonyl)amino]pyridine-3-carboxylic acid

REFERENCE EXAMPLE 74

6-[(3-Methyl-2-furanylcarbonyl)amino]pyridine-3-carboxylic acid

REFERENCE EXAMPLE 75

6-[(2-Methyl-3-furanylcarbonyl)amino]pyridine-3-carboxylic acid

REFERENCE EXAMPLE 76

6-[(3-fluoro-2-methylbenzoyl)amino]pyridine-3-carboxylic acid

REFERENCE EXAMPLE 77

6-[(2-Methylbenzoyl)amino]pyridine-3-carboxylic acid

REFERENCE EXAMPLE 78

6-[(2-chlorobenzoyl)amino]pyridine-3-carboxylic acid

REFERENCE EXAMPLE 79

6-[(2-Fluorobenzoyl)amino]pyridine-3-carboxylic acid

REFERENCE EXAMPLE 80

6-[(2-Chloro-4-fluorobenzoyl)amino]pyridine-3-carboxylic acid

REFERENCE EXAMPLE 81

6-[(2,4-Dichlorobenzoyl)amino]pyridine-3-carboxylic acid

REFERENCE EXAMPLE 82

6-[(4-Chloro-2-fluorobenzoyl)amino]pyridine-3-carboxylic acid

REFERENCE EXAMPLE 83

6-[(3,4,5-Trimethoxybenzoyl)amino]pyridine-3-carboxylic acid

REFERENCE EXAMPLE 84

6-[(2,4-Difluorobenzoyl)amino]pyridine-3-carboxylic acid

REFERENCE EXAMPLE 85

6-[(2-Bromobenzoyl)amino]pyridine-3-carboxylic acid

REFERENCE EXAMPLE 86

6-[(2-Chloro-4-nitrobenzoyl)amino]pyridine-3-carboxylic acid

REFERENCE EXAMPLE 87

6-[(Tetrahydrofuranyl-2-carbonyl)amino]pyridine-3-carboxylic acid

REFERENCE EXAMPLE 88

6-[(Tetrahydrothienyl-2-carbonyl)amino]pyridine-3-carboxylic acid

REFERENCE EXAMPLE 89

6-[(Cyclohexylcarbonyl)amino]pyridine-3-carboxylic acid

REFERENCE EXAMPLE 90

6-[(cyclohex-3-enecarbonyl)amino]pyridine-3-carboxylic acid

REFERENCE EXAMPLE 91

6-[(5-Fluoro-2-methylbenzeneacetyl)amino]pyridine-3-carboxylic acid

REFERENCE EXAMPLE 92

6-[(2-Chlorobenzeneacetyl)amino]pyridine-3-carboxylic acid

REFERENCE EXAMPLE 93

6-[(cyclopentylcarbonyl)amino]pyridine-3-carboxylic acid

REFERENCE EXAMPLE 94

6-[(cyclohexylacetyl)amino]pyridine-3-carboxylic acid

REFERENCE EXAMPLE 95

6-[(3-Methyl-2-thienylacetyl)amino]pyridine-3-carboxylic acid

REFERENCE EXAMPLE 96

6-[(2-Methyl-3-thienylacetyl)amino]pyridine-3-carboxylic acid

REFERENCE EXAMPLE 97

6-[(3-Methyl-2-furanylacetyl)amino]pyridine-3-carboxylic acid

REFERENCE EXAMPLE 98

6-[(2-Methyl-3-furanylacetyl)amino]pyridine-3-carboxylic acid

REFERENCE EXAMPLE 99

6-[(3-Methyl-2-tetrahydrothienylacetyl)amino]pyridine-3-carboxylic acid

REFERENCE EXAMPLE 100

6-[(2-Methyl-3-tetrahydrothienylacetyl)amino]pyridine-3-carboxylic acid

REFERENCE EXAMPLE 101

6-[(2,5-Dichlorobenzoyl)amino]pyridine-3-carboxylic acid

REFERENCE EXAMPLE 102

6-[(3,5-Dichlorobenzoyl)amino]pyridine-3-carboxylic acid

REFERENCE EXAMPLE 103

6-[(2-Methyl-4-chlorobenzoyl)amino]pyridine-3-carboxylic acid

REFERENCE EXAMPLE 104

6-[(2,3-Dimethylbenzoyl)amino]pyridine-3-carboxylic acid

REFERENCE EXAMPLE 105

6-[(2-Methoxybenzoyl)amino]pyridine-3-carboxylic acid

REFERENCE EXAMPLE 106

6-[(2-Trifluoromethoxybenzoyl)amino]pyridine-3-carboxylic acid

REFERENCE EXAMPLE 107

6-[(4-Chloro-2-methoxybenzoyl)amino]pyridine-3-carboxylic acid

REFERENCE EXAMPLE 108

6-[[2-(Trifluoromethyl)benzoyl]amino]pyridine-3-carboxylic acid

REFERENCE EXAMPLE 109

6-[(2,6-Dichlorobenzoyl)amino]pyridine-3-carboxylic acid

REFERENCE EXAMPLE 110

6-[(2,6-Dimethylbenzoyl)amino]pyridine-3-carboxylic acid

REFERENCE EXAMPLE 111

6-[(2-Methylthiobenzoyl)amino]pyridine-3-carboxylic acid

REFERENCE EXAMPLE 112

6-[(4-Fluoro-2-(trifluoromethyl)benzoyl)amino]pyridine-3-carboxylic acid

REFERENCE EXAMPLE 113

6-[(2,3-Dichlorobenzoyl)amino]pyridine-3-carboxylic acid

REFERENCE EXAMPLE 114

6-[(4-Fluoro-2-methylbenzoyl)amino]pyridine-3-carboxylic acid

REFERENCE EXAMPLE 115

6-[(2,3,5-Trichlorobenzoyl)amino]pyridine-3-carboxylic acid

REFERENCE EXAMPLE 116

6-[(5-Fluoro-2-chlorobenzoyl)amino]pyridine-3-carboxylic acid

REFERENCE EXAMPLE 117

6-[(2-Fluoro-5-(trifluoromethyl)benzoyl)amino]pyridine-3-carboxylic acid

REFERENCE EXAMPLE 118

6-[(5-Fluoro-2-methylbenzoyl)amino]pyridine-3-carbonyl chloride

A mixture of 6.2 g of 6-[(5-fluoro-2-methylbenzoyl)amino]pyridine-3-carboxylic acid and 23 ml of thionyl chloride is refluxed for 1 hour. An additional 12 ml of thionyl chloride is added and the mixture refluxed for 0.5 hour. The mixture is concentrated to dryness under vacuum and 30 ml of toluene added to the residue. The toluene is removed under vacuum and the process (add toluene and remove) is repeated to give 7.7 g of crude product as a solid.

As described for Reference Example 118, the following 6-(acyl)amino)pyridine-3-carbonyl chlorides are prepared.

REFERENCE EXAMPLE 119

6-[(3-Methyl-2-thienylcarbonyl)amino]pyridine-3-carbonyl chloride

REFERENCE EXAMPLE 120

6-[(2-Methyl-3-thienylcarbonyl)amino]pyridine-3-carbonyl chloride

REFERENCE EXAMPLE 121

6-[(3-Methyl-2-furanylcarbonyl)amino]pyridine-3-carbonyl chloride

REFERENCE EXAMPLE 122

6-[(2-Methyl-3-furanylcarbonyl)amino]pyridine-3-carbonyl chloride

REFERENCE EXAMPLE 123

6-[(3-Fluoro-2-methylbenzoyl)amino]pyridine-3-carbonyl chloride

REFERENCE EXAMPLE 124

6-[(2-Methylbenzoyl)amino]pyridine-3-carbonyl chloride

REFERENCE EXAMPLE 125

6-[(2-Chlorobenzoyl)amino]pyridine-3-carbonyl chloride, white crystals

REFERENCE EXAMPLE 126

6-[(2-Fluorobenzoyl)amino]pyridine-3-carbonyl chloride

REFERENCE EXAMPLE 127

6-[(2-Chloro-4-fluorobenzoyl)amino]pyridine-3-carbonyl chloride

REFERENCE EXAMPLE 128

6-[(2,4-Dichlorobenzoyl)amino]pyridine-3-carbonyl chloride

REFERENCE EXAMPLE 129

6-[(4-Chloro-2-fluorobenzoyl)amino]pyridine-3-carbonyl chloride

REFERENCE EXAMPLE 130

6-[(3,4,5-Trimethoxybenzoyl)amino]pyridine-3-carbonyl chloride

REFERENCE EXAMPLE 131

6-[(2,4-Difluorobenzoyl)amino]pyridine-3-carbonyl chloride

REFERENCE EXAMPLE 132

6-[(2-Bromobenzoyl)amino]pyridine-3-carbonyl chloride

REFERENCE EXAMPLE 133

6-[(2-Chloro-4-nitrobenzoyl)amino]pyridine-3-carbonyl chloride

REFERENCE EXAMPLE 134

6-[(Tetrahydrofuranyl-2-carbonyl)amino]pyridine-3-carbonyl chloride

REFERENCE EXAMPLE 135

6-[(Tetrahydrothienyl-2-carbonyl)amino]pyridine-3-carbonyl chloride

REFERENCE EXAMPLE 136

6-[(Cyclohexylcarbonyl)amino]pyridine-3-carbonyl chloride

REFERENCE EXAMPLE 137

6-[(Cyclohex-3-enecarbonyl)amino]pyridine-3-carbonyl chloride

REFERENCE EXAMPLE 138

6-[(2-Methylbenzeneacetyl)amino]pyridine-3-carbonyl chloride

REFERENCE EXAMPLE 139

6-[(2-Chlorobenzeneacetyl)amino]pyridine-3-carbonyl chloride

REFERENCE EXAMPLE 140

6-[(Cyclopentylcarbonyl)amino]pyridine-3-carbonyl chloride

REFERENCE EXAMPLE 141

6-[(Cyclohexylacetyl)amino]pyridine-3-carbonyl chloride

REFERENCE EXAMPLE 142

6-[(3-Methyl-2-thienylacetyl)amino]pyridine-3-carbonyl chloride

REFERENCE EXAMPLE 143

6-[(2-Methyl-3-thienylacetyl)amino]pyridine-3-carbonyl chloride

REFERENCE EXAMPLE 144

6-[(3-Methyl-2-furanylacetyl)amino]pyridine-3-carbonyl chloride

REFERENCE EXAMPLE 145

6-[(2-Methyl-3-furanylacetyl)amino]pyridine-3-carbonyl chloride

REFERENCE EXAMPLE 146

6-[(2-Methyl-5-fluorobenzeneacetyl)amino]pyridine-3-carbonyl chloride

REFERENCE EXAMPLE 147

6-[(3-Methyl-2-tetrahydrothienylacetyl)amino]pyridine-3-carbonyl chloride

REFERENCE EXAMPLE 148

6-[(2-Methyl-3-tetrahydrothienylacetyl)amino]pyridine-3-carbonyl chloride

REFERENCE EXAMPLE 149

6-[(2,5-Dichlorobenzoyl)amino]pyridine-3-carbonyl chloride

REFERENCE EXAMPLE 150

6-[(3,5-Dichlorobenzoyl)amino]pyridine-3-carbonyl chloride

REFERENCE EXAMPLE 151

6-[(2-Methyl-4-chlorobenzoyl)amino]pyridine-3-carbonyl chloride

REFERENCE EXAMPLE 152

6-[(2,3-Dimethylbenzoyl)amino]pyridine-3-carbonyl chloride

REFERENCE EXAMPLE 153

6-[(2-Methoxybenzoyl)amino]pyridine-3-carbonyl chloride

REFERENCE EXAMPLE 154

6-[(2-Trifluoromethoxylbenzoyl)amino]pyridine-3-carbonyl chloride

REFERENCE EXAMPLE 155

6-[(4-Chloro-2-methoxybenzoyl)amino]pyridine-3-carbonyl chloride

REFERENCE EXAMPLE 156

6-[[2-(Trifluoromethyl)benzoyl]amino]pyridine-3-carbonyl chloride

REFERENCE EXAMPLE 157

6-[(2,6-Dichlorobenzoyl)amino]pyridine-3-carbonyl chloride

REFERENCE EXAMPLE 158

6-[(2,6-Dimethylbenzoyl)amino]pyridine-3-carbonyl chloride

REFERENCE EXAMPLE 159

6-[(2-Methylthiobenzoyl)amino]pyridine-3-carbonyl chloride

REFERENCE EXAMPLE 160

6-[(4-Fluoro-2-(trifluoromethyl)benzoyl)amino]pyridine-3-carbonyl chloride

REFERENCE EXAMPLE 161

6-[(2,3-Dichlorobenzoyl)amino]pyridine-3-carbonyl chloride

REFERENCE EXAMPLE 162

6-[(4-Fluoro-2-methylbenzoyl)amino]pyridine-3-carbonyl chloride

REFERENCE EXAMPLE 163

6-[(2,3,5-Trichlorobenzoyl)amino]pyridine-3-carbonyl chloride

REFERENCE EXAMPLE 164

6-[(5-Fluoro-2-chlorobenzoyl)amino]pyridine-3-carbonyl chloride

REFERENCE EXAMPLE 165

6-[(2-Fluoro-5-(trifluoromethyl)benzoyl)amino]pyridine-3-carbonyl chloride

As described for Reference Example 71, the following bis acylated products (Table A) are prepared and purified by silica gel chromatography. These compounds are then hydrolysed to the acids as described in Example 71 (Table B).

TABLE A

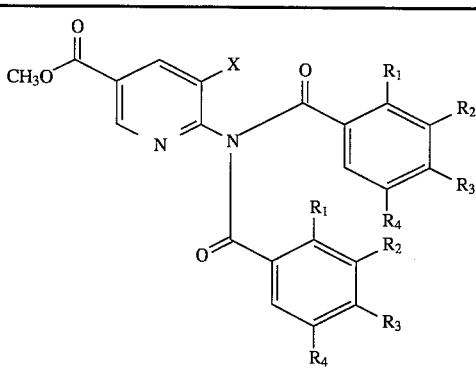

| Ref. Ex No. | $R_1$ | $R_2$ | $R_3$ | $R_4$ | X | $M^+$ |
|---|---|---|---|---|---|---|
| 166 | $CH_3$ | H | H | H | H | 388 |

TABLE A-continued

Structure: Methyl pyridine-carboxylate with X substituent, N connected to two benzoyl groups with R1, R2, R3, R4 substituents.

| Ref. Ex No. | R₁ | R₂ | R₃ | R₄ | X | M⁺ |
|---|---|---|---|---|---|---|
| 167 | CH₃ | H | H | F | H | 424 |
| 168 | CH₃ | F | H | H | H | 426 |
| 169 | H | OCH₃ | OCH₃ | OCH₃ | H | 540 |
| 170 | Cl | H | H | H | H | 430 |
| 171 | F | H | F | H | H | 396 |
| 172 | Br | H | H | H | H | 520 |
| 173 | Cl | H | F | H | H | 412 |
| 174 | Ph | H | Ph | H | H | 512 |
| 175 | Cl | H | H | Br | H | 474 |
| 176 | CH₃ | H | H | F | Br | |
| 177 | CH₃ | H | H | H | Br | 468 |

M⁺ is molecular ion found from FAB mass spectrum

TABLE B

Structure: Carboxylic acid pyridine with X substituent, NH linked to benzoyl group with R1-R4 substituents.

| Ref Ex. No. | R₁ | R₂ | R₃ | R₄ | X | M⁺ |
|---|---|---|---|---|---|---|
| 178 | CH₃ | H | H | H | H | 256 |
| 179 | CH₃ | H | H | F | H | 274 |
| 180 | CH₃ | F | H | H | H | 274 |
| 181 | H | OCH₃ | OCH₃ | OCH₃ | H | 332 |
| 182 | Cl | H | H | H | H | 276 |
| 183 | F | H | F | H | H | 278 |
| 184 | Br | H | H | H | H | 322 |
| 185 | Cl | H | F | H | H | 294 |
| 186 | Ph | H | H | H | H | 318 |
| 187 | Cl | H | H | Br | H | 356 |
| 188 | CH₃ | H | H | F | Cl | |
| 189 | CH₃ | H | H | H | Br | 336 |

M⁺ is molecular ion found from FAB mass spectrum.

REFERENCE EXAMPLE 190

6-Amino-5-bromopyridine-3-carboxylic acid

To a stirred solution of 6-aminonicotinic acid (13.8 g, 0.1 mole) in glacial acetic acid (100 ml), bromine (16 g, 5 ml, 0.1 mole) in acetic acid (20 ml) is added slowly. The reaction mixture is stirred for 8 hours at room temperature and the acetic acid is removed under reduced pressure. The yellow solid residue is dissolved in water and carefully neutralized with 30% NH₄OH. The separated solid is filtered and washed with water to give 18 g of solid; mass spectrum: 218 (M⁺).

REFERENCE EXAMPLE 191

Methyl 6-amino-5-bromopyridine-3-carboxylate

6-Amino-5-bromopyridine-3-carboxylic acid (10 g, 50 mmol) is dissolved in saturated methanolic HCl (100 ml) and refluxed for 24 hours. The solvent, methanol, is removed under reduced pressure and the residue is dissolved in ice cold water. The aqueous solution is neutralized with 0.1N NaOH and the solid which separates is filtered; washed well with water and air dried to yield 10 g of product as a solid: mass spectrum 231 (M⁺).

REFERENCE EXAMPLE 192

6-[(2-Methylbenzeneacetyl)amino]pyridine-3-carboxylic acid

To a cooled (0° C.) mixture of 5.0 g methyl 6-aminopyridine-3-carboxylate, 12.6 ml of N,N-diisopropylethylamine in 40 ml of dichloromethane is added a solution of 12.2 g of 2-methylbenzeneacetyl chloride in 10 ml of dichloromethane. The mixture is stirred under argon at room temperature overnight. The mixture is diluted with 200 ml of dichloromethane and 50 ml of water and the organic layer separated. The organic layer is washed with 50 ml each of 1M NaHCO₃, brine and dried (Na₂SO₄). The solution is filtered through a thin pad of hydrous magnesium silicate and the filtrate concentrated to dryness. The residue (9.0 g) is chromatographed on a silica gel column with hexane-ethyl acetate (3:1) as eluent to give 8.6 g of solid. This solid, mainly methyl 6-[[bis(2-methylbenzeneacetyl)]amino]pyridine-3-carboxylate, is dissolved in 60 ml of tetrahydrofuran-methanol (1:1) and 23 ml of 5N NaOH added to the solution. The mixture is stirred at room temperature overnight and the mixture concentrated under vacuum. Water (25 ml) is added and the mixture is stirred and acidified with cold 1N HCl. The mixture is chilled and the solid filtered and washed with water to give 5.9 g of off-white solid.

REFERENCE EXAMPLE 193

6-[(2 -Methylbenzeneacetyl)amino]pyridine-3-carbonyl chloride

A mixture of 4.5 g of 6-[(2-methylbenzeneacetyl)amino] pyridine-3-carboxylic acid and 25 ml of thionyl chloride is refluxed for 1 hour and then concentrated to dryness under vacuum. To the residue is added 20 ml of toluene and the solvent removed under vacuum. The addition and removal of toluene is repeated and the residual solid dried at room temperature under vacuum to give 5.3 g of dark brown solid.

REFERENCE EXAMPLE 194

2-(2-Pyridinyl)benzoic acid

A mixture of methyl 2-iodobenzoate (12 g, 47 mmol), 2-pyridinyl-tri-n-butyl stannane (20 g, 55 mmol) and tetrakis (triphenyl phosphine) palladium (O) (2 g), is refluxed in toluene (degassed) for 48 hours. The reaction mixture is concentrated under vacuum and the residue is chromatographed on a column of silica gel with 50% ethylacetate-:hexane as eluent. The initial fractions (2 lits) are discarded and finally the product methyl 2-(2-pyridinyl)benzoate, is eluted and isolated as an oil. (Yield: 5.5 g): mass spectrum, 213 (M⁺)

A mixture of the preceding compound (3.0 g, 14 mmol) and NaOH (600 mg, 15 mmol) is refluxed in MeOH:water (9:1) (50 ml) for 4 hours. When the reaction is complete, it is concentrated under vacuum and the residue dissolved in 50 ml of cold water. Neutralization with glacial acetic acid affords a solid which is filtered off and washed with water to give 2.5 g of brown solid; slightly soluble in water; mass spectrum (CI) 200 (M$^+$1).

REFERENCE EXAMPLE 195

Ethyl 3-[N-(3-ethoxycarbonyl-2-pyridinyl)-N-(4-methylphenylsulfonyl)]aminobutane-1-carboxylate A mixture of 13.4 g of ethyl 2-[(4-methylphenylsulfonyl)amino]pyridine-3-carboxylate, 23.1 g of anhydrous potassium carbonate and 20.4 g of ethyl 3-bromobutane-1-carboxylate in 300 ml of N,N-dimethylformamide is heated at 110° C. under argon for 6 hours. The mixture is concentrated to dryness under high vacuum and to the residue is added $CH_2Cl_2$ and $H_2O$. The organic layer is separated and washed with water (3 times), treated with activated carbon and dried ($MgSO_4$). The solvent is removed and the residue chromatographed on a short column of silica gel. The column is eluted with 1900 ml of $CH_2Cl_2$, then 1300 ml of $CH_2Cl_2$ and finally with 4 L of 5% ethyl acetate in $CH_2Cl_2$. The 5% ethyl acetate in $CH_2Cl_2$ fractions are combined and the combined fraction dried ($MgSO_4$) and the solvent removed to give 16.9 g of white crystals. A 0.5 g sample is recrystallized from toluene to give white crystals (washed with hexane) (0.39 g) m.p. 129.5°–130° C.

REFERENCE EXAMPLE 196

Ethyl 8,9-dihydro-5-hydroxy-9-[(4-methylphenyl)sulfonyl]-7H-pyrido[2,3-b]azepine-6-carboxylic acid To a solution of 7.85 g (70.0 mmol) of potassium tert-butoxide in 150 ml of tetrahydrofuran, chilled in an ice bath, is added 15.2 g (35.0 mmol) of ethyl 3-[N-(3-carbethoxy-2-pyridinyl)-N-(4-methylphenylsulfonyl)]aminobutane-1-carboxylate in 150 ml of dry tetrahydrofuran dropwise over 50 min. The mixture is stirred in an ice bath for 5 hours and poured in 500 ml of ice water. The mixture is brought to pH 5 with 10% HCl and extracted with ethyl acetate (4 times). The extract is dried ($MgSO_4$) and the solvent removed under vacuum. The residue is chromatographed on silica gel with 10% ethyl acetate in $CH_2Cl_2$ as eluent. Fractions containing product are combined and the solvent removed to give 12.8 g of a pale yellow gum; Mass Spectrum (FAB) 389 (M+H); 411 (M+Na).

REFERENCE EXAMPLE 197

6,7,8,9-Tetrahydro-9-[(4-methylphenyl)sulfonyl]-5H-pyrido[2,3-b]azepin-5-one A mixture of 13.2 g of ethyl 8,9-dihydro-5-hydroxy-9-[(4-methylphenylsulfonyl]-7H-pyrido[2,3-b]azepine-6-carboxylate, 265 ml of dimethylsulfoxide and 1.52 ml of water under argon is heated at 150° C. 16.5 hours. The mixture is poured into 2700 ml of ice water and the mixture chilled 16 hours. The mixture is filtered and the solid washed with water and dried. The tan solid is dissolved in ethyl acetate and the solution washed with 50 ml (4 times) of water. Activated carbon is added to the solution and the mixture filtered through magnesium sulfate. The filtrate is concentrated to dryness under vacuum to give 10.4 g of solid. The solid (9.24 g) is filtered through silica gel with 5% ethyl acetate in dichloromethane as solvent. The filtrate is concentrated under vacuum to give 6.7 g of off-white solid; Mass Spectrum (CI) (M$^+$+H) 317.

REFERENCE EXAMPLE 198

6,7,8,9-Tetrahydro-5-(2-chloro-4-nitrobenzoyl)-5H-pyrido[3,2-b]azepine, 1-oxide To a solution of 0.497 g of 6,7,8,9-tetrahydro-5-(2-chloro-4-nitrobenzoyl)-5H-pyrido[3,2-b]azepine in 7 ml of chloroform is added 1.04 g of 3-chloroperbenzoic acid. The mixture is refluxed overnight and the solvent removed under vacuum. To the residue is added 100 ml of water and the mixture extracted with dichloromethane. The extract is washed with $H_2O$, 1N $NaHCO_3$, $H_2O$ and dried ($Na_2SO_4$). The solution is filtered through a thin pad of hydrous magnesium silicate. The filter pad is washed with 10% methanol in ethyl acetate to give 0.49 g of product as a glass (foam), m.p. 110°–125° C.

REFERENCE EXAMPLE 199

6,7,8,9-Tetrahydro-5H-pyrido[2,3-b]azepin-5-one

A solution of 5.00 g of 6,7,8,9-tetrahydro-9-[(4-methylphenyl)sulfonyl]-5H-pyrido[2,3-b]azepin-5-one in 60 ml of 40% (v/v) sulfuric acid in acetic acid is heated at 60° C. for 11 hours. The mixture is chilled and poured into 350 ml of ice water (cooled in an ice bath) with thorough stirring. To the cold mixture is added solid NaOH until the pH is 8 while keeping the temperature below 30° C. The mixture is filtered and the solid washed with ethyl acetate. The organic layer of the filtrate is separated and the aqueous layer extracted with ethyl acetate. The organic layer and extracts are combined and treated with activated carbon. The mixture is filtered through $MgSO_4$ and the solvent removed under vacuum to give 2.0 g of yellow crystals.

REFERENCE EXAMPLE 200

6,7,8,9-Tetrahydro-9-(2-chloro-4-nitrobenzoyl)-5H-pyrido[2,3-b]azepin-5-one

To a solution of 6,7,8,9-tetrahydro-5H-pyrido[2,3-b]azepin-5-one and 0.234 g of triethylamine in 6 ml of dichloromethane is added 0.506 g of 2-chloro-4-nitrobenzoyl chloride in 2 ml of dichloromethane. The mixture is stirred at room temperature overnight under argon. The solution is washed with $H_2O$, 10% $NaHCO_3$ and dried ($MgSO_4$). The solvent is removed to give a brown oil which crystallizes. The mixture is chromatographed on silica with a waters Prep-500 instrument with ethyl acetate-hexane (1:1) as solvent to give 2.4 g of off-white crystals, m.p. 162°–164° C. (identified as O-2-chloro-4-nitrobenzoyl derivative (2-chloro-4-nitrobenzoyl enolate of product) and 0.80 g of product as crystals, m.p. slowly decomposes 160°–220° C.

REFERENCE EXAMPLE 201

6-(4-Aminobenzoyl)-1,4,5,6-tetrahydropyrazolo[3,4-d]thieno[3,2-b]azepine

A mixture of 2.0 g of 6-(4-nitrobenzoyl)-1,4,5,6-tetrahydropyrazolo[3,4-b]thieno[3,2-b]azepine in 40 ml of absolute ethanol is stirred under argon while 1.6 ml of hydrazine is added. The reaction mixture is heated at 60° C. for 1.5 hours. The reaction mixture is cooled to room temperature and 400 mg of 10% Pd/C added and the reaction mixture heated at 100° C. for 1.5 hours. The reaction mixture is filtered through diatomaceous earth and the cake washed with methylene chloride. The filtrate is concentrated in vacuo to a residue which is crystallized from ethyl acetate:hexane to give 1.4 g of the desired product as yellow crystals, 242°–260° C.

REFERENCE EXAMPLE 202

7-[(Dimethylamino)methylene]-4,5,6,7-tetrahydro-4-(2-chloro-4-nitrobenzoyl)-8H-thieno[3,2-b]azepin-8-one A mixture of 3.0 g of 4,5,6,7-tetrahydro-4-(2-chloro-4-nitrobenzoyl)-8H-thieno[3,2-b]azepin-8-one and 20 ml of tert-butoxy-bis(dimethylamino)methane is heated on a steam bath 2 hours followed by the addition of 10 ml of methylene chloride. The reaction mixture is refluxed for 1 hour. The reaction mixture is evaporated in vacuo to a residue which is diluted with 100 ml of methylene chloride and filtered through a pad of hydrous magnesium silicate. The filtrate is filtered through a short column of silica gel to give 2.45 g of the desired product as a yellow foam.

REFERENCE EXAMPLE 203

6-(2-Chloro-4-nitrobhenzoyl)-1,4,5,6-tetrahydropyrazolo[3,4-d]thieno[3,2-b]azepine To a mixture of 2.2 g of 7-[(dimethylamino)methylene]-4,5,6,7-tetrahydro-4-(2-chloro-4-nitrobenzoyl)- 8H-thieno[3,2-b]azepine in 40 ml of ethanol is added 341 µl of hydrazine followed by heating at 60° C. for 1.5 hours. The volatiles are evaporated in vacuo to a residue which is dissolved in 100 ml of ethyl acetate and filtered through a pad of hydrous magnesium silicate. The filtrate is evaporated in vacuo to give 1.85 g of the desired product as a yellow-orange solid.

REFERENCE EXAMPLE 204

6-(2-Chloro-4-aminobenzoyl)-1,4,5,6-tetrahydropyrazolo[3,4-d]thieno[3,2-b]azepine A mixture of 1.8 g of 6-(2-chloro-4-nitrobenzoyl)-1,4,5,6-tetrahydropyrazolo[3,4-d]thieno[3,2-b]azepine in 35 ml of absolute ethanol is added 5.42 g of tin (II) chloride followed by heating at reflux for 1 hour at 80° C. The volatiles are evaporated in vacuo to a residue which is partitioned between 150 ml of ethyl acetate and saturated aqueous NaHCO₃ the reactants are stirred at room temperature for 1 hour and filtered. The organic layer is separated and washed with 30 ml of brine, dried (Na₂SO₄) and filtered through a pad of hydrous magnesium silicate. The filtrate is evaporated in vacuo to give 1.55 g of a yellow-orange foam.

REFERENCE EXAMPLE 205

7-[(Dimethylamino)methylene]-4,5,6,7-tetrahydro-4-(4-nitrobenzoyl-8H-thieno[3,2-b]azepin-8-one A mixture of 3.2 g of 4,5,6,7-tetrahydro-4-(4-nitrobenzoyl)-8H-thieno[3,2-b]azepin-8-one and 32 ml of tert-butoxybis(dimethylamino)methane is heated on a steam bath for 3.5 hours. The reaction mixture is allowed to stand for 48 hours. The reaction mixture is evaporated in vacuo and the concentrate is dissolved in 150 ml of methylene chloride and filtered through hydrous magnesium silicate two times. The volatiles are evaporated in vacuo to a residue which is dissolved in 25 ml of ethyl acetate and filtered. The filtrate is cooled to give 3.2 g of the desired product as a light orange solid, m.p. 214°–216° C.

REFERENCE EXAMPLE 206

N-[4-[[7-(Dimethylaminomethylene)]-5,6,7,8-tetrahydro-8-oxo-4H-thieno[3,2-b]azepin-4-yl)carbonyl]phenyl]-2-methylbenzamide A mixture of 100 mg of N-[4-[(5,6,7,8-tetrahydro-8-oxo-4H-thieno[3,2-b]azepin-4-yl)carbonyl]phenyl]-2-methylbenzamide and 1 ml of tert-butoxybis(dimethylamino)methane is heated at 50° C. for 1 hour. To the reaction mixture is added 3 ml of methylene chloride and heating continued for an additional 2 hours at 60°–70° C. The volatiles are evaporated to a residue which is dissolved in 25 ml of methylene chloride and filtered through a pad of hydrous magnesium silicate. The filtrate is evaporated in vacuo to a residue which is purified by chromatography on preparative thick layer silica gel plates by elution with ethyl acetate to afford 20 mg of the desired product as a light yellow solid.

REFERENCE EXAMPLE 207

2-Chloro-7-[(dimethylamino)methylene]-4,5,6,7-tetrahydro-4-(4-nitrobenzoyl-8H-thieno[3,2-b]azepin-8-one A mixture of 1.1 g of 2-chloro-4,5,6,7-tetrahydro-4-(4-nitrobenzoyl)-8H-thieno[3,2-b]azepin-8-one and 11 ml of tertbutoxy-bis(dimethylamino)methane is heated at reflux for 3.5 hours. The reaction mixture is allowed to stand for 24 hours. The reaction mixture is evaporated in vacuo and the concentrate is purified by column chromatography on silica gel to give 520 mg of the desired product as a non-crystalline solid.

REFERENCE EXAMPLE 208

8-Chloro-2,4,5,6-tetrahydro-2-methyl-6-(4-nitrobenzoyl)pyrazolo[3,4-d]thieno[3,2-b]azepine A mixture of 500 mg of 2-chloro-7-[(dimethylamino)methylene]-4,5,6,7-tetrahydro-4-(4-nitrobenzoyl)- 8H-thieno[3,2-b]azepin-8-one in 15 ml of absolute methanol is stirred under argon while 131 µl of N-methylhydrazine is added. The reaction mixture is heated at 80° C. for 18 hours. The reaction mixture is cooled to room temperature and concentrated in vacuo to give 420 mg of the desired product as a solid.

REFERENCE EXAMPLE 209

6-(2-Chloro-4-aminobenzoyl)-1,4,5,6-tetrahydropyrazolo[3,4-d]pyrido[3,2-b]azepine As described for Reference Example 204, 6-(2-chloro-4-nitrobenzoyl)-1,4,5,6-tetrahydropyrazolo-[3,4-d]pyrido[3,2-b]azepine is reduced with stannus chloride (SnCl₂) in ethanol to give the product as a solid.

REFERENCE EXAMPLE 210

5-(2-Chloro-4-aminobenzoyl)-4,10-dihydro-5H-pyrido[3,2-b]thieno[2,3-e]azepine

As described for Reference Example 204 5-(2-chloro-4-nitrobenzoyl)-4,10-dihydro-5H-pyrido[3,2-b]thieno[2,3-e]azepine is reduced with stannus chloride (SnCl$_2$) in ethanol to give the product as a solid.

REFERENCE EXAMPLE 211

5-(2-Chloro-4-aminobenzoyl)-6,10-dihydro-5H-pyrido[3,2 -b]thieno[3,2-e]azepine

As described for Reference Example 204 5-(2 -chloro-4-nitrobenzoyl)-6,10-dihydro-5H-pyrido[3,2-b]thieno[3,2-e]azepine is reduced with stannus chloride (SnCl$_2$) in ethanol to give the product as a solid.

REFERENCE EXAMPLE 212

5-(4-Nitrobenzoyl)-6,7,8,9-tetrahydro-5H-pyrido[3,2-b]azepine

A solution of 2.96 g of 6,7,8,9-tetrahydro-5H-pyrido[3,2-b]azepine, 3.03 g of triethylamine and 4.45 of 4-nitrobenzoyl chloride in 30 ml of dichloromethane is stirred under argon at room temperature for 4 hours. The mixture is poured into water and the organic layer separated and washed with saturated NaHCO$_3$, H$_2$O and brine. The organic layer is dried (Na$_2$SO$_4$) and filtered through a thin pad of hydrous magnesium silicate. The filtrate is concentrated to dryness to give 6.35 g of solid. Trituration with 25 ml of dichloromethane gives 5.50 g of light yellow solid. A sample from a prior run in trituration gives white crystals, m.p. 231°–233° C.

REFERENCE EXAMPLE 213

5-(4-Nitrobenzoyl)-6,7,8,9-tetrahydro-5H-pyrido[3,2-b]azepine, 1-oxide

A mixture of 1.18 g of 5-(4-nitrobenzoyl)- 6,7,8,9-tetrahydro-5H-pyrido[3,2-b]azepine and 1.37 g of 3-chloroperoxybenzoic acid in 10 ml of dichloromethane is stirred at room temperature overnight under argon. The mixture is diluted with 15 ml of dichloromethane and the solution washed with 1N NaHCO$_3$, H$_2$O, brine and dried (Na$_2$SO$_4$). The solution is filtered through a thin pad of hydrous magnesium silicate. The filter pad is washed with 50 ml of ethyl acetate. Then the filter pad is washed with ethyl acetate-methanol (5:1) and the ethyl acetate-methanol wash collected and the solvent removed to give 0.86 g of crystals, m.p. 231°–233° C.

REFERENCE EXAMPLE 214

5-(2-Chloro-4-nitrobenzoyl)-6,7,8,9-tetrahydro-5H-pyrido[3,2-b]azepine, 1-oxide

A mixture of 0.497 g of 5-(2-chloro-4-nitrobenzoyl)-6,7,8,9-tetrahydro-5H-pyrido[3,2-b]azepine and 0.38 g of 3-chloroperoxybenzoic acid in 7 ml of dichloromethane is refluxed under argon for 16 hours. The solvent is removed under argon and to the residue is added water. The mixture is extracted with dichloromethane and the extract washed with 1N NaHCO$_3$, H$_2$O and dried (Na$_2$SO$_4$). The solution is filtered through a thin pad of hydrous magnesium silicate. The pad is washed with ethyl acetate and then with ethyl acetate-methanol (9:1). The ethyl acetate-methanol wash is collected separately and the solvent removed under vacuum to give the product as a glass, m.p. 110°–125° C.

REFERENCE EXAMPLE 215

5-(2-Chloro-4-nitrobenzoyl)-9-hydroxy-6,7,8,9 -tetrahydro-5H-pyrido[3,2-b]azepine, O-acetate A mixture of 0.49 g of 5-(2-chloro-4-nitrobenzoyl)- 6,7,8,9-tetrahydro-5H-pyrido[3,2b]azepine, 1-oxide in 5 ml of acetic anhydride is heated in an oil bath at 90° for 36 hours. Toluene (25 ml) is added and the mixture concentrated under high vacuum. The process is repeated and the residue chromatographed on silica gel preparative plates with ethyl acetate as solvent to give 0.24 g of crystals, m.p. 162°–165° C.

Anal. Calc'd for C$_{18}$H$_{15}$ClN$_3$O$_5$. C, 55.5; H, 4.1; N, 10.8. Found: C,55.5; H,4.0; N,10.6.

REFERENCE EXAMPLE 216

5-(4-Nitrobenzoyl)-9-hydroxy -6,7,8,9-tetrahydro-5H-pyrido[3,2-b]azepine, O-acetate A mixture of 0.58 g of 5-(4-nitrobenzoyl)- 6,7,8,9-tetrahydro-5H-pyrido[3,2-b]azepine, 1-oxide and 5 ml of acetic anhydride in 10 ml of dichloromethane is refluxed for 2 days. An additional 2 ml of acetic anhydride is added and the mixture refluxed 2 days. To the mixture is added toluene (30 ml-twice) and the solvent removed under high vacuum. The residue is chromatographed on silica gel preparative plates with ethyl acetate as solvent to give 0.37 g of crystals, m.p. 135°–137° C.

REFERENCE EXAMPLE 217

2-(4-Nitrobenzoyl)-9-hydroxy-6,7,8,9-tetrahydro-5H-pyrido[3,2- b]azepine

To a mixture of 0.5 g of 5-(4-nitrobenzoyl)-9 -hydroxy-6,7,8,9-tetrahydro-5H-pyrido[3,2-b]azepine, O-acetate in 10 ml of methanol-water (8:2) is added KHCO$_3$ and the mixture stirred at room temperature overnight. The mixture is concentrated under vacuum, diluted with 10 ml of water and extracted with ethyl acetate. The extract is dried (Na$_2$SO$_4$) and the solvent removed to give the product as a solid. Chromatography on silica gel with ethyl acetate as solvent gives crystals, m.p. 182 °–185° C.

REFERENCE EXAMPLE 218

5,6,7,8-Tetrahydro-5-(4-nitrobenzoyl)-9H-pyrido[3,2-b]azepin- 9-one

A mixture of 0.5 g of 5-(4-nitrobenzoyl)-9 -hydroxy-6,7,8,9-tetrahydro-5H-pyrido[3,2-b]azepine in 5 ml of dimethyl sulfoxide and 1 ml of acetic anhydride is stirred at room temperature 16 hours. To the mixture is added 10 ml of water and 1N NaHCO$_3$. The mixture is extracted with ethyl acetate and the extract washed with water, 1N NaHCO$_3$, brine and dried. The solvent is removed to give a solid. chromatography on silica gel with ethyl acetate as solvent gives the product as a solid, m.p. 188°–190° C.

REFERENCE EXAMPLE 219

5,6,7,8-Tetrahydro-5-(2-chloro-4-nitrobenzoyl)-9H-pyrido[3,2-b]azepine-9-one

As described for Reference Example 218, 5-(2-chloro-4-nitrobenzoyl)-9-hydroxy-6,7,8,9-tetrahydro-5H-pyrido[3,2-b]azepine is reacted with dimethylsulfoxideacetic anhydride to give the product as a solid.

REFERENCE EXAMPLE 220

6,7,8,9-Tetrahydro-9-(4-nitrobenzoyl)-5H-pyrido[2,3-b]azepin-5-one

To a solution of 2.11 g of 6,7,8,9-tetrahydro- 5H-pyrido[2,3-d]azepin-5-one in 40 ml of dichloromethane is added 3.28 g of solid NaHCO$_3$. To the stirred mixture under argon is added dropwise 3.14 g of 4-nitrobenzoyl chloride in 30 ml of dichloromethane containing 2 ml of tetrahydrofuran and the mixture is stirred overnight. To the mixture is added tetrahydrofuran and water and the mixture filtered. The solid is washed with chloroform (solid dissolved) and the organic layer of the filtrate separated. The organic layer is filtered through MgSO$_4$ and the filtrate concentrated to dryness to give a white solid. The solid from two runs is dissolved in ethyl acetate-CH$_2$Cl$_2$ (2:8) and filtered through short silica gel column and the product fraction collected. The solvent is removed and the solid dissolved in hot chloroform-methanol and the solution treated with activated carbon. The mixture is filtered through diatomaceous earth and the filtrate concentrated to dryness under vacuum to give 7.73 g of white crystals; Mass Spectrum (CI) (CH$_4$): 312 (MH$^+$).

REFERENCE EXAMPLE 221

6-[(Dimethylamino)methylene]-6,7,8,9-tetrahydro-9-(4-nitrobenzoyl)-5H-pyrido[2,3-b]azepin-5-one To a slurry of 0.50 g of 6,7,8,9-tetrahydro-9-(4-nitrobenzoyl)-5H-pyrido[2,3-b]azepin-5-one in 10 ml of tetrahydrofuran under argon is added 0.70 g of tert-butoxy-bis(dimethylamino)methane and the mixture is stirred at room temperature overnight. The volatiles are removed under vacuum and the residue in ethyl acetate-CH$_2$Cl$_2$ (2:8) filtered through a short column of silica gel. The silica gel is washed with ethyl acetate (discard) and then with chloroform containing 3% methanol to give 0.51 g of the product as a yellow solid.

REFERENCE EXAMPLE 222

6-[(Dimethylamino)methylene]-6,7,8,9-tetrahydro-9-(2-chloro-4-nitrobenzoyl)-5H-pyrido[2,3-b]azepin-5-one To a solution of 0.20 g of 6,7,8,9-tetrahydro- 9-(2-chloro-4-nitrobenzoyl)-5H-pyrido[2,3-b]azepin-5-one in 2 ml of dioxane is added 0.504 g of tert-butoxybis(dimethylamino)methane and the mixture is stirred at room temperature. The volatiles are removed under high vacuum. The residue is dissolved in ethyl acetate —CH$_2$Cl$_2$ (3:7) and the solution passed through a short column of silica gel (ethyl acetate —CH$_2$Cl$_2$) eluate is discarded). Elution with ethyl acetate —CH$_2$Cl$_2$ (8:2) gives the product as a yellow glass (0.19 g); Mass Spectrum (CI) (CH$_4$); 401 (MH$^+$).

REFERENCE EXAMPLE 223

1,4,5,6-Tetrahydro-6-(4-nitrobenzoyl)pyrazolo[3,4-d]pyrido[2,3-b]azepine

To a slurry of 0.51 g of 6-[(dimethylamino)methylene]-6,7,8,9-tetrahydro-9-(4-nitrobenzoyl)-5H-pyrido[2,3-b]azepin-5-one in 17 ml of methanol under argon is added 0.14 g of hydrazine hydrate. The mixture is stirred overnight and the solvent removed under vacuum. The residue is dissolved in hot chloroform-methanol (95:5) and filtered through silica gel and washed filter pad with chloroform-methanol (95:5). The filtrate is concentrated to dryness to give 0.48 g of yellow solid.

REFERENCE EXAMPLE 224

1,4,5,6-Tetrahydro-6-(4-aminobenzoyl)pyrazolo[3,4-d]pyrido[2,3-b]azepine

To a slurry of 0.170 g of 1,4,5,6-tetrahydro- 6-(4-nitrobenzoyl)pyrazolo[3,4-d]pyrido[2,3-b]azepine in 8 ml of ethanol under argon is added 0.573 g of stannous chloride dihydrate (SnCl$_2$.2H$_2$O). The mixture is refluxed for 1 hour, diluted with ice-water and made basic with 10% NaHCO$_3$ solution. The mixture is stirred 3.5 hours and extracted with chloroform (3 times). The extract is dried (MgSO$_4$) and the solvent removed under vacuum. Chromatography on silica gel with ethyl acetate as eluent gives 0.10 g of off-white crystals.

REFERENCE EXAMPLE 225

8-[(Dimethylamino)methylene]-5,6,7,8-tetrahydro-5-(4-nitrobenzoyl)-9H-pyrido[3,2-b]azepin-9-one As described for Reference Example 221, 5,6,7,8-tetrahydro-5-(4-nitrobenzoyl)-9H-pyrido[3,2-b] azepin-9-one is reacted with tert-butoxybis(dimethylamino)methane to give the product as a solid.

REFERENCE EXAMPLE 226

1,4,5,6-Tetrahydro-6-(4-nitrobenzoyl)pyrazolo[3,4-d]pyrido[3,2-b]azepine

As described for Reference Example 223, 8-[(dimethylamino)methylene]-5,6,7,8-tetrahydro-5-(4-nitrobenzoyl)-9H-pyrido[3,2-b]azepin-9-one is reacted with hydrazine hydrate to give the product as a solid, m.p. 255°–256° C.

REFERENCE EXAMPLE 227

5,6-Dihydro-6-(4-aminobenzoyl)-4H-isoxazolo[5,4-d]-thieno[3,2-b]azepine

A mixture of 0.50 g of 7-[(dimethylamino)methylene]-4,5,6,7-tetrahydro-4-(4-nitrobenzoyl)-8H-thieno [3,2-b] azepin-8-one, 0.234 g of hydroxylamine, hydrochloride and 16 ml of methanol is refluxed for 4 hours. The mixture is chilled and filtered and the solid washed with a small amount of cold methanol and cold ethyl acetate to give 0.41 g of tan crystals, m.p. 218°–222° C. The preceding compound in ethanol is refluxed with SnCl$_2$.H$_2$O for one hour, cooled and diluted with ice-water. The mixture is made basic with 10% NaHCO$_3$ and is stirred for 3.5 hours at room temperature. The mixture is extracted with ethyl acetate and the extract washed with brine. The extract is dried (Na$_2$SO$_4$) and the solvent removed. The residue is chromatographed on silica gel with ethyl acetate-hexane as solvent to give the product as a solid.

REFERENCE EXAMPLE 228

5,6,7,8-Tetrahydro-5-(4-nitrobenzoyl)-9H-pyrido[3,2-b]azepin-9-one

A mixture of 0.313 g of 5-(4-nitrobenzoyl)-9-hydroxy-6,7,8,9-tetrahydro-5H-pyrido[3,2-b]azepine, 4 ml of $CH_2Cl_2$ and 0.75 ml of dimethylsulfoxide is chilled to −25° C. and 0.405 g of cyanuric chloride is added. The mixture is allowed to stand at −25° C. for 6.5 hours and 0.41 g of triethylamine is added. The mixture is stirred 10 minutes and poured into water. The mixture is extracted with dichloromethane and the extract washed with water, brine and dried ($Na_2SO_4$). The solvent is removed to give 0.39 g of solid. Chromatography on silica gel with ethyl acetate as solvent gives 0.17 g of crystals, m.p. 188°–190° C.

REFERENCE EXAMPLE 229

Methyl 4-[([1,1'-Biphenyl]-2-carbonyl)amino]-3-methoxybenzoate

A mixture of 10.0 g of [1,1'-biphenyl]-2-carboxylic acid in 75 ml of methylene chloride and 12.52 g of oxalyl chloride is stirred at room temperature for 15 hours. The volatiles are evaporated in vacuo to give 11.06 g of an oil. A 2.16 g portion of the above oil in 25 ml of methylene chloride is reacted with 1.81 g of methyl 4-amino-3-methoxybenzoate and 1.30 g of N,N-diisopropylethylamine by stirring at room temperature for 18 hours. The reaction mixture is washed with water, saturated aqueous $NaHCO_3$ and the organic layer dried($Na_2SO_4$). The organic layer is passed through hydrous magnesium silicate and hexane added to the filtrate at the boil to give 3.20 g of the desired product as a crystalline solid, m.p. 115°–117° C.

REFERENCE EXAMPLE 230

Methyl 4-[(1,1'-Biphenyl]-2-carbonyl)amino]-2-chlorobenzoate

A solution of 2.37 g of [1,1'-biphenyl]-2-carbonyl chloride in 10 ml of methylene chloride is added dropwise to an ice cold solution of 1.84 g of methyl 4-amino-2-chlorobenzoate and 1.49 g of N,N-diisopropylethylamine in 50 ml of methylene chloride. The reaction mixture is stirred at room temperature for 18 hours and washed with water, saturated aqueous $NaHCO_3$ and the organic layer dried($Na_2SO_4$). The organic layer is passed through a pad of hydrous magnesium silicate and hexane added at the boil to give 1.1 g of the desired product as a crystalline solid, m.p. 132°–134° C. $M^+H=365$.

REFERENCE EXAMPLE 231

4-[([1,1,-Biphenyl]-2-carbonyl)amino]-2-chlorobenzoic Acid

A mixture of 3.0 g of methyl 4-[([1,1'-biphenyl]-2-carbonyl)amino]-2-chlorobenzoate in 75 ml of absolute ethanol and 2.0 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 0.1 g of the desired product as a crystalline solid, m.p. 217°–219° C.

REFERENCE EXAMPLE 232

4-[([1,1'-Biphenyl]-2-carbonyl)-amino]-3-methoxybenzoyl Chloride

A solution of 2.69 g of 4-[([1,1'-biphenyl]-2-carbonyl] amino]-3-methoxy benzoic acid in 5 ml of thionyl chloride is heated on a steam bath for 1 hour under Argon. The volatiles are removed in vacuo to give a residue which is stirred with hexane to give 2.58 g of crystalline solid, m.p. 121°–123° C. $M+=361$.

REFERENCE EXAMPLE 233

Methyl 4-[([1,1'-Biphenyl]-2-carbonyl)amino]benzoate

A mixture of 10.0 g of [1,1'-biphenyl]-2-carboxylic acid in 75 ml of methylene chloride and 12.52 g of oxalyl chloride is stirred at room temperature for 18 hours. The volatiles are evaporated in vacuo to give 11.66 g of an oil. A 7.5 g portion of the above oil in 25 ml of methylene chloride is added dropwise to a solution of 4.53 g of methyl-4-aminobenzoate and 4.3 g of N,N-diisopropylethylamine in 100 ml of methylene chloride at 0° C. The reaction mixture is stirred at room temperature for 18 hours and washed with water, and saturated aqueous $NaHCO_3$ and the organic layer dried($Na_2SO_4$). The organic layer is passed through hydrous magnesium silicate and hexane added to the filtrate at the boil to give 8.38 g of the desired product as a crystalline solid, m.p. 163°–165° C.

REFERENCE EXAMPLE 234

4-[([1,1'-Biphenyl]-2-carbonyl)amino]benzoic Acid

A 3.15 g sample of methyl 4-[([1,1'-biphenyl]-2-carbonyl)amino]benzoate is refluxed for 8 hours in 100 ml of ethyl alcohol and 2.5 ml of 10N sodium hydroxide. The cooled reaction mixture is acidified with [[? acid]] and the desired product collected and dried to give 2.9 g of the desired product as a solid m.p. 246°–249° C. $M+H=318$.

REFERENCE EXAMPLE 235

4-[([1,1'-Biphenyl]-2-carbonyl)amino]benzoyl Chloride

A mixture of 1.39 g of 4-[([1,1'-biphenyl]-2-carbonyl)amino]benzoic acid in 2.0 ml of thionyl chloride is heated on a steam bath for 1 hour. Cold hexane is added and the crystalline solid collected and dried to give 1.34 g of the desired product, m.p. 118°–120° C.

REFERENCE EXAMPLE 236

2-(Phenylmethyl)benzoyl Chloride

A mixture of 5.0 g of 2-(phenylmethyl)benzoic acid in 5.0 ml of thionyl chloride is heated on a steam bath for 1 hour. The volatiles are evaporated in vacuo to give 5.74 g of the desired product as an oil. $M^+=227$ as methyl ester.

REFERENCE EXAMPLE 237

Methyl 4-[[2-(Phenylmethyl)benzoyl]amino]benzoate

To 3.03 g of methyl 4-aminobenzoate and 3.12 g of N,N-diisopropylethylamine in 75 ml of methylene chloride is added 5.54 g of 2-(phenylmethyl)benzoyl chloride and the reactants stirred at room temperature for 18 hours. The reaction mixture is washed with water, saturated aqueous NaHCO$_3$ and the organic layer dried(Na$_2$SO$_4$). The organic layer is passed through hydrous magnesium silicate two times and hexane added to the filtrate at the boil to give 5.04 g of the desired product as a crystalline solid, m.p. 138°–139° C.

REFERENCE EXAMPLE 238

Sodium 4-[[2-(Phenylmethyl)benzoyl]amino]benzoate

A mixture of 4.90 g of methyl 4-[[2-(phenylmethyl)benzoyl]amino]benzoate in 100 ml of absolute ethanol and 3.50 ml of 10N sodium hydroxide is heated on a steam bath for 3 hours. The aqueous phase is filtered and the resulting solid collected and dried to give 4.25 g of the desired product m.p. 340°–346° C.

REFERENCE EXAMPLE 239

4-[[2-(Phenylmethyl)benzoyl]amino]benzoic Acid

A mixture of 4.0 g sodium 4-[[2-(phenylmethyl)benzoyl]amino]benzoate is suspended in water and the pH adjusted to 5 with acetic acid. The solid is collected by filtration and dried at 80° C. in vacuo to give 3.75 g of the desired product, 246°–247° C. M$^+$=332.

REFERENCE EXAMPLE 240

4-[[2-(Phenylmethyl)benzoyl]amino]benzoyl Chloride

A mixture of 2.0 g of 4-[[2-(phenylmethyl)benzoyl]amino]benzoic acid in 2.0 ml of thionyl chloride is heated on a steam bath for 1 hour. The volatiles are evaporated in vacuo to give 1.53 g of the desired product as an oil. M$^+$=346 as methyl ester.

REFERENCE EXAMPLE 241

Methyl 4-[[(2-Phenylmethyl)benzoyl]amino]-2-chlorobenzoate

A mixture of 5.0 g of 2-(phenylmethyl)benzoic acid in 5.0 ml of thionyl chloride is heated on a steam bath for 1 hour. The volatiles are evaporated in Vacuo to give 5.70 g of an oil. A 2.85 g portion of the above oil in 25 ml of methylene chloride is added to a solution of 50 ml of methylene chloride containing 1.85 g of methyl 4-amino-2-chlorobenzoate and 1.65 g of N,N-diisopropylethylamine by stirring at room temperature for 18 hours. The reaction mixture is washed with water, saturated aqueous NaHCO$_3$ and the organic layer dried(Na$_2$SO$_4$). The organic layer is passed through hydrous magnesium silicate two times and hexane added to the filtrate at the boil to give 2.96 g of the desired product as a crystalline solid, m.p. 133°–135° C. M$^+$=380.

REFERENCE EXAMPLE 242

Methyl 4-[[(2-Phenylmethyl)benzoyl]amino]-3-methoxybenzoate

A solution of 2.85 g of 2-(phenylmethyl)benzoyl chloride in 25 ml of methylene chloride is added dropwise to an ice cold solution of 1.84 g of methyl 4-amino- 3-methoxybenzoate and 1.61 g of N,N-diisopropylethylamine in 50 ml of methylene chloride. The reaction mixture is stirred at room temperature for 18 hours and washed with water, saturated aqueous NaHCO$_3$ and the organic layer dried(Na$_2$SO$_4$). The organic layer is passed through a pad of hydrous magnesium silicate and hexane added at the boil to give 2.2 g of the desired product as a crystalline solid, m.p. 129°–131° C. M$^+$=376.

REFERENCE EXAMPLE 243

2-Chloro-4-[[(2-Phenylmethyl)benzoyl]amino]benzoic Acid

A mixture of 2.8 g of methyl 2-chloro-4-[[(2phenylmethyl)benzoyl]aminobenzoate in 75 ml of absolute ethanol and 1.84 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 2.6 g of the desired product as a crystalline solid, m.p. 184°–187° C. M$^+$H=366.

REFERENCE EXAMPLE 244

3-Methoxy-4-[[(2-phenylmethyl)benzoyl]amino] benzoic acid

A mixture of 2.05 g of methyl 4-[[(2-phenylmethyl)benzoyl]amino]-3-methoxybenzoate in 75 ml of absolute ethanol and 1.4 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 1.87 g of the desired product as a crystalline solid, m.p. 176°–178° C. M$^+$H=362.

REFERENCE EXAMPLE 245

3-Methoxy-4-[[(2-phenylmethyl)benzoyl]amino] benzoyl Chloride

A mixture of 1.71 g of 3-methoxy-4-[[(2-phenylmethyl)benzoyl]amino]benzoic acid in 2.0 ml of thionyl chloride is heated on a steam bath under Argon for 1 hour and hexane added. The resulting solid is collected and dried to give 1.71 g of the desired product as a crystalline solid, m.p. 130°–135° C. M$^+$=376 as the methyl ester.

REFERENCE EXAMPLE 246

[4'-(Trifluoromethyl)-1,1'-biphenyl]-2-carbonyl Chloride

A mixture of 5.0 g of 4°-(trifluoromethyl))[1,1°-biphenyl]-2-carboxylic acid in 5.0 ml of thionyl chloride is heated on a steam bath under Argon for 1 hour and hexane added. The resulting solid is collected and dried to give 5.36 g of the desired product as a colorless oil. M$^+$=280 as methyl ester.

REFERENCE EXAMPLE 247

Methyl 4-[((4'-trifluoromethyl)[1,1'-biphenyl]carbonyl))amino]benzoate

A solution of 3.13 g of [4'-(trifluoromethyl)[1,1'-biphenyl]-2-carbonyl chloride in 25 ml of methylene chloride is added dropwise to an ice cold solution of 1.84 g of methyl 4-aminobenzoate and 1.43 g of N,N-diisopropylethylamine in 50 ml of methylene chloride. The reaction mixture is stirred at room temperature for 18 hours and washed with water, saturated aqueous NaHCO$_3$ and the organic layer dried(Na$_2$SO$_4$). The organic layer is passed through a pad of hydrous magnesium silicate and hexane added at the boil to give 3.36 g of the desired product as a crystalline solid, m.p. 164°–165° C. M$^+$=396.

REFERENCE EXAMPLE 248

3-Methoxy-4-[((4'-(trifluoromethyl) [1,1'-biphenyl]-2-carbonyl)amino]benzoyl Chloride A mixture of 2.0 g of 3-methoxy-4-[((4'-(trifluoromethyl)[1,1'-biphenyl]-2-carbonyl)amino]benzoic acid in 20 ml of thionyl chloride is heated on a steam bath under Argon for 1 hour and hexane added. The resulting solid is collected and dried to give 1.92 g of the desired product as a crystalline solid, m.p. 136°–138° C.

REFERENCE EXAMPLE 249

3-Methoxy-4-[((4'-trifluoromethyl) [1,1'-biphenyl]-2- carbonyl)amino]benzoic Acid A mixture of 3.78 g of methyl 3-methoxy-4-[((4'-trifluoromethyl) [1,1'-biphenyl]-2-carbonyl)amino]benzoate in 75 ml of absolute ethanol and 2.20 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 3.49 g of the desired product as a crystalline solid, m.p. 213°–215° C.

REFERENCE EXAMPLE 250

Methyl 3-Methoxy-4-[((4'-trifluoromethyl) [1,1'-biphenyl]-2-carbonyl)amino]benzoate A solution of 3.56 g of [4'-(trifluoromethyl) [1,1'-biphenyl]-2-carbonyl chloride in 25 ml of methylene chloride is added dropwise to an ice cold solution of 1.81 g of methyl 4-amino-3-methoxybenzoate and 1.62 g of N,N-diisopropylethylamine in 50 ml of methylene chloride. The reaction mixture is stirred at room temperature for 18 hours and washed with water, saturated aqueous NaHCO$_3$ and the organic layer dried(Na$_2$SO$_4$). The organic layer is passed through a pad of hydrous magnesium silicate and hexane added at the boil to give 3.9 g of the desired product as a crystalline solid, m.p. 112°–113° C.

REFERENCE EXAMPLE 251

2-Chloro-4-[((4'-(trifluoromethyl)[1,1'-biphenyl]-2-carbonyl)amino]benzoyl Chloride A mixture of 1.39 g of 2-chloro-4-[((4'-(trifluoromethyl) [1,1'-biphenyl]-2-carbonyl)amino]benzoic acid in 2.0 ml of thionyl chloride is heated on a steam bath for 1 hour. The reaction mixture is concentrated to a residue in vacuo to a residue. Cold hexane is added to the residue and the solid collected and dried to give 1.39 g of the desired product.

REFERENCE EXAMPLE 252

2-Chloro-4-[((4'-(trifluoromethyl)[1,1'-biphenyl]-2-carbonyl)amino]benzoic acid

A mixture of 3.83 g of methyl 2-chloro-4-[((4'-(trifluoromethyl)[1,1'-biphenyl]-2-carbonyl)amino]benzoate in 75 ml of absolute ethanol and 2.20 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 3.42 g of the desired product as a crystalline solid, m.p. 187°–189° C.

REFERENCE EXAMPLE 253

Methyl 2-chloro-4-[((4'-(trifluoromethyl) [1,1'-biphenyl]-2-carbonyl)amino]benzoate A solution of 3.56 g of [4'-(trifluoromethyl)[1,1'-biphenyl]-2-carbonyl chloride in 10 ml of methylene chloride is added dropwise to an ice cold solution of 1.86 g of methyl 2-chloro-4-aminobenzoate and 1.6 g of N,N-diisopropylethylamine in 50 ml of methylene chloride. The reaction mixture is stirred at room temperature for 18 hours and washed with water, saturated aqueous NaHCO$_3$ and the organic layer dried(Na$_2$SO$_4$). The organic layer is passed through a pad of hydrous magnesium silicate (3X) and hexane added to the filtrate at the boil to give 4.0 g of the desired product as a crystalline solid, m.p. 130°–132° C.

REFERENCE EXAMPLE 254

4-[((4'-(Trifluoromethyl)[1,1'-biphenyl]carbonyl)amino]benzoic Acid

A mixture of 3.0 g of methyl 4-[((4'-(trifluoromethyl)[1,1'-biphenyl]-2-carbonyl)amino]benzoate in 75 ml of absolute ethanol and 2.0 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 2.93 g of the desired product as a crystalline solid, m.p. 243°–245° C. M$^+$=385.

REFERENCE EXAMPLE 255

Methyl 6-[[3-(2-Methylpyridinyl)carbonyl]amino] pyridine-3-carboxylate

To a stirred solution of 3 g of methyl 6-aminopyridine-3-carboxylate and 4 ml of N,N-diisopropylethylamine in 100 ml of methylene chloride is added dropwise a solution of 6.4 g of 2-methylpyridine- 3-carbonyl chloride in 25 ml of methylene chloride. The reaction mixture is stirred at room temperature for 2 hours and quenched with water. The organic layer is washed with water, dried(MgSO$_4$), filtered and evaporated in vacuo to a residue which is stirred with ether and the resulting solid collected and air dried to give 6.8 g of the desired product. M$^+$=390.

REFERENCE EXAMPLE 256

6-[[3-(2-methylpyridinyl)carbonyl]amino]pyridine-3- carboxylic Acid

To a solution of 6.5 g of methyl 6-[[3-(2-methylpyridinyl)carbonyl]amino]pyridine-3-carboxylate in 100 ml of 1:1 tetrahydrofuran:methyl alcohol is added 20 ml of 5N NaOH. The reaction mixture is stirred overnight and evaporated in vacuo to a residue. The residue is dissolved in water and neutralized with acetic acid. The separated solid is filtered and air-dried to give 3.0 g of the desired product. $M^+=257$.

REFERENCE EXAMPLE 257

Methyl 6-[((1,1'-Biphenyl]-2-carbonyl)amino]-pyridine-3-carboxylate

To a solution of 1.5 g of methyl 6-aminopyridine- 3-carboxylate in 100 ml of methylene chloride is added 3 ml of N,N-diisopropylethylamine at room temperature. To the stirred reaction mixture is slowly added a solution of 2.5 g of [1,1'-biphenyl]-2-carbonyl chloride. The reaction mixture is stirred at room temperature for 4 hours and then quenched with water. The organic layer is washed well with water and dried over anhydrous $MgSO_4$, filtered and evaporated in vacuo to a solid residue. The residue is stirred with ether, filtered and dried to give 3.0 g of the desired product:$M^+=332$.

REFERENCE EXAMPLE 258

6-[([1,1'-Biphenyl]-2-carbonyl)amino]pyridine-3-carboxylic Acid

To a stirred solution of 2.5 g of methyl 6-[([1,1'-Biphenyl] -2-carbonyl)amino]-pyridine-3 -carboxylate in 50 ml of 1:1 tetrahydrofuran:methanol is added 10 ml of 5N sodium hydroxide and the mixture stirred at room temperature for 16 hours. The reaction mixture is concentrated in vacuo to a residue which is dissolved in water and neutralized with acetic acid. The separated colorless solid is filtered and air dried to give 2.0 g of the desired product:$M^+=318$.

EXAMPLE 1

N-[4-[(4,5-Dihydropyrazolo[3,4-d]thieno[3,2-b] azepin-6(1H)-yl)carbonyl]phenyl]-2-chloro-4-fluorobenzamide To an ice bath cooled mixture of 296 mg of 6-( 4-aminobenzoyl)-1,4,5,6-tetrahydropyrazolo[3,4-d]thieno[3,2-b] azepine in 3.5 ml of methylene chloride is added 417 μl of triethylamine followed by a solution of 483 mg of 2-chloro-4-fluorobenzoyl chloride in 1.5 ml of methylene chloride. The reaction mixture is stirred at room temperature for 18 hours under argon. An additional 40 ml of methylene chloride is added followed by 20 ml of water. The organic layer is washed with 20 ml each of 2N citric acid, 1M $NaHCO_3$ and brine. The organic layer is dried ($Na_2SO_4$), filtered through hydrous magnesium silicate and the filtrate evaporated in vacuo to give a residue which is crystallized from ethyl acetate:hexane to give 520 mg of a white solid. To a suspension of 340 mg of the preceding compound in 5 ml methanol is added 1.2 ml of 1N NaOH. The reactants are stirred at room temperature for 1 hour. The reaction mixture is evaporated in vacuo to a residue which is diluted with 100 ml of ethyl acetate and filtered. The filtrate is washed with 30 ml each of water, brine and dried ($NaSO_4$). The organic layer is passed through a pad of hydrous magnesium silicate. The filtrate is evaporated in vacuo to a residue which is stirred with ethyl acetate:hexane to give 255 mg of white crystalline solid, m.p. 258°–266° C.

EXAMPLE 2

N-[4-[(4,5-Dihydropyrazolo[3,4-d]thieno[3,2-b] azepin-6(1H)-yl)carbonyl]phenyl]-5-fluoro-2-methylbenzamide To an ice bath cooled mixture of 297 mg of 6-( 4-aminobenzoyl)-1,4,5,6-tetrahydropyrazolo[3,4-d]thieno[3,2-b] azepine in 3.5 ml of methylene chloride is added 417 μl of triethylamine followed by a solution of 432 mg of 2-methyl-5-fluorobenzoyl chloride in 1.5 ml of methylene chloride. The reaction mixture is stirred at room temperature for 18 hours under argon. An additional 50 ml of methylene chloride is added followed by 20 ml of water. The organic layer is washed with 20 ml each of 2N citric acid, 1M $NaHCO_3$ and brine. The organic layer is dried ($Na_2SO_4$), filtered through hydrous magnesium silicate and the filtrate evaporated in vacuo to give 570 mg of a foam residue. To a suspension of 564 mg of the preceding compound in 4 ml of methanol and 4 ml of tetrahydrofuran is added 2.0 ml of 1N NaOH. The reactants are stirred at room temperature for 2 hours. The reaction mixture is diluted with 2 ml of 1N HCl and evaporated in vacuo to a residue which is partitioned between 50 ml of ethyl acetate and 20 ml of water. The resulting solid is collected, washed with ethyl acetate and dried to give 305 mg of the desired product as white crystals, m.p. 310°–312° C.

EXAMPLE 3

N-[4-[(4,5-Dihydropyrazolo[3,4-d]thieno[3,2-b] azepin-6(1H)-yl)carbonyl]-3-chlorophenyl]-5-fluoro-2 -methylbenzamide To an ice bath cooled mixture of 345 mg of 6( 2-chloro-4-aminobenzoyl)-1,4,5,6-tetrahydropyrazolo[3,4-d]thieno [3,2-b]azepine in 3.5 ml of methylene chloride is added 417 μl of triethylamine is added a solution of 432 mg of 2-methyl-5-fluorobenzoyl chloride in 1.5 ml of methylene chloride. The reaction mixture is stirred at room temperature for 18 hours under argon. An additional 40 ml of methylene chloride is added followed by 20 ml of water. The organic layer is washed with 20 ml each of 2N citric acid, 1M $NaHCO_3$ and brine. The organic layer is dried ($Na_2SO_4$), filtered through hydrous magnesium silicate and the filtrate evaporated in vacuo to give a foam residue. To a solution of 800 mg of the preceding compound in 4 ml methanol and 4 ml of tetrahydrofuran is added 2.7 ml of 1N NaOH. The reactants are stirred at room temperature for 1.5 hours. The reaction mixture is neutralized with 1N HCl and evaporated in vacuo to a residue which is diluted with 50 ml of methylene chloride and water and then filtered. The collected solid is dried at 60° C. to give 275 mg of the desired product as an off-white solid, m.p. 310°–312° C.

EXAMPLE 4

N-[4-[(4,5-Dihydropyrazolo[3,4-d]thieno[3,2-b] azepin- 6(1H)-yl)carbonyl]-3-chlorophenyl]-5-chloro-2 -fluorobenzamide To an ice bath cooled mixture of 345 mg of 6-( 2-chloro-4-aminobenzoyl)-1,4,5,6-tetrahydropyrazolo[3,4-d]thieno [3,2-b]azepine in 3.5 ml of methylene chloride under argon is added 417 μl of triethylamine followed by a solution of 482 mg of 2-fluoro-5-chlorobenzoyl chloride in 1.5 ml of methylene chloride. The reaction mixture is stirred at room temperature for 18 hours under argon. An additional 40 ml of methylene chloride is added followed by 20 ml of water. The organic layer is washed with 20 ml each of 2N citric acid, 1M NaHCO$_3$ and brine. The organic layer is dried (Na$_2$SO$_4$), filtered through hydrous magnesium silicate and the filtrate evaporated in vacuo to give 650 mg of the desired product as a solid residue. To a solution of 500 mg of the preceding compound in 4 ml methanol and 4 ml of tetrahydrofuran is added 1.51 ml of 1N NaOH. The reactants are stirred at room temperature for 18 hours. The reaction mixture is neutralized with 1N HCl and evaporated in vacuo to a residue which is diluted with 50 ml of chloroform and washed with water, brine and dried (Na$_2$SO$_4$). The organic layer is passed through a pad of hydrous magnesium silicate. The filtrte is evaporated in vacuo to a residue which is crystallized from ethyl acetate containing ethyl alcohol. The collected solid is dried to give 215 mg of the desired product as an off white solid, m.p. 282°–288° C.

EXAMPLE 5

N-[4-[[4,5-Dihydro-2-methylpyrazolo[3,4-d]thieno [3,2-b]azepin-6(2H)-yl]carbonyl]phenyl]-2,4-dichlorobenzamide To an ice bath cooled mixture of 290 mg of 2,4,5,6-tetrahydro-2-methyl-6-(4-aminobenzoyl)pyrazolo[3,4-d]thieno[3,2-b]azepine in 4.0 ml of methylene chloride and 2.0 ml of dioxane under argon is added 186 μl of triethylamine followed by 156 μl of 2,4-dichlorobenzoyl chloride. The reaction mixture is stirred at room temperature for 18 hours under argon. The reaction mixture is evaporated in vacuo to a residue which is dissolved in 50 ml of methylene chloride and washed with 20 ml each of water, 1N NaHCO$_3$, 2N citric acid and brine. The organic layer is dried (Na$_2$SO$_4$) and filtered. The filtrate is concentrated in vacuo to give a foam residue which is crystallized from ethyl acetate to give 330 mg of the desired product as a white crystalline solid, m.p. 265°–267° C.

EXAMPLE 6

N-[4-[[4,5-Dihydro-2-methylpyrazolo[3,4-d]thieno [3,2-b]azepin-6(2H)-yl]carbonyl]phenyl]cyclohexane carboxamide To an ice bath cooled mixture of 260 mg of 2,4,6-tetrahydro-2-methyl-6-(4-aminobenzoyl)pyrazolo[3,4-d]thieno[3,2-b]azepine in 4.0 ml of methylene chloride and 2.0 ml of dioxane under argon is added 168 μl of triethylamine followed by 134 μl of cyclohexanecarbonyl chloride. The reaction mixture is stirred at room temperature for 18 hours under argon. The reaction mixture is evaporated in vacuo to a residue which is dissolved in 60 ml of methylene chloride and washed with 20 ml each of water, 1N NaHCO$_3$, 2N citric acid and brine. The organic layer is dried (Na$_2$SO$_4$) and filtered. The filtrate is passed through a pad of hydrous magnesium silicate and the filtrate concentrated in vacuo to give a residue which is crystallized from ethyl acetate to give 185 mg of the desired product as a white crystalline solid, m.p. 240°–242° C.

EXAMPLE 7

N-[4-[[4,5-Dihydropyrazolo[3,4-d]thieno[3,2-b] azepin-6(2H)-yl]carbonyl]phenyl]-2-methylbenzamide To a solution of 400 mg of 6-(4-aminobenzoyl)- 1,4,5,6-tetrahydropyrazolo[3,4-d]thieno[3,2-b]azepine in 12.0 ml of dioxane under argon is added 65 mg of sodium hydride (60% in mineral oil). After stirring for 15 minutes, 176 μl of o-toluoyl chloride is added. The reaction mixture is stirred at room temperature for 18 hours under argon. The reaction mixture is evaporated in vacuo to a residue which is dissolved in 40 ml of methylene chloride and washed with 20 ml each of water and brine. The organic layer is dried (Na$_2$SO$_4$) and filtered. The filtrate is concentrated in vacuo to give a residue which is purified by chromatography on silica gel plates by elution with 1:1 ethyl acetate:hexane 100 mg of N-[4-[[4,5-dihydro-2-(2-methylbenzoyl)pyrazolo[4,3-d]thieno[3,2-b]azepin-6(2H)-yl]carbonyl]phenyl-2-methylbenzamide as a white foam and 200 mg of the product as a white foam.

EXAMPLE 8

N-[4-[(4,5-Dihydropyrazolo[3,4-d]pyrido[3,2-b] azepin-6(1H)-yl)carbonyl]phenyl]-5-fluoro-2-methylbenzamide As described for Example 2, 2 mmol of 6-(4-aminobenzoyl)- 1,4,5,6-tetrahydropyrazolo[3,4-b]pyrido[ 3,2-b] azepine is reacted with 2.2 mmol of 5-fluoro-2-methylbenzoyl chloride to give the product as a solid.

As described for Example 8, the following compounds are prepared.

EXAMPLE 9

N-[4-[(4,5-Dihydropyrazolo[3,4-d]pyrido[3,2-b] azepin-6(1H)-yl)carbonyl]phenyl]-2-fluoro-5-chlorobenzamide

EXAMPLE 10

N-[4-[(4,5-Dihydropyrazolo[3,4-d]pyrido[3,2-b] azepin-6(1H)-yl)carbonyl]-3-chlorophenyl]-5-fluoro-2-methylbenzamide

EXAMPLE 11

N-[4-[(4,5-Dihydropyrazolo[3,4-d]pyrido[3,2-b] azepin-6(1H)-yl)carbonyl]phenyl]-2-chloropyridine-3-carboxamide

EXAMPLE 12

N-[5-[(4,5-Dihydropyrazolo[3,4-d]pyrido[3,2-b] azepin-6(1H)-yl)carbonyl]-2-pyridinyl]-5-fluoro-2-methylbenzamide To a solution of 2 mmol 1,4,5,6-tetrahydropyrazolo[3,4-d]pyrido[3,2-b]azepine and 10 mmol of triethylamine in 25 ml of dichloromethane is added 4.2 mmol of 6-[(5-fluoro-2-methylbenzoyl)amino]pyridine-3-carbonyl chloride. After stirring over the mixture is worked-up as described for Example 1 and the initial solid treated with 1N NaOH in methanol as described for Example 1 to give the product as a solid.

EXAMPLE 13

N-[5-[(4,5-Dihydropyrazolo[3,4-d]thieno[3,2-b]azepin-6(1H)-yl)carbonyl]-2-pyridinyl]-5-fluoro-2-methylbenzamide To a solution of 2 mmol of 1,4,5,6-tetrahydropyrazolo[3,4-d]thieno[3,2-b]azepine and 10 mmol of triethylamine in 25 ml of dichloromethane is added 4.2 mmol of 6-[(5-fluoro-2-methylbenzoyl)amino]pyridine-3-carbonyl chloride. After stirring overnight, the mixture is worked-up as described for Example 1, and the initial solid treated with 1N NaOH as described for Example 1 to give the product as a solid.

EXAMPLE 14

N-[4-[(4,10-Dihydro-5H-pyrido[3,2-b]thieno[2,3-e]azepin-5-yl-carbonyl]-3-chlorophenyl]-5-fluoro-2-methylbenzamide To a solution of 2 mmol of 5-(2-chloro-4-aminobenzoyl)-4,10-dihydro-5H-pyrido[3,2-b]thieno[2,3-e]azepine and 10 mmol of triethylamine in 25 ml of dichloromethane is added 2.1 mmol of 5-fluoro-2-methylbenzoyl chloride. After stirring at room temperature overnight, the mixture is washed with $H_2O$, 1M $NaHCO_3$ and brine. The solution is dried ($Na_2SO_4$) and the solvent removed to give the product as a solid.

EXAMPLE 15

N-[4-[(6,10-Dihydro-5H-pyrido[3,2-b]thieno[3,2-e]azepin-5-yl)carbonyl]-3-chlorophenyl]-5-fluoro-2-methylbenzamide To a solution of 2 mmol of 5-(2-chloro-4-aminobenzoyl)-6,10-dihydro-5H-pyrido[3,2-b]thieno[3,2-e]azepine and 10 mmol of triethylamine in 25 ml of dichloromethane is added 2.1 mmol of 5-fluoro-2-methylbenzoyl chloride. After stirring at room temperature for 16 hours, the solution is washed with $H_2O$, 1M $NaHCO_3$ and brine. The solution is dried ($Na_2SO_4$) and the solvent removed to give the product as a solid.

EXAMPLE 16

N-[4-[(4,5-Dihydropyrazolo[3,4-d]pyrido[2,3-b]azepin-6(1H)-yl)carbonyl]phenyl]-5-fluoro-2-methylbenzamide As described for Example 1, a solution of 2 mmol of 4-(4-aminobenzoyl)-4,5-dihydropyrazolo[3,4-d]pyrido[2,3-b]azpeine and 10 mmol of triethylamine is stirred with 4.2 mmol of 5-fluoro-2-methylbenzoyl chloride in dichloromethane to give a solid. The solid is stirred with 1N NaOH in methanol and the mixture worked-up as for Example 1 to give the product as a solid.

EXAMPLE 17

N-[5-[(4,5-Dihydropyrazolo[3,4-d]pyrido[2,3-b]azepin-6(1H)-yl)carbonyl]-2-pyridinyl]-5-fluoro-2-methylbenzamide As described for Example 13, 4,5-dihydropyrazolo[3,4-d]pyrido[2,3-b]azepine is reacted with 6-(5-fluoro-2-methylbenzoyl)amino]pyridine-3-carbonyl chloride to give the product as a solid.

EXAMPLE 18

N-[4-[(4,5-Dihydropyrazolo[3,4-d]pyrido[2,3-b]azepin-6(1H)-yl)carbonyl]phenyl][1,1'-biphenyl]-2-carboxamide As described for Example 1, a solution of 2 mmol of 4-(4-aminobenzoyl)-4,5-dihydropyrazolo[3,4-d]pyrido[2,3-b]azepine and 10 mmol of triethylamine is stirred with [1,1'-biphenyl]-2-carbonyl chloride in dichloromethane for 16 hours at room temperature. The initial solid is stirred with 1N NaOH in methanol as described in Example 1 to give the product as a solid.

EXAMPLE 19

N-[5-[(4,5-Dihydropyrazolo[3,4-d]pyrido[2,3-b]azepin-6(1H)-yl)carbonyl]-2-pyridinyl][1,1'-biphenyl]-2-carboxamide As described for Example 13, a solution of 2.0 mmol of 4,5-dihydropyrazolo[3,4-d]pyrido[2,3-b]azepine and 10 mmol of triethylamine is stirred with 4.2 mmol of 6-[(5-fluoro-2-methylbenzoyl)amino]pyridine-3-carbonyl chloride in dichloromethane at room temperature for 16 hours to give the product as a solid.

EXAMPLE 20

N-[4-[(4,5-Dihydropyrazolo[3,4-d]pyrido[2,3-b]azepin-6(1H)-yl)carbonyl]-3-chlorophenyl]-5-fluoro-2-methylbenzamide As described for Example 2, a solution of 2 mmol of 4-(2-chloro-4-aminobenzoyl)-4,5-dihydropyrazolo[3,4-d]pyrido[2,3-b]azepine and 10 mmol of triethylamine is stirred with 4.2 mmol of 5-fluoro-2-methylbenzoyl chloride in dichloromethane at room temperature to give a solid. The solid is stirred with 1N NaOH in methanol as described for Example 2 to give the product as a solid.

The following compounds are prepared as described for Example 1 (Table A).

TABLE A

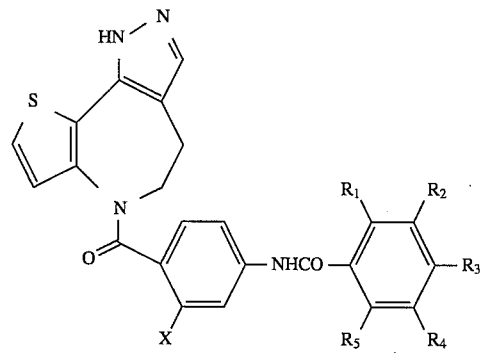

| Ex. No. | $R_1$ | $R_2$ | $R_3$ | $R_4$ | $R_5$ | X |
|---|---|---|---|---|---|---|
| 21 | Cl | H | H | H | H | H |
| 22 | Cl | H | H | H | H | Cl |
| 23 | Cl | H | Cl | H | H | H |
| 24 | Cl | H | Cl | H | H | Cl |
| 25 | Cl | H | H | Cl | H | H |
| 26 | Cl | H | H | Cl | H | Cl |
| 27 | F | H | H | Cl | H | H |
| 28 | F | H | H | Cl | H | Cl |
| 29 | $CH_3$ | H | H | H | H | H |

TABLE A-continued

| Ex. No. | R₁ | R₂ | R₃ | R₄ | R₅ | X |
|---|---|---|---|---|---|---|
| 30 | CH₃ | H | H | H | H | Cl |
| 31 | CH₃ | CH₃ | H | H | H | H |
| 32 | CH₃ | CH₃ | H | H | H | Cl |
| 33 | OCH₃ | H | H | H | H | H |
| 34 | OCH₃ | H | H | H | H | Cl |
| 35 | OCF₃ | H | H | H | H | H |
| 36 | OCF₃ | H | H | H | H | Cl |
| 37 | Cl | H | H | H | Cl | H |
| 38 | Cl | H | H | H | Cl | Cl |
| 39 | CH₃ | H | H | H | CH₃ | H |
| 40 | CH₃ | H | H | H | CH₃ | Cl |
| 41 | S—CH₃ | H | H | H | H | H |
| 42 | S—CH₃ | H | H | H | H | Cl |
| 43 | CF₃ | H | H | H | H | H |
| 44 | CF₃ | H | H | H | H | Cl |
| 45 | CF₃ | H | F | H | H | H |
| 46 | CF₃ | H | F | H | H | Cl |
| 47 | Cl | H | H | F | H | H |
| 48 | Cl | H | H | F | H | Cl |
| 49 | NO₂ | H | H | H | H | H |
| 50 | NO₂ | H | H | H | H | Cl |
| 51 | NH₂ | H | H | H | H | H |
| 52 | NH₂ | H | H | H | H | Cl |
| 53 | N(CH₃)₂ | H | H | H | H | H |
| 54 | N(CH₃)₂ | H | H | H | H | Cl |
| 55 | OCH₃ | H | H | Cl | H | H |
| 56 | OCH₃ | H | H | H | H | Cl |
| 57 | Cl | Cl | H | H | H | H |
| 58 | Cl | Cl | H | H | H | Cl |
| 59 | CF₃ | H | H | H | F | H |
| 60 | Cl | Cl | H | Cl | H | H |
| 61 | NHCH₃ | H | H | H | H | H |
| 62 | NHCH₃ | H | H | H | H | Cl |
| 63 | H | CF₃ | H | H | H | H |
| 64 | H | CF₃ | H | H | H | Cl |

As described for Example 1, the following compounds are prepared (Table B).

TABLE B

| Ex. No | R₁ | R₂ | R₃ | R₄ | R₅ | X |
|---|---|---|---|---|---|---|
| 65 | CH₃ | H | H | H | H | H |
| 66 | CH₃ | H | H | F | H | H |
| 67 | CH₃ | F | H | H | H | H |
| 68 | H | OCH₃ | OCH₃ | OCH₃ | H | H |
| 69 | Cl | H | H | H | H | H |
| 70 | F | H | F | H | H | H |
| 71 | Br | H | H | H | H | H |
| 72 | Cl | H | F | H | H | H |
| 73 | Ph | H | H | H | H | H |
| 74 | Cl | H | H | Br | H | H |
| 75 | CH₃ | H | H | H | H | Br |
| 76 | CH₃ | H | H | F | H | Cl |
| 77 | Cl | H | H | Cl | H | H |
| 78 | CH₃ | CH₃ | H | H | H | H |
| 79 | Cl | H | H | F | H | H |
| 80 | Cl | H | H | CF₃ | H | H |
| 81 | Cl | H | H | H | F | H |
| 82 | Cl | H | H | H | Cl | H |
| 83 | Cl | H | H | F | H | H |
| 84 | (2-pyridyl) | H | H | H | H | H |
| 85 | (2-thienyl) | H | H | H | H | H |
| 86 | CH₃ | H | H | H | CH₃ | H |
| 87 | Cl | H | H | F | H | Cl |
| 88 | Cl | H | F | H | H | Cl |
| 89 | Cl | Cl | H | H | H | H |
| 90 | Cl | H | H | Cl | H | H |
| 91 | —OCH₃ | H | H | H | H | H |
| 92 | OCF₃ | H | H | H | H | H |
| 93 | —CF₃ | H | H | H | H | H |
| 94 | Cl | Cl | H | Cl | H | H |
| 95 | —SCH₃ | H | H | H | H | H |
| 96 | Cl | H | NO₂ | H | H | H |
| 97 | CH₃ | H | H | CH₃ | H | H |
| 98 | F | H | H | Cl | H | H |
| 99 | Cl | H | H | NH₂ | H | H |
| 100 | F | CF₃ | H | H | H | H |
| 101 | —OCH₃ | H | H | Cl | H | H |
| 102 | Cl | H | H | -SCH₃ | H | H |
| 103 | F | H | H | H | CF₃ | H |
| 104 | F | H | CF₃ | H | H | H |
| 105 | CF₃ | H | F | H | H | H |

TABLE B-continued

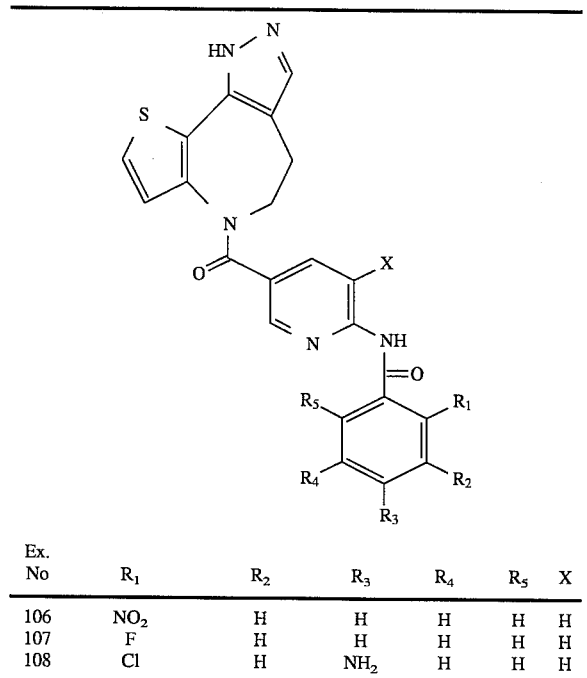

| Ex. No | $R_1$ | $R_2$ | $R_3$ | $R_4$ | $R_5$ | X |
|---|---|---|---|---|---|---|
| 106 | $NO_2$ | H | H | H | H | H |
| 107 | F | H | H | H | H | H |
| 108 | Cl | H | $NH_2$ | H | H | H |

The following compounds are prepared as described in Example 2 (Table C).

TABLE C

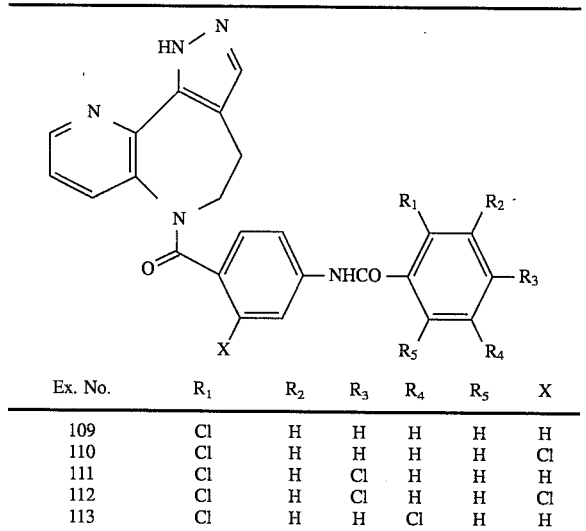

| Ex. No. | $R_1$ | $R_2$ | $R_3$ | $R_4$ | $R_5$ | X |
|---|---|---|---|---|---|---|
| 109 | Cl | H | H | H | H | H |
| 110 | Cl | H | H | H | H | Cl |
| 111 | Cl | H | Cl | H | H | H |
| 112 | Cl | H | Cl | H | H | Cl |
| 113 | Cl | H | H | Cl | H | H |

TABLE C-continued

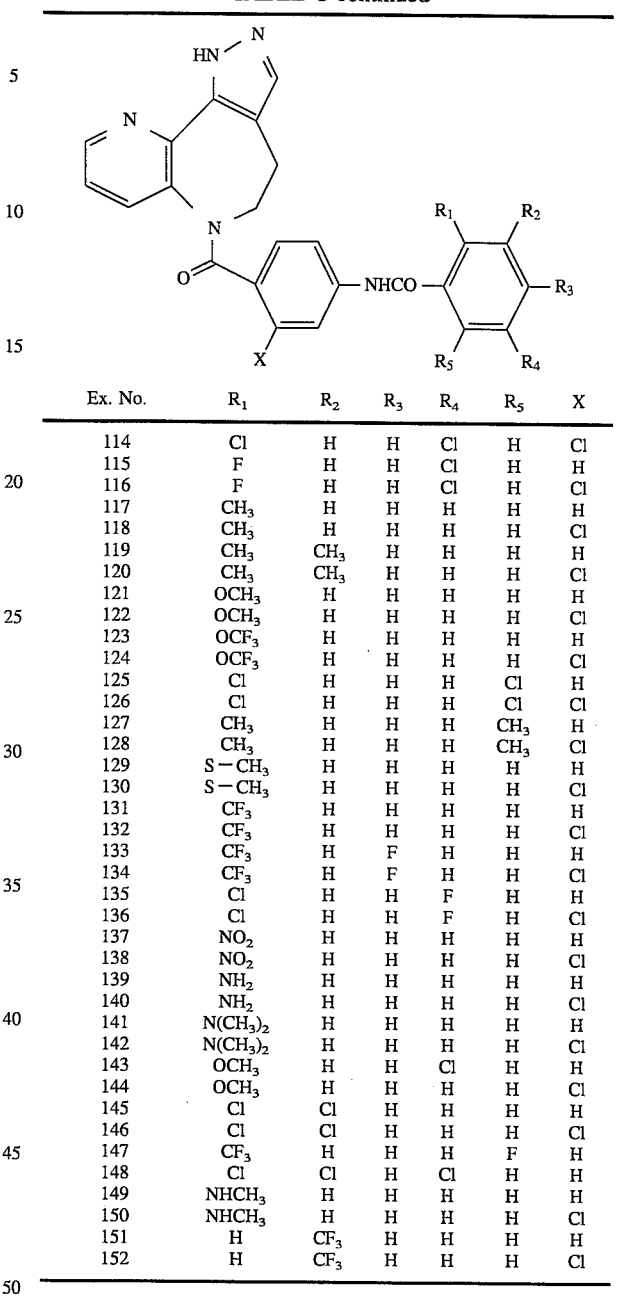

| Ex. No. | $R_1$ | $R_2$ | $R_3$ | $R_4$ | $R_5$ | X |
|---|---|---|---|---|---|---|
| 114 | Cl | H | H | Cl | H | Cl |
| 115 | F | H | H | Cl | H | H |
| 116 | F | H | H | Cl | H | Cl |
| 117 | $CH_3$ | H | H | H | H | H |
| 118 | $CH_3$ | H | H | H | H | Cl |
| 119 | $CH_3$ | $CH_3$ | H | H | H | H |
| 120 | $CH_3$ | $CH_3$ | H | H | H | Cl |
| 121 | $OCH_3$ | H | H | H | H | H |
| 122 | $OCH_3$ | H | H | H | H | Cl |
| 123 | $OCF_3$ | H | H | H | H | H |
| 124 | $OCF_3$ | H | H | H | H | Cl |
| 125 | Cl | H | H | H | Cl | H |
| 126 | Cl | H | H | H | Cl | Cl |
| 127 | $CH_3$ | H | H | H | $CH_3$ | H |
| 128 | $CH_3$ | H | H | H | $CH_3$ | Cl |
| 129 | $S-CH_3$ | H | H | H | H | H |
| 130 | $S-CH_3$ | H | H | H | H | Cl |
| 131 | $CF_3$ | H | H | H | H | H |
| 132 | $CF_3$ | H | H | H | H | Cl |
| 133 | $CF_3$ | H | F | H | H | H |
| 134 | $CF_3$ | H | F | H | H | Cl |
| 135 | Cl | H | H | F | H | H |
| 136 | Cl | H | H | F | H | Cl |
| 137 | $NO_2$ | H | H | H | H | H |
| 138 | $NO_2$ | H | H | H | H | Cl |
| 139 | $NH_2$ | H | H | H | H | H |
| 140 | $NH_2$ | H | H | H | H | Cl |
| 141 | $N(CH_3)_2$ | H | H | H | H | H |
| 142 | $N(CH_3)_2$ | H | H | H | H | Cl |
| 143 | $OCH_3$ | H | H | Cl | H | H |
| 144 | $OCH_3$ | H | H | Cl | H | Cl |
| 145 | Cl | Cl | H | H | H | H |
| 146 | Cl | Cl | H | H | H | Cl |
| 147 | $CF_3$ | H | H | H | F | H |
| 148 | Cl | Cl | H | Cl | H | H |
| 149 | $NHCH_3$ | H | H | H | H | H |
| 150 | $NHCH_3$ | H | H | H | H | Cl |
| 151 | H | $CF_3$ | H | H | H | H |
| 152 | H | $CF_3$ | H | H | H | Cl |

As described for Example 2, the following compounds are prepared.

TABLE D

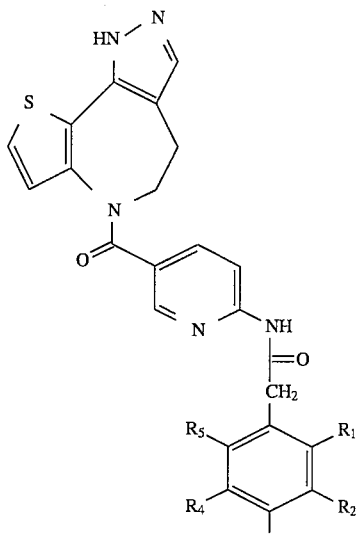

A = C or N

| Ex. No. | $R_1$ | $R_2$ | $R_3$ | $R_4$ | $R_5$ | X |
|---|---|---|---|---|---|---|
| 153 | CH$_3$ | H | H | H | H | C |
| 154 | CH$_3$ | H | H | H | H | N |
| 155 | CH$_3$ | H | H | CH$_3$ | H | C |
| 156 | Cl | H | H | H | H | C |
| 157 | Cl | H | H | H | Cl | C |
| 158 | Cl | H | H | H | H | N |
| 159 | Cl | H | Cl | H | H | C |
| 160 | Cl | H | Cl | H | H | N |
| 161 | Cl | H | H | F | H | C |
| 162 | —OCH$_3$ | H | H | H | H | C |
| 163 | —OCH$_3$ | H | H | H | H | N |
| 164 | —OCH$_3$ | H | H | Cl | H | C |
| 165 | —OCH$_3$ | H | H | —OCH$_3$ | H | C |
| 166 | —OCH$_3$ | H | H | —OCH$_3$ | H | N |
| 167 | —OCH$_3$ | H | H | Cl | H | N |
| 168 | CH$_3$ | F | H | H | H | C |
| 169 | H | F | H | H | H | N |
| 170 | CH$_3$ | —CH$_3$ | H | H | H | C |
| 171 | Cl | Cl | H | H | H | C |
| 172 | Cl | Cl | H | H | H | N |
| 173 | F | Cl | H | H | H | C |
| 174 | F | H | Cl | H | H | N |
| 175 | —SCH$_3$ | H | H | H | H | C |
| 176 | —SCH$_3$ | H | H | H | H | N |
| 177 | F | H | H | Cl | H | C |
| 178 | F | H | H | Cl | H | N |
| 179 | F | H | H | H | Cl | C |
| 180 | H | —CF$_3$ | H | H | H | C |
| 181 | H | —CF$_3$ | H | H | H | N |
| 182 | CF$_3$ | H | H | H | H | C |
| 183 | —OCF$_3$ | H | F | H | H | C |
| 184 | CH$_3$ | H | H | F | H | C |

As described for Example 5, the following compounds are prepared (Table E).

TABLE E

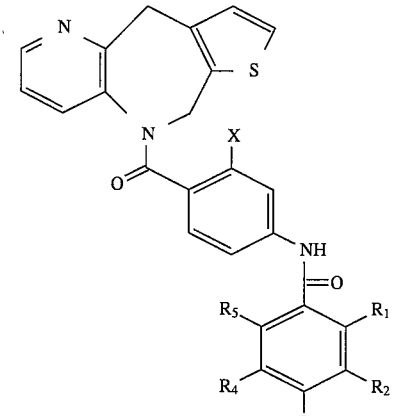

| Ex. No | $R_1$ | $R_2$ | $R_3$ | $R_4$ | $R_5$ | X |
|---|---|---|---|---|---|---|
| 185 | CH$_3$ | H | H | H | H | H |
| 186 | CH$_3$ | H | H | F | H | H |
| 187 | CH$_3$ | F | H | H | H | H |
| 188 | CH$_2$Ph | H | H | H | H | Cl |
| 189 | Cl | H | H | H | H | H |
| 190 | F | H | F | H | H | H |
| 191 | Br | H | H | H | H | H |
| 192 | Cl | H | F | H | H | H |
| 193 | Ph | H | H | H | H | H |
| 194 | Cl | H | H | Br | H | H |
| 195 | CH$_3$ | H | H | H | H | Br |
| 196 | CH$_3$ | H | H | F | H | Cl |
| 197 | Cl | H | H | Cl | H | H |
| 198 | CH$_3$ | CH$_3$ | H | H | H | H |
| 199 | Cl | H | H | F | H | H |
| 200 | Cl | H | H | CF$_3$ | H | H |
| 201 | Cl | H | H | H | F | H |
| 202 | Cl | H | H | H | Cl | H |
| 203 | Cl | H | H | F | H | H |
| 204 | ![2-pyridyl] | H | H | H | H | H |
| 205 | ![2-thienyl] | H | H | H | H | H |
| 206 | CH$_3$ | H | H | H | CH$_3$ | H |
| 207 | Cl | H | H | F | H | Cl |
| 208 | Cl | H | F | H | H | Cl |
| 209 | Cl | Cl | H | H | H | H |
| 210 | Cl | H | H | Cl | H | H |
| 211 | —OCH$_3$ | H | H | H | H | H |
| 212 | OCF$_3$ | H | H | H | H | H |
| 213 | —CF$_3$ | H | H | H | H | H |
| 214 | Cl | Cl | H | Cl | H | H |
| 215 | —SCH$_3$ | H | H | H | H | H |
| 216 | Cl | H | NO$_2$ | H | H | H |
| 217 | CH$_3$ | H | H | CH$_3$ | H | H |
| 218 | F | H | H | Cl | H | H |
| 219 | Cl | H | H | NH$_2$ | H | H |
| 220 | F | CF$_3$ | H | H | H | H |
| 221 | —OCH$_3$ | H | H | Cl | H | H |
| 222 | Cl | H | H | —SCH$_3$ | H | H |
| 223 | F | H | H | H | CF$_3$ | H |
| 224 | F | H | CF$_3$ | H | H | H |
| 225 | CF$_3$ | H | F | H | H | H |
| 226 | NO$_2$ | H | H | H | H | H |
| 227 | F | H | H | H | H | H |
| 228 | Cl | H | NH$_2$ | H | H | H |

As described for Example 5, the following compounds are prepared (Table F).

TABLE F

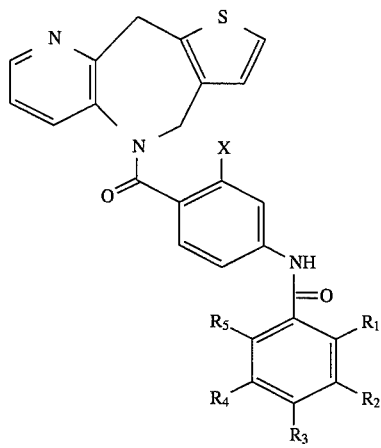

| Ex. No | R₁ | R₂ | R₃ | R₄ | R₅ | X |
|---|---|---|---|---|---|---|
| 229 | CH₃ | H | H | H | H | H |
| 230 | CH₃ | H | H | F | H | H |
| 231 | CH₃ | F | H | H | H | H |
| 232 | CH₂Ph | H | H | H | H | Cl |
| 233 | Cl | H | H | H | H | H |
| 234 | F | H | F | H | H | H |
| 235 | Br | H | H | H | H | H |
| 236 | Cl | H | F | H | H | H |
| 237 | Ph | H | H | H | H | H |
| 238 | Cl | H | H | Br | H | H |
| 239 | CH₃ | H | H | H | H | Br |
| 240 | CH₃ | H | H | F | H | Cl |
| 241 | Cl | H | H | Cl | H | H |
| 242 | CH₃ | CH₃ | H | H | H | H |
| 243 | Cl | H | H | F | H | H |
| 244 | Cl | H | H | CF₃ | H | H |
| 245 | Cl | H | H | H | F | H |
| 246 | Cl | H | H | H | Cl | H |
| 247 | Cl | H | H | F | H | H |
| 248 | 2-pyridyl | H | H | H | H | H |
| 249 | 2-thienyl | H | H | H | H | H |
| 250 | CH₃ | H | H | H | CH₃ | H |
| 251 | Cl | H | H | F | H | Cl |
| 252 | Cl | H | F | H | H | Cl |
| 253 | Cl | Cl | H | H | H | H |
| 254 | Cl | H | H | Cl | H | H |
| 255 | —OCH₃ | H | H | H | H | H |
| 256 | OCF₃ | H | H | H | H | H |
| 257 | —CF₃ | H | H | H | H | H |
| 258 | Cl | Cl | H | Cl | H | H |
| 259 | —SCH₃ | H | H | H | H | H |
| 260 | Cl | H | NO₂ | H | H | H |
| 261 | CH₃ | H | H | CH₃ | H | H |
| 262 | F | H | H | Cl | H | H |
| 263 | Cl | H | H | NH₂ | H | H |
| 264 | F | CF₃ | H | H | H | H |
| 265 | —OCH₃ | H | H | Cl | H | H |
| 266 | Cl | H | H | —SCH₃ | H | H |
| 267 | F | H | H | H | CF₃ | H |
| 268 | F | H | CF₃ | H | H | H |
| 269 | CF₃ | H | F | H | H | H |
| 270 | NO₂ | H | H | H | H | H |

TABLE F-continued

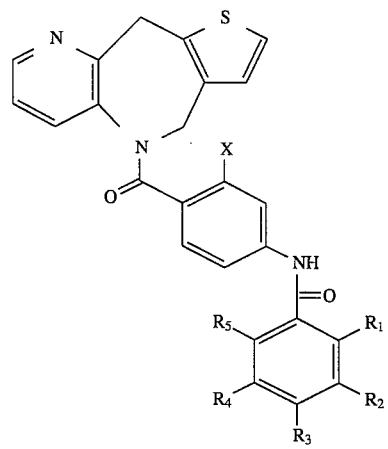

| Ex. No | R₁ | R₂ | R₃ | R₄ | R₅ | X |
|---|---|---|---|---|---|---|
| 271 | F | H | H | H | H | H |
| 272 | Cl | H | NH₂ | H | H | H |

As described for Example 2, the following compounds are prepared (Table G).

TABLE G

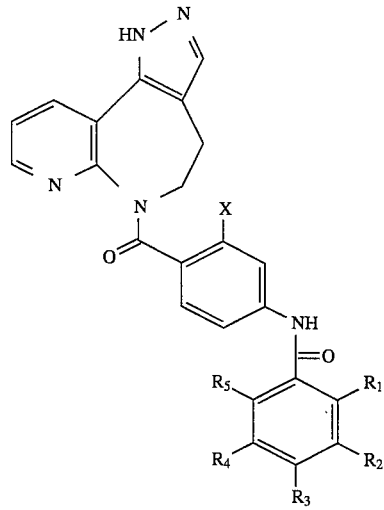

| Ex. No | R₁ | R₂ | R₃ | R₄ | R₅ | X |
|---|---|---|---|---|---|---|
| 273 | CH₃ | H | H | H | H | H |
| 274 | CH₃ | H | H | F | H | H |
| 275 | CH₃ | F | H | H | H | H |
| 276 | CH₂Ph | H | H | H | H | Cl |
| 277 | Cl | H | H | H | H | H |
| 278 | F | H | F | H | H | H |
| 279 | Br | H | H | H | H | H |
| 280 | Cl | H | F | H | H | H |
| 281 | Ph | H | H | H | H | H |
| 282 | Cl | H | H | Br | H | H |
| 283 | CH₃ | H | H | H | H | Br |
| 284 | CH₃ | H | H | F | H | Cl |
| 285 | Cl | H | H | Cl | H | H |
| 286 | CH₃ | CH₃ | H | H | H | H |
| 287 | Cl | H | H | F | H | H |
| 288 | Cl | H | H | CF₃ | H | H |
| 289 | Cl | H | H | H | F | H |
| 290 | Cl | H | H | H | Cl | H |

TABLE G-continued

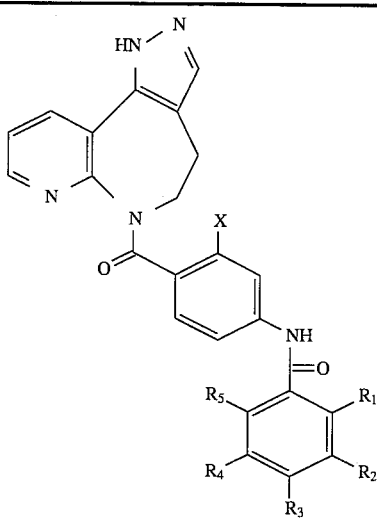

| Ex. No | R1 | R2 | R3 | R4 | R5 | X |
|---|---|---|---|---|---|---|
| 291 | Cl | H | H | F | H | H |
| 292 | 2-pyridyl | H | H | H | H | H |
| 293 | 2-thienyl | H | H | H | H | H |
| 294 | CH3 | H | H | H | CH3 | H |
| 295 | Cl | H | H | F | H | Cl |
| 296 | Cl | H | F | H | H | Cl |
| 297 | Cl | Cl | H | H | H | H |
| 298 | Cl | H | H | Cl | H | H |
| 299 | —OCH3 | H | H | H | H | H |
| 300 | OCF3 | H | H | H | H | H |
| 301 | —CF3 | H | H | H | H | H |
| 302 | Cl | Cl | H | Cl | H | H |
| 303 | —SCH3 | H | H | H | H | H |
| 304 | Cl | H | NO2 | H | H | H |
| 305 | CH3 | H | H | CH3 | H | H |
| 306 | F | H | H | Cl | H | H |
| 307 | Cl | H | H | NH2 | H | H |
| 308 | F | CF3 | H | H | H | H |
| 309 | —OCH3 | H | H | Cl | H | H |
| 310 | Cl | H | H | —SCH3 | H | H |
| 311 | F | H | H | H | CF3 | H |
| 312 | F | H | —CF3 | H | H | H |
| 313 | CF3 | H | F | H | H | H |
| 314 | NO2 | H | H | H | H | H |
| 315 | F | H | H | H | H | H |
| 316 | Cl | H | NH2 | H | H | H |

As described for Example 2, the following compounds are prepared (Table H).

TABLE H

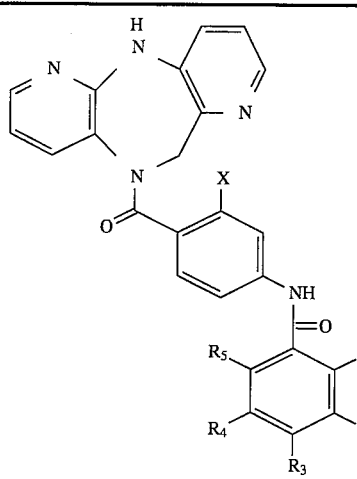

| Ex. No | R1 | R2 | R3 | R4 | R5 | X |
|---|---|---|---|---|---|---|
| 317 | CH3 | H | H | H | H | H |
| 318 | CH3 | H | H | F | H | H |
| 319 | CH3 | F | H | H | H | H |
| 320 | CH2Ph | H | H | H | H | Cl |
| 321 | Cl | H | H | H | H | H |
| 322 | F | H | F | H | H | H |
| 323 | Br | H | H | H | H | H |
| 324 | Cl | H | F | H | H | H |
| 325 | Ph | H | H | H | H | H |
| 326 | Cl | H | H | Br | H | H |
| 327 | CH3 | H | H | H | H | Br |
| 328 | CH3 | H | H | F | H | Cl |
| 329 | Cl | H | H | Cl | H | H |
| 330 | CH3 | CH3 | H | H | H | H |
| 331 | Cl | H | H | F | H | H |
| 332 | Cl | H | H | CF3 | H | H |
| 333 | Cl | H | H | H | F | H |
| 334 | Cl | H | H | H | Cl | H |
| 335 | Cl | H | H | F | H | H |
| 336 | 2-pyridyl | H | H | H | H | H |
| 337 | 2-thienyl | H | H | H | H | H |
| 338 | CH3 | H | H | H | CH3 | H |
| 339 | Cl | H | H | F | H | Cl |
| 340 | Cl | H | F | H | H | Cl |
| 341 | Cl | Cl | H | H | H | H |
| 342 | Cl | H | H | Cl | H | H |
| 343 | —OCH3 | H | H | H | H | H |
| 344 | OCF3 | H | H | H | H | H |
| 345 | —CF3 | H | H | H | H | H |
| 346 | Cl | Cl | H | Cl | H | H |
| 347 | —SCH3 | H | H | H | H | H |
| 348 | —Cl | H | NO2 | H | H | H |
| 349 | CH3 | H | H | CH3 | H | H |
| 350 | F | H | H | Cl | H | H |
| 351 | Cl | H | H | NH2 | H | H |
| 352 | F | CF3 | H | H | H | H |
| 353 | —OCH3 | H | H | Cl | H | H |
| 354 | Cl | H | H | —SCH3 | H | H |
| 355 | F | H | H | H | CF3 | H |
| 356 | F | H | CF3 | H | H | H |
| 357 | CF3 | H | F | H | H | H |

TABLE H-continued

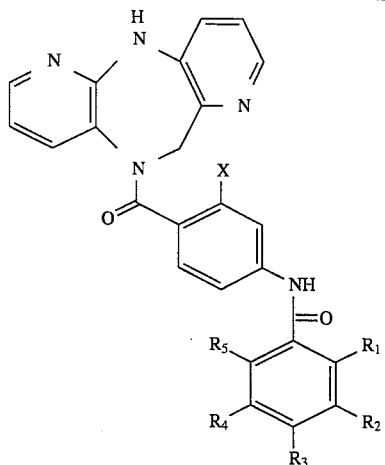

| Ex. No | R₁ | R₂ | R₃ | R₄ | R₅ | X |
|---|---|---|---|---|---|---|
| 358 | $NO_2$ | H | H | H | H | H |
| 359 | F | H | H | H | H | H |
| 360 | Cl | H | $NH_2$ | H | H | H |

EXAMPLE 361

N-[4-[(4,5-Dihydro-2-methylpyrazolo[3,4-d]thieno [3,2-b]azepin-6(2H)-yl)carbonyl]phenyl]-2-methylbenzamide As described for Example 5, 2,4,5,6-tetrahydro- 2-methyl- 6-(4-aminobenzoyl)pyrazolo[3,4-d]thieno[3,2-b] azepine is reacted with 2-methylbenzoyl chloride to give the product as crystals (from ethyl acetate), m.p. 257°–260° C.

EXAMPLE 362

N-[4-[(4,5-Dihydropyrazolo[3,4-d]thieno[3,2-b] azepin-6(1H)-yl)carbonyl]phenyl][1,1'-biphenyl]-2-carboxamide As described for Example 2, 6-(4-aminobenzoyl)- 1,4,5, 6-tetrahydropyrazolo[3,4-d]thieno[3,2-b]azepine (297 mg) is reacted with 0.542 g of [1,1'-biphenyl]-2-carbonyl chloride to give 0.70 g of bis acylated product. A mixture of this product in 13 ml of tetrahydrofuran-methanol (9: 4) and 2.3 ml of 1N NaOH is stirred for 18 hours at room temperature. To the mixture is added 2.3 ml of 1N HCl and the solvent removed. The mixture is triturated with 50 ml of $CH_2Cl_2$, filtered and the solid washed with $CH_2Cl_2$ and water to give 0.27 g of off-white crystals, m.p. 280°–284° C.

EXAMPLE 363

N-[4-[(4,5-Dihydro-6H-isoxazolo[5,4-d]thieno[3,2, b]azepin-6-yl)carbonyl]phenyl]-5-fluoro-2-methylbenzamide As described for Example 1, a solution of 2 mmol of 5,6-dihydro-6-(4-aminobenzoyl)-4H-isoxazolo [5,4-d] thieno[3,2-b]azepine and 5 mmol of triethylamine is reacted with 2.2 mmol of 5-fluoro-2-methylbenzoyl chloride in 10 ml of dichloromethane under argon for 16 hours to give the product as a solid.

The subject compounds of the present invention are tested for biological activity.

Binding Assay to Rat Hepatic $V_1$ Receptors

Rat liver plasma membranes expressing the vasopressin $V_1$ receptor subtypes are isolated by sucrose density gradient according to the method described by Lesko et al., (1973). These membranes are quickly suspended in 50.0 mM Tris.HCl buffer, pH 7.4, containing 0.2% bovine serum albumin (BSA) and 0.1 mM phenylmethylsulfonylfluoride (PMSF) and kept frozen at –70° C. until used in subsequent binding experiments. For binding experiments, the following is added to the wells of a ninety-six well format microtiter plate: 100 µl of 100.0 mM Tris.HCl buffer containing 10.0 mM $MgCl_2$, 0.2% heat inactivated BSA and a mixture of protease inhibitors: leupeptin, 1.0 mg %; aprotinin, 1.0 mg %, 1,10-phenanthroline, 2.0 mg %; trypsin inhibitor, 10.0 mg % and 0.1 mM PMSF, 20.0 µl of [phenylalanyl-3,4,5-3H] vasopressin (S.A. 45.1 Ci/mmole) at 0.8 nM, and the reaction initiated by the addition of 80 µl of tissue membranes containing 20 µg of tissue protein. The plates are kept undisturbed on the bench top at room temperature for 120 min. to reach equilibrium. Non-specific samples are assayed in the presence of 0.1 µM of the unlabeled antagonist phenylalanylvasopressin, added in 20.0 µl volume to a final incubation volume of 200 µl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, Ohio).

Binding Assay to Rat Kidney Medullary $V_2$ Receptors

Medullary tissues from rat kidneys are dissected out, cut into small pieces and let soak in a 0.154 mM sodium chloride solution containing 1.0 mM EDTA with many changes of the liquid phase, until the solution is clear of blood. The tissue is homogenized in a 0.25 M sucrose solution containing 1.0 mM EDTA and 0.1 mM PMSF using a Potter-Elvehjem homogenizer with a teflon pestle. The homogenate is filtered through several layers (4 layers) of cheese cloth. The filtrate is rehomogenized using a dounce homogenizer, with a tight fitting pestle. The final homogenate is contrifuged at 1500 x g for 15 min. The nuclear pellet is discarded and the supernatant fluid recentrifuged at 40,000 x g for 30 min. The resulting pellet formed contains a dark inner part with the exterior, slightly pink. The pink outer part is suspended in a small amount of 50.0 mM Tris.HCl buffer, pH 7.4. The protein content is determined by the Lowry's method (Lowry et al, J. Biol. Chem., 1953). The membrane suspension is stored at –70° C., in 50.0 mM Tris.HCl, containing 0.2% inactivated BSA and 0.1 mM PMSF in aliquots of 1.0 ml containing 10.0 mg protein per ml of suspension until use in subsequent binding experiments.

For binding experiments, the following is added in µl volume to wells of a 96 well format of a microtiter plate: 100.0 µl of 100.0 mM Tris.HCl buffer containing 0.2% heat inactivated BSA, 10.0 mM $MgCl_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 µl of [$^3$H] Arginine$^8$, vasopressin (S.A. 75.0 Ci/mmole) at 0.8 nM and the reaction initiated by the addition of 80.0 µl of tissue membranes (200.0 µg tissue protein). The plates are left undisturbed on the bench top for 120 min. to reach equilibrium. Non-specific binding is assessed in the presence of 1.0 μM of unlabeled ligand, added in 20 μl volume. For test compounds, these are solubilized in 50% dimethylsulfoxide (DMSO) and added in 20.0 μl volume to a final incubation volume of 200 μl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, Ohio).

Radioligand Binding Experiments with Human Platelet Membranes

Platelet Source: Hudson Valley Blood Services, Westchester Medical Center, Valhalla, N.Y.

Platelet Membrane Preparation:

Frozen platelet rich plasma (PRP), received from the Hudson Valley Blood Services are thawed to room temperature. The tubes containing the PRP are centrifuged at 16,000 x g for 10 min. at 4° C. and the supernarant fluid discarded. The platelets resuspended in an equal volume of 50.0 mM Tris-HCl, pH 7.5 containing 120 mM NaCl and 20.0 mM EDTA. The suspension is recentrifuged at 16,000 x g for 10 min. This washing step is repeated one more time. The wash is discarded and the lysed pellets homogenized in low ionic strength buffer of Tris.HCl, 5.0 mM, pH 7.5 containing 5.0 mM EDTA. The homogenate is centrifuged at 39,000 x g for 10 min. The resulting pellet is resuspended in Tris.HCl buffer, 70.0 mM, pH 7.5 and recentrifuged at 39,000 x g for 10 min. The final pellet is resuspended in 50.0 mM Tris.HCl buffer pH 7.4 containing 120 mM NaCl and 5.0 mM HCl to give 1.0–2.0 mg protein per ml of suspension.

Binding to Vasopressin $V_1$ Receptor Subtype in Human Platelet Membranes:

In wells of a 96 well format microtiter plate, add 100 μl of 50.0 mM Tris.HCl buffer containing 0.2% BSA and a mixture of protease inhibitors (aprotinin, leupeptin etc.). Then add 20 μl of [$^3$H]Ligand: (Manning or Arg$^8$Vasopressin), to give final concentrations ranging from 0.01 to 10.0 nM. Initiate the binding by adding 80.0 μl of platelet suspension (approx. 100 μg protein). Mix all reagents by pipetting the mixture up and down a few times. Non-specific binding is measured in the presence of 1.0 μM of unlabeled ligand (Manning or Arg$^8$Vasopressin). Let the mixture stand undisturbed at room temperature for ninety (90) min. Upon this time, rapidly filter off the incubate under vacuum suction over GF/B filters, using a Brandel® Harvester. Determine the radioactivity caught on the filter disks by the addition of liquid scintillant and counting in a liquid scintillator Binding to Membranes of Mouse Fibroblast Cell Line (LV$_2$) Transfected with the cDNA expressing the Human $V_2$ Vasopressin Receptor Membrane Preparation Flasks of 175 ml capacity, containing attached cells grown to confluence are cleared of culture medium by aspiration. The flasks containing the attached cells are rinsed with 2×5 ml of phosphate buffered saline (PBS) and the liquid aspirated off each time. Finally, 5 ml of an enzyme free dissociation Hank's based solution (Specialty Media, Inc., Lafayette, N.J.) is added and the flasks are left undisturbed for 2 min. The content of all flasks is poured into a centrifuge tube and the cells pelleted at 300 x g for 15 min. The Hank's based solution is aspirated off and the cells homogenized with a polytron at setting #6 for 10 sec in 10.0 mM Tris-HCl buffer, pH 7.4 containing 0.25 M sucrose and 1.0 mM EDTA. The homogenate is centrifuged at 1500 x g for 10 min to remove ghost membranes. The supernatant fluid is centrifuged at 100,000 x g for 60 min to pellet the receptor protein. Upon completion, the pellet is resuspended in a small volume of 50.0 mM Tris.HCl buffer, pH 7.4. The protein content is determined by the Lowry method and the receptor membranes are suspended in 50.0 mM Tris.HCl buffer containing 0.1 mM phenylmethylsulfonylfluoride (PMSF) and 0.2% bovine serum albumin (BSA) to give 2.5 mg receptor protein per ml of suspension.

Receptor Binding

For binding experiments, the following is added in μl volume to wells of a 96 well format of a microtiter plate: 100.0 μl of 100.0 mM Tris.HCl buffer containing 0.2% heat inactivated BSA, 10.0 mM $MgCl_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 μl of [$^3$H]Arginine$^8$, vasopressin (S.A. 75.0 Ci/mmole) at 0.8 nM and the reaction initiated by the addition of 80.0 μl of tissue membranes (200.0 μg tissue protein). The plates are left undisturbed on the bench top for 120 min to reach equilbrium. Non-specific binding is assessed in the presence of 1.0 μM of unlabeled ligand, added in 20 μl volume. For test compounds, these are solubilized in 50% dimethylsulfoxide (DMSO) and added in 20.0 μl volume to a final incubation volume of 200 μl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, Ohio).

Vasopressin $V_2$ Antagonist Activity in Conscious Hyrdated Rats

Conscious hydrated rats are treated with compounds under study from 0.1 to 100 mg/kg orally or vehicle. Two to four rats are used for each compound. One hour later, arginine vasopressin (AVP, antidiuretic hormone, ADH) dissolved in peanut oil is administered at 0.4 μg/kg intraperitoneally. Two rats in each test would not receive arginine vasopressin but only the vehicle (peanut oil) to serve as water-loading control. Twenty minutes later each rat is given 30 mL/kg of deionized water orally by gavage and is placed individually in a metabolic cage equipped with a funnel and a graduated glass cylinder to collect urine for four hours. Urine volume is measured and osmolality analyzed by use of a Fiske One-Ten osmometer (Fiske Assoc., Norwood, Mass. U.S.A.). Urinary sodium, potassium, and chloride are analyzed by use of ion-specific electrodes in a Beckman E3 (Electrolyte 3) Analyzer.

In the following results, decreased urine volume and decreased osmolality relative to AVP-control indicates activity. The results of this test on representative compounds of this invention are shown in Table 2.

Vasopressin $V_1$ Antagonist Activity in Conscious Rats

Conscious rats are restrained in a supine position with elastic tape. The area at the base of the tail is locally anesthetized by subcutaneous infiltration with 2% procaine (0.2 ml). Using aseptic technique the ventral caudal tail artery is isolated and a cannula made of PE 10 and 20 (heat-fused) tubing is passed into the lower abdominal aorta. The cannula is secured, heparinized (1000 i.u./cc), sealed and the would closed with one or two stitches of Dexon 4-0. The caudal vein is also cannulated in the same manner for intravenous drug administration. The duration of the surgery is approximately 5 minutes. Additional local anesthesia (2% procaine or lidocaine) is provided as needed.

The animals are placed in plastic restraining cages in an upright position. The cannula is attached to a Statham P23Db pressure transducer and pulsatile blood pressure is recorded. Increase of systolic blood pressure responses to arginine vasopressin 0.01 and 0.2 international unit (I.U.)(350 I.U.=1 mg) injections are recorded prior to any drug (compound) administration, after which each rat is dosed orally with compounds under study 0.1–100 mg/kg (10 cc/kg) or intravenously 0.1–30 mg/kg (1 cc/kg). The vasopressin injections are repeated 30,60,90,120,180,240 and 300 min. later. Percentage of antagonism by the compound is calculated using the pre-drug vasopressin vasopressor response as 100%.

TABLE 1

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

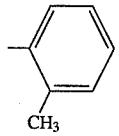

| Ex. No. | R | $R_1$ | Ar | A | $V_1$ | IC$_{50}$ (μM) $V_2$ |
|---|---|---|---|---|---|---|
| 361 | CH$_3$ | H | 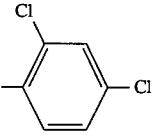 | CH | 2.01 *1.74 | 0.024 **0.22 |
| 5 | CH$_3$ | H | 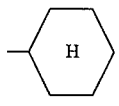 | CH | 2.1 *4.1 | 0.038 **0.15 |
| 6 | CH$_3$ | H | 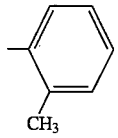 | CH | 4.7 | 0.23 |
| 7 | H | H | 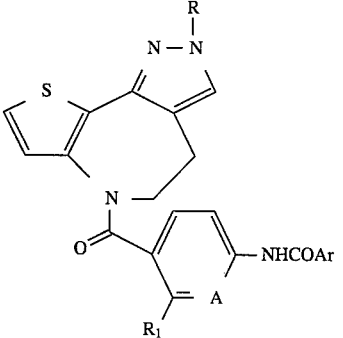 | CH | 2.1 *0.24 | 0.12 **0.13 |

TABLE 1-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

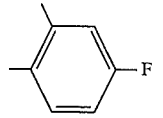

| Ex. No. | R | $R_1$ | Ar | A | $V_1$ | IC$_{50}$ (μM) $V_2$ |
|---|---|---|---|---|---|---|
| 1 | H | H | 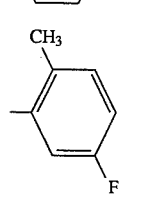 | CH | 2.0 | 0.34 |
| 2 | H | H | 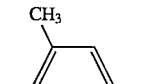 | CH | 1.7 | 0.069 **0.071 |
| 3 | H | Cl | 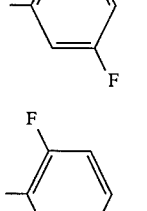 | CH | 24% at 1 μM | 0.0061 |
| 4 | H | Cl | 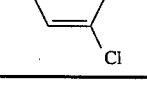 | CH | 8% at 1 μM | 0.036 |

TABLE 2

Vasopressin $V_2$ Antagonist Activity In Conscious Hydrated Rats

| Ex. No. | Dose (mg/kg) | N | Urine Vol. (ml/4 hrs.) | Osmolality (mOsm/kg) |
|---|---|---|---|---|
| * |  | 78 | 13.3 ± 0.3 | 229 ± 6 |
| ** |  | 6 | 12.1 ± 1 | 497 ± 53 |
|  |  | 4 | 12.4 ± 0.8 | 361 ± 30 |
| *** |  | 76 | 2 ± 0.2 | 1226 ± 58 |

TABLE 2-continued

Vasopressin $V_2$ Antagonist Activity In Conscious Hydrated Rats

| Ex. No. | Dose (mg/kg) | N | Urine Vol. (ml/4 hrs.) | Osmolality (mOsm/kg) |
|---|---|---|---|---|
| 1 | 10 | 2 | 15.3 | 535 |
| 2 | 10 | 2 | 17.8 | 429 |
| 7 | 10 | 2 | 20.8 | 322 |

*Water-load control
**Water-load Control + DMSO (10%) (20%)
***AVP-control

Oxytocin Receptor Binding (a) Membrane Preparation

Female Sprague-Dawley rats weighing approximately 200–250 g are injected intramuscularly (i.m.) with 0.3 mg/kg of body weight of diethylstilbestrol (DES). The rats are sacrificed 18 hours later under pentobarbital anesthesia. The uteri are dissected out, cleaned of fat and connective tissues and rinsed in 50 ml of normal saline. The tissue pooled from six rats is homogenized in 50 ml of 0.01 mM Tris.HCl, containing 0.5 mM dithiothreitol and 1.0 mM EDTA, adjusted to pH 7.4, using a polytron at setting 6 with three passes of 10 sec each. The homogenate is passed through two (2) layers of cheesecloth and the filtrate centrifuged at 1000 x g for 10 min. The clear supernatant is removed and recentrifuged at 165,000 x g for 30 min. The resulting pellet containing the oxytocin receptors is resuspended in 50.0 mM Tris.HCl containing 5.0 mM $MgCl_2$ at pH 7.4, to give a protein concentration of 2.5 mg/ml of tissue suspension. This preparation is used in subsequent binding assays with [$^3$H]Oxytocin.

(b) Radioligand Binding

Binding of 3,5-[$^3$H]Oxytocin ([$^3$H]OT) to its receptors is done in microtiter plates using [$^3$H]OT, at various concentrations, in an assay buffer of 50.0 mM Tris.HCl, pH 7.4 and containing 5.0 mM $MgCl_2$, and a mixture of protease inhibitors: BSA, 0.1 mg; aprotinin, 1.0 mg; 1,10-phenanthroline, 2.0 mg; trypsin, 10.0 mg; and PMSF, 0.3 mg per 100 ml of buffer solution. Non-specific binding is determined in the presence of 1.0 uM unlabeled OT. The binding reaction is terminated after 60 min., at 22° C., by rapid filtration through glass fiber filters using a Brandel® cell harvester (Biomedical Research and Development Laboratories, Inc., Gaithersburg, Md.). Competition experiments are conducted at equilibrium using 1.0 nM [$^3$H]OT and varying the concentration of the displacing agents. The concentrations of agent displacing 50% of [$^3$H]OT at its sites ($IC_{50}$) are calculated by a computer assisted LUNDON-2 program (LUNDON SOFTWARE INC., Ohio, U.S.A.).

The results of this assay on representative examples are shown in Table 3.

TABLE 3

Oxytocin Binding Assay

| Ex. No. | Dose (μM) | % Inhibition at 10 μM | $IC_{50}$ (μM) |
|---|---|---|---|
| 361 | 10 | 57 | 6.4 |
| 5 | 10 | 47 | |

TABLE 3-continued

Oxytocin Binding Assay

| Ex. No. | Dose (μM) | % Inhibition at 10 μM | $IC_{50}$ (μM) |
|---|---|---|---|
| 6 | 10 | 94 | 1.7 |
| 7 | 10 | 65 | |
| 1 | 10 | 93 | 2.5 |
| 2 | 10 | 91 | 1.3 |
| 3 | 1 | 21 | |
| 4 | 1 | 0 | |

The compounds of the present invention can be used in the form of salts derived from pharmaceutically or physiologically acceptable acids or bases. These salts include, but are not limited to, the following: salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases. The compounds can also be used in the form of esters, carbamates and other conventional "pro-drug" forms, which, when administered in such form, convert to the active moiety in vivo.

When the compounds are employed for the above utilities, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired.

Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The new tricyclic non-peptide vasopressin antagonists of this invention are useful in treating conditions where decreased vasopressin levels are desired, such as in congestive heart failure, in disease conditions with excess renal water reabsorption and in conditions with increased vascular resistance and coronary vasoconstriction.

In particular, the vasopressin antagonists of this invention are therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, thrombosis-bleeding and abnormal states of water retention.

In particular, the oxytocin antagonists of this invention are useful in the prevention of preterm labor and premature birth which is a significant cause of infant health problems and infant mortality.

What is claimed is:

1. A compound selected from Formula I:

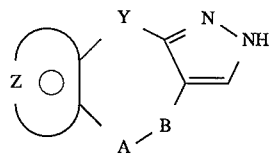

Formula I wherein:

Y is a bond;

the moiety

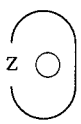

represents an optionally substituted fused thiophene or furan ring selected from the structures:

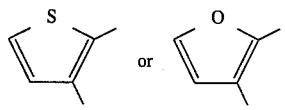

the fused thiophene or furan ring being optionally substituted by one or two substituents selected from the group of $(C_1-C_3)$ lower alkyl, halogen, amino, $(C_1-C_3)$ lower alkoxy, or $(C_1-C_3)$ lower alkyl amino;

the moiety

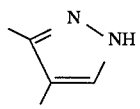

being optionally substituted by one or two substituents selected from the group of $(C_1-C_3)$ lower alkyl, halogen, amino, $(C_1-C_3)$ lower alkoxy, or $(C_1-C_3)$ lower alkyl amino;

A—B is a moiety selected from

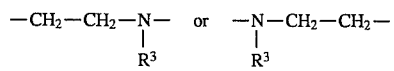

$R^3$ is —COAr, wherein Ar is a moiety selected from the group consisting of:

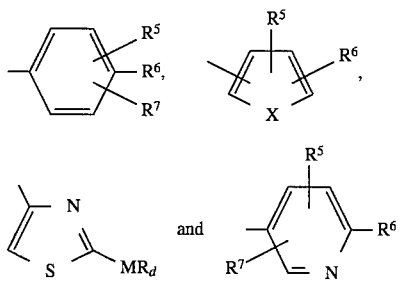

wherein

X is selected from O, S, —NH, —NCH$_3$ and —NCOCH$_3$;

$R^1$ and $R^2$ are selected from H, lower alkyl $(C_1-C_3)$, lower alkoxy $(C_1-C_3)$ and halogen;

$R^4$ is selected from H, lower alkyl $(C_1-C_3)$, —CO-lower alkyl $(C_1-C_3)$;

$R^5$ is selected from H, $(C_1-C_3)$ lower alkyl, $(C_1-C_3)$ lower alkoxy, and halogen;

$R^6$ is selected from;

(a) the moieties of the formulae:

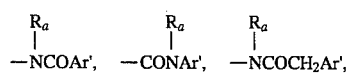

-continued

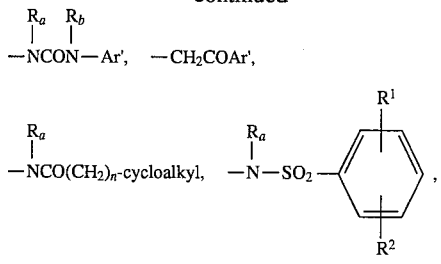

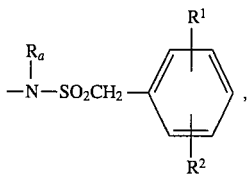

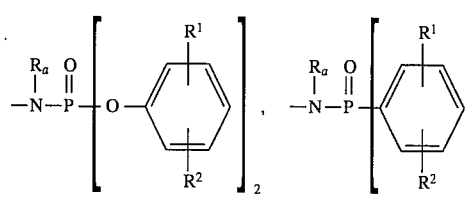

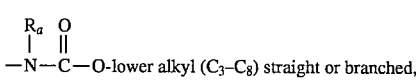

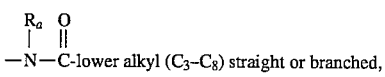

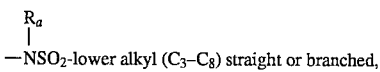

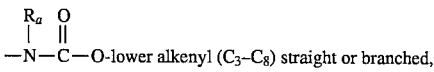

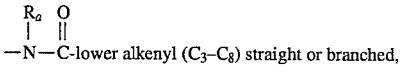

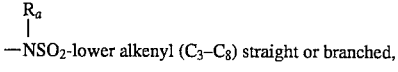

wherein n is 1 or 2;

cycloalkyl is defined as $C_3$–$C_6$ cycloalkyl, cyclohexenyl or cyclopentenyl;

$R_a$ is independently selected from hydrogen, —$CH_3$, —$C_2H_5$, moieties of the formulae:

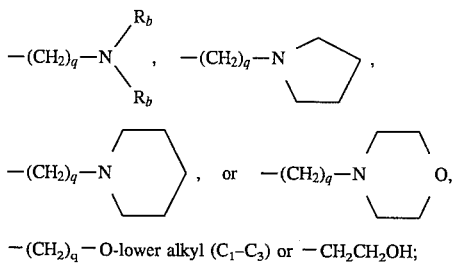

—$(CH_2)_q$—O-lower alkyl ($C_1$–$C_3$) or —$CH_2CH_2OH$;

q is one or two;

$R_b$ is independently selected from H, —$CH_3$, or —$C_2H_5$;

(b) a moiety of the formula:

wherein

J is $R_a$, lower alkyl ($C_3$–$C_8$) branched or unbranched, lower alkenyl ($C_3$–$C_8$) branched or unbranched, —O-lower alkyl ($C_3$–$C_8$) branched or unbranched, —O-lower alkenyl ($C_3$–$C_8$) branched or unbranched, tetrahydrofuran, tetrahydrothiophene, the moieties:

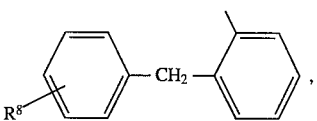

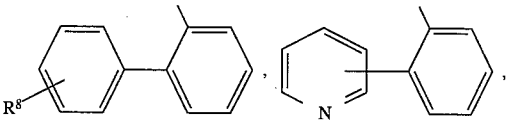

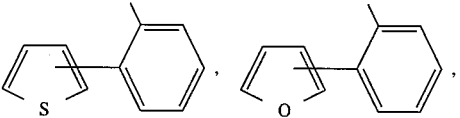

or —$CH_2$—K' wherein K' is ($C_1$–$C_3$) lower alkoxy, halogen, tetrahydrofuran, tetrahydrothiophene or the heterocyclic ring moiety:

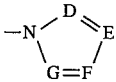

wherein D, E, F and G are selected from carbon or nitrogen and wherein the carbon atoms may be optionally substituted with halogen, ($C_1$–$C_3$) lower alkyl, hydroxy, —CO-lower alkyl ($C_1$–$C_3$), CHO, ($C_1$–$C_3$)lower alkoxy, or —CO-lower alkyl ($C_1$–$C_3$), and $R_a$ and $R_b$ are as hereinbefore defined;

(c) a moiety of the formula:

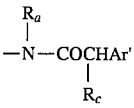

wherein $R_c$ is selected from halogen, ($C_1$–$C_3$)lower alkyl, —O-lower alkyl ($C_1$–$C_3$), OH, —O—C-lower alkyl ($C_1$–$C_3$), —S-lower alkyl ($C_1$–$C_3$),

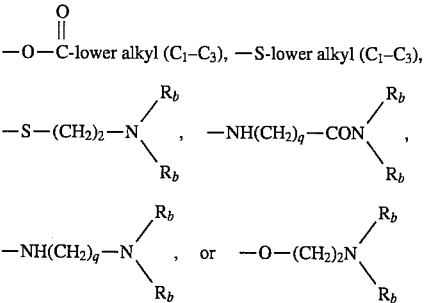

wherein $R_a$ and $R_b$ are as hereinbefore defined;

(d) a moiety of the formula:

—M—R$_d$ wherein R$_d$ is lower alkyl (C$_3$–C$_8$), lower alkenyl (C$_3$–C$_8$), or —(CH$_2$)$_p$-cycloalkyl (C$_3$–C$_6$) when M is O, S, NH, NCH$_3$ or the moiety —M—R$_d$ wherein R$_d$ is selected from the moieties:

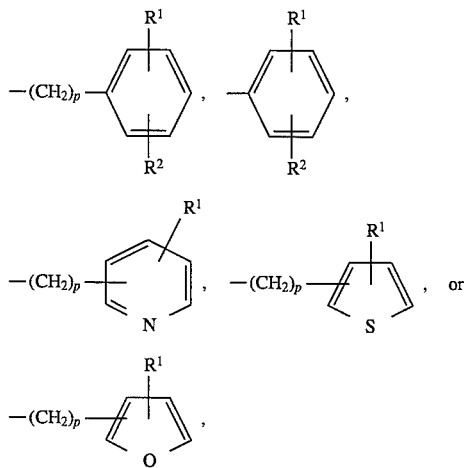

wherein
p is 0 to 4 and M is a bond or M is selected from O, S, NH or —NHCH$_3$;

R$^1$, R$^2$ and R$_a$ are as hereinbefore defined; wherein Ar' is selected from the moieties of the formula:

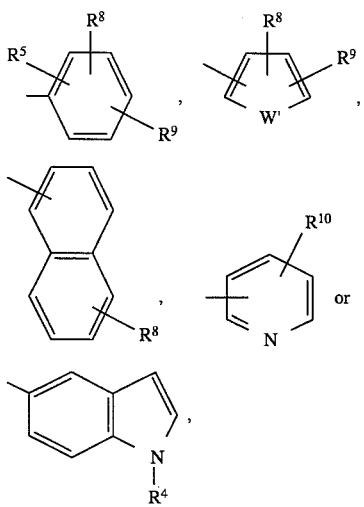

W' is selected from O, S, NH, N-lower alkyl (C$_1$–C$_3$), —NCO-lower alkyl (C$_1$–C$_3$), or NSO$_2$-lower alkyl(C$_1$–C$_3$);

R$^7$ is selected from H, lower alkyl (C$_1$–C$_3$), halogen, O-lower alkyl (C$_1$–C$_3$), and CF$_3$;

R$^8$ and R$^9$ are independently selected from H, lower alkyl (C$_1$–C$_3$), —S-lower alkyl (C$_1$–C$_3$), halogen, —NH-lower alkyl (C$_1$–C$_3$), —N-(lower alkyl (C$_1$–C$_3$))$_2$, —OCF$_3$, —OH, —CN, —S-CF$_3$, —NO$_2$, —NH$_2$, —O-lower alkyl (C$_1$–C$_3$), NHCO lower alkyl (C$_1$–C$_3$), —O—CO-lower alkyl (C$_1$–C$_3$), and —CF$_3$; and R$^{10}$ is selected from H, halogen, lower alkyl (C$_1$–C$_3$), —NH-lower alkyl (C$_1$–C$_3$), —N-[lower alkyl (C$_1$–C$_3$)]$_2$, —O-lower alkyl (C$_1$–C$_3$), —N(R$_b$)(CH$_2$)$_1$NR$_b$)$_2$;

or a pharmaceutically acceptable salt, ester or prodrug form thereof.

2. A compound of claim 1 which is N-[4-[(4,5-Dihydropyrazolo[3,4-d]thieno[3,2-b]azepin-6(1H)-yl)carbonyl]phenyl]-2-chloro-4-fluorobenzamide or a pharmaceutically acceptable salt, ester or prodrug form thereof.

3. A compound of claim 1 which is N-[4-[(4,5-Dihydropyrazolo[3,4-d]thieno[3,2-b]azepin-6(1H)-yl)carbonyl]phenyl]-5-fluoro-2-methylbenzamide or a pharmaceutically acceptable salt, ester or prodrug form thereof.

4. A compound of claim 1 which is N-[4-[(4,5-Dihydropyrazolo[3,4-d]thieno[3,2-b]azepin-6(1H)-yl)carbonyl]-3-chlorophenyl]-5-fluoro-2-methylbenzamide or a pharmaceutically acceptable salt, ester or prodrug form thereof.

5. A compound of claim 1 which is N-[4-[(4,5-Dihydropyrazolo[3,4-d]thieno[3,2-b]azepin-6(1H)-yl)carbonyl ]-3-chlorophenyl]-5-chloro-2-fluorobenzamide or a pharmaceutically acceptable salt, ester or prodrug form thereof.

6. A compound of claim 1 which is N-[4-[[4,5-Dihydro-2-methylpyrazolo[3,4-d]thieno[3,2-b]azepin-6(2H)-yl]carbonyl]phenyl]-2,4-dichlorobenzamide or a pharmaceutically acceptable salt, ester or prodrug form thereof.

7. A compound of claim 1 which is N-[4-[[4,5-Dihydro-2-methylpyrazolo[3,4-d]thieno[3,2-b]azepin-6(2H)-yl]carbonyl]phenyl]cyclohexane or a pharmaceutically acceptable salt, ester or prodrug form thereof.

8. A compound of claim 1 which is N-[4-[[4,5-Dihydropyrazolo[3,4-d]thieno[3,2-b]azepin-6(2H)-yl]carbonyl]phenyl]-2-methylbenzamide or a pharmaceutically acceptable salt, ester or prodrug form thereof.

9. A compound of claim 1 which is N-[5-[(4,5-Dihydropyrazolo[3,4-d]thieno[3,2-b]azepin-6(1H)-yl)carbonyl]-2-pyridinyl]-2-chloro-4-fluorobenzamide or a pharmaceutically acceptable salt, ester or prodrug form thereof.

10. A compound of claim 1 which is N-[5-[(4,5-Dihydropyrazolo[3,4-d]thieno[3,2-b]azepin-6(1H)-yl)carbonyl]-2-pyridinyl]-5-fluoro-2-methylbenzamide or a pharmaceutically acceptable salt, ester or prodrug form thereof.

11. A compound of claim 1 which is N-[5-[(4,5-Dihydropyrazolo[3,4-d]thieno[3,2-b]azepin-6(1H)-yl)carbonyl]-2-pyridinyl]-5-chloro-2-fluorobenzamide or a pharmaceutically acceptable salt, ester or prodrug form thereof.

12. A compound of claim 1 which is N-[5-[(4,5-Dihydropyrazolo[3,4-d]thieno[3,2-b]azepin-6(1H)-yl)carbonyl]-2-pyridinyl]-3-fluoro-2-methylbenzamide or a pharmaceutically acceptable salt, ester or prodrug form thereof.

13. A compound of claim 1 which is N-[5-[(4,5-Dihydropyrazolo[3,4-d]thieno[3,2-b]azepin-6(1H)-yl)carbonyl]-3-chloro-2-pyridinyl]-5-fluoro-2-methylbenzamide or a pharmaceutically acceptable salt, ester or prodrug form thereof.

14. A compound of claim 1 which is N-[5-[(4,5-Dihydropyrazolo[3,4-d]thieno[3,2-b]azepin-6(1H)-yl)carbonyl]-2-pyridinyl]-2-chloro-6-fluorobenzamide or a pharmaceutically acceptable salt, ester or prodrug form thereof.

15. A compound of claim 1 which is N-[4-[(4,5-Dihydropyrazolo[3,4-d]thieno[3,2-b]azepin-6(1H)-yl)carbonyl]-3-phenyl]-2-(dimethylamino)pyridine-3-carboxamide or a pharmaceutically acceptable salt, ester or prodrug form thereof.

16. A compound of claim 1 which is N-[5-[(4,5-Dihydropyrazolo[3,4-d]thieno[3,2-b]azepin-6(1H)-yl)carbonyl]-2-pyridinyl]-2-methylamino)pyridine-3-carboxamide or a pharmaceutically acceptable salt, ester or prodrug form thereof.

17. A pharmaceutical composition useful for treating disease in a mammal characterized by excess renal reabsorption of water, the pharmaceutical composition comprising an effective amount of a compound of claim 1, or a pharmaceutically acceptable salt, ester or prodrug form thereof, and a suitable pharmaceutical carder.

18. The pharmaceutical composition of claim 17 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

19. A method for treating disease in a mammal characterized by excess renal reabsorption of water, the method comprising administering to a mammal in need thereof an effective amount of a compound of claim 1, or a pharmaceutically acceptable salt, ester or prodrug form thereof, and a suitable pharmaceutical carrier.

20. The method of claim 19 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

* * * * *